US012564430B2

(12) United States Patent
    Castro

(10) Patent No.: US 12,564,430 B2
(45) Date of Patent: Mar. 3, 2026

(54) COMPUTERIZED PROCESS FOR MAKING A PATIENT-SPECIFIC IMPLANT

(71) Applicant: Blue Sky Technologies, LLC, Louisville, KY (US)

(72) Inventor: Frank Castro, Louisville, KY (US)

(73) Assignee: BLUE SKY TECHNOLOGIES, LLC, Louisville, KY (US)

( * ) Notice: Subject to any disclaimer, the term of this patent is extended or adjusted under 35 U.S.C. 154(b) by 618 days.

(21) Appl. No.: 18/088,531

(22) Filed: Dec. 24, 2022

(65) Prior Publication Data

US 2023/0255690 A1    Aug. 17, 2023

Related U.S. Application Data

(60) Provisional application No. 63/317,041, filed on Mar. 6, 2022, provisional application No. 63/310,189, filed on Feb. 15, 2022.

(51) Int. Cl.
| | |
|---|---|
| *A61B 17/84* | (2006.01) |
| *A61B 17/70* | (2006.01) |
| *A61B 17/88* | (2006.01) |
| *A61B 34/10* | (2016.01) |

(52) U.S. Cl.
CPC ............ *A61B 17/846* (2013.01); *A61B 17/70* (2013.01); *A61B 17/8808* (2013.01); *A61B 17/8811* (2013.01); *A61B 34/10* (2016.02); *A61B 2034/107* (2016.02); *A61B 2034/108* (2016.02)

(58) Field of Classification Search
CPC ........ A61B 2034/102; A61B 2034/105; A61B 2034/107; A61B 2034/108; A61B 17/70; A61B 17/7032; A61B 17/7082
See application file for complete search history.

(56) References Cited

U.S. PATENT DOCUMENTS

| | | | |
|---|---|---|---|
| 6,532,299 B1 | 3/2003 | Sachdeva et al. | |
| 7,993,347 B1 | 8/2011 | Michlelson | |
| 8,012,186 B2 | 9/2011 | Pham et al. | |
| 8,764,804 B2 | 7/2014 | Rezach | |
| 9,826,986 B2 | 11/2017 | Donner et al. | |
| 10,799,295 B1 | 10/2020 | Tjon | |
| 11,597,148 B2 * | 3/2023 | Reith ..................... | B33Y 10/00 |
| 2004/0015327 A1 | 1/2004 | Sachdeva et al. | |
| 2004/0171924 A1 * | 9/2004 | Mire ...................... | A61B 34/20 |
| | | | 600/407 |
| 2008/0275558 A1 | 11/2008 | Clifford et al. | |
| 2009/0312763 A1 | 12/2009 | McCormack et al. | |
| 2014/0081400 A1 | 3/2014 | Azernikov et al. | |
| 2015/0223939 A1 | 8/2015 | Miles et al. | |
| 2015/0250518 A1 | 9/2015 | Chirico et al. | |
| 2018/0271661 A1 | 9/2018 | Kamer et al. | |
| 2018/0353299 A1 | 12/2018 | Wei | |
| 2019/0167435 A1 | 6/2019 | Cordonnier | |
| 2019/0231436 A1 * | 8/2019 | Panse .................... | A61B 34/30 |
| 2019/0321193 A1 | 10/2019 | Casey et al. | |
| 2020/0129296 A1 | 4/2020 | Chary et al. | |
| 2020/0170802 A1 | 6/2020 | Casey | |
| 2021/0053291 A1 | 2/2021 | Bouvier et al. | |

(Continued)

*Primary Examiner* — Nicholas Klicos
(74) *Attorney, Agent, or Firm* — BUSINESS PATENT LAW, PLLC

(57) ABSTRACT

The present invention is a process of making a patient-specific implant for a patient. The current process is adaptable to manufacture spinal and other implants for insertion into the patient.

21 Claims, 39 Drawing Sheets

(56)  References Cited

U.S. PATENT DOCUMENTS

| | | | |
|---|---|---|---|
| 2022/0039965 A1 | 2/2022 | Casey et al. | |
| 2023/0081437 A1* | 3/2023 | Russell | A61B 34/30 |
| | | | 606/1 |
| 2023/0277246 A1* | 9/2023 | Casey | G06F 21/6245 |

* cited by examiner

*Prior Art*

666

C1

620,650,690

902b

937

600

40   40

666

903a

907

C2

620,650,690

902b

600

666

902a 620,650,690

902b

600

666

902a

FIG. 7: Pre-Operative Flow Sheet

FIG. 8: Post-Operative Flow Sheet

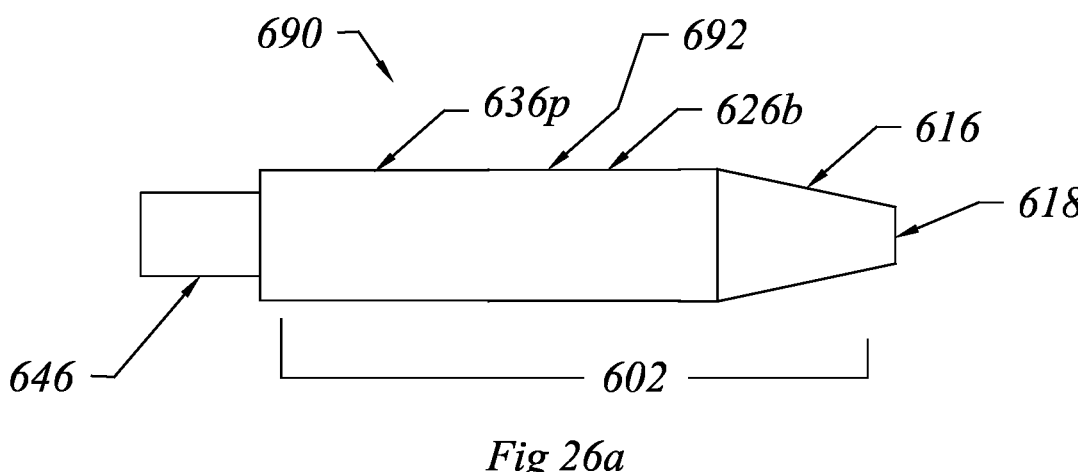
*Fig 26a*
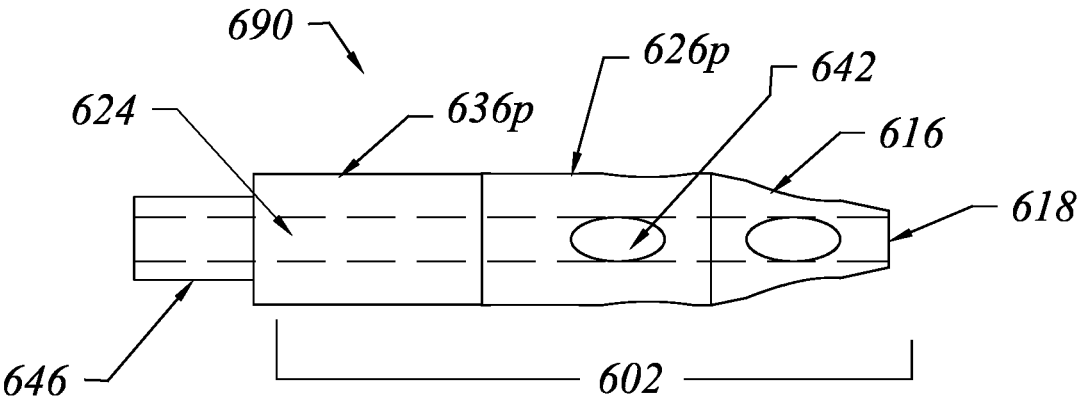
*Fig 26b*
*Fig 26c*

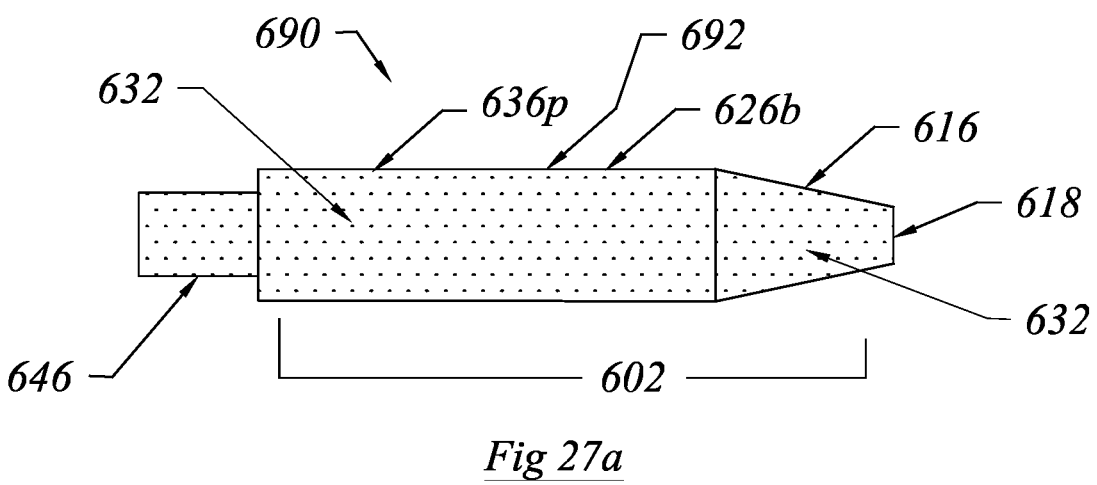
*Fig 27a*
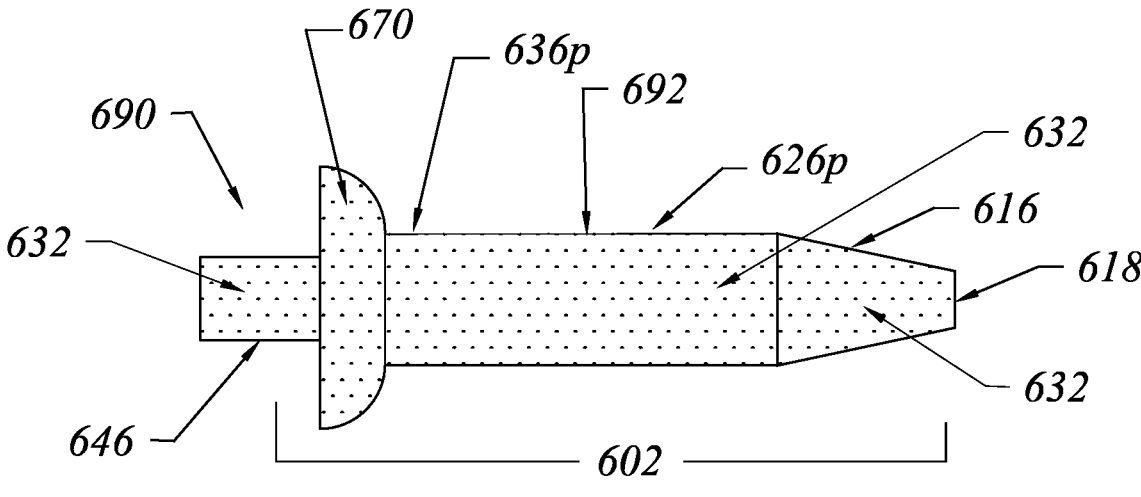
*Fig 27b*
*Fig 27c*

FIG 31

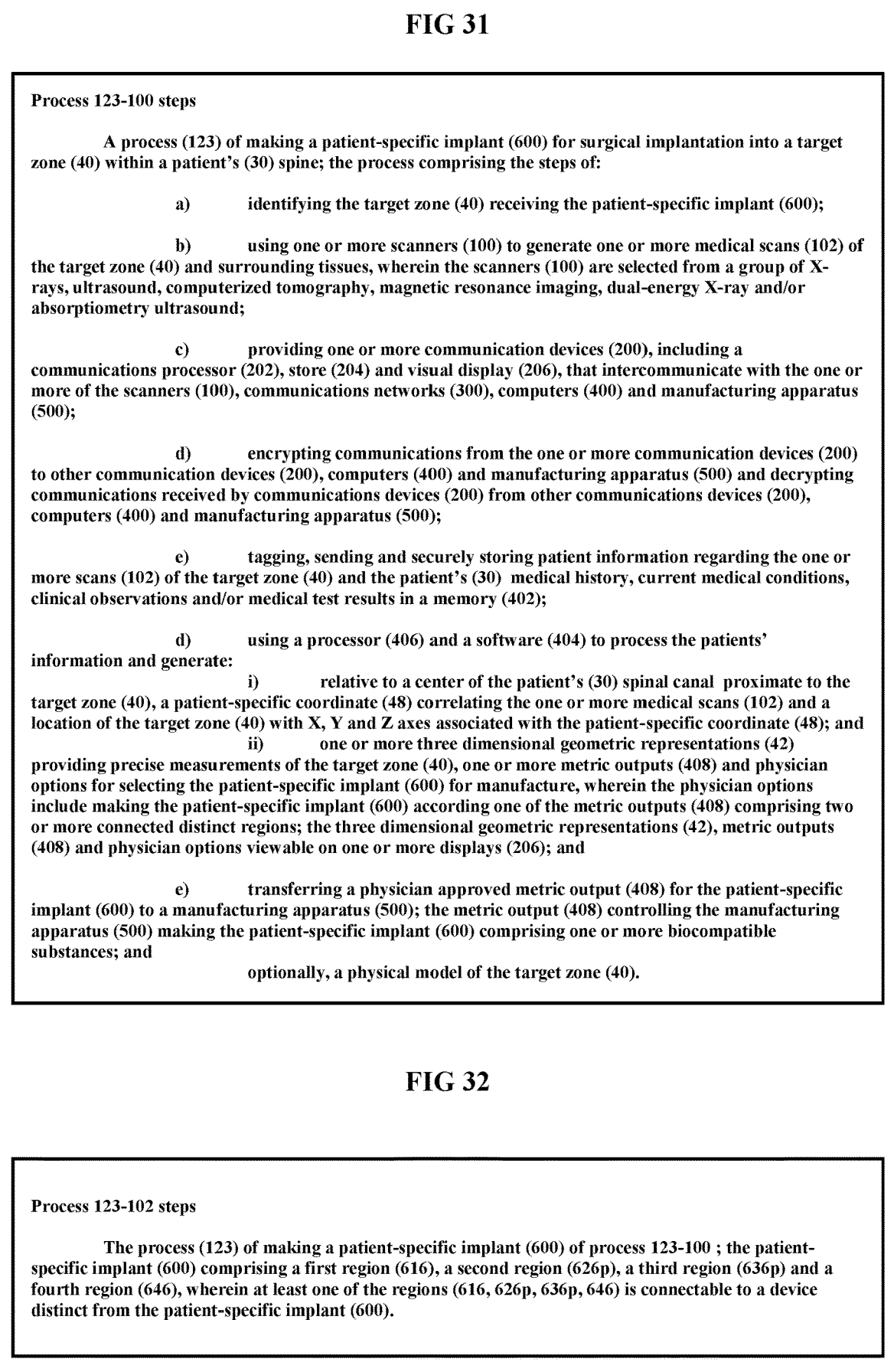

Process 123-100 steps

A process (123) of making a patient-specific implant (600) for surgical implantation into a target zone (40) within a patient's (30) spine; the process comprising the steps of:

a)        identifying the target zone (40) receiving the patient-specific implant (600);

b)        using one or more scanners (100) to generate one or more medical scans (102) of the target zone (40) and surrounding tissues, wherein the scanners (100) are selected from a group of X-rays, ultrasound, computerized tomography, magnetic resonance imaging, dual-energy X-ray and/or absorptiometry ultrasound;

c)        providing one or more communication devices (200), including a communications processor (202), store (204) and visual display (206), that intercommunicate with the one or more of the scanners (100), communications networks (300), computers (400) and manufacturing apparatus (500);

d)        encrypting communications from the one or more communication devices (200) to other communication devices (200), computers (400) and manufacturing apparatus (500) and decrypting communications received by communications devices (200) from other communications devices (200), computers (400) and manufacturing apparatus (500);

e)        tagging, sending and securely storing patient information regarding the one or more scans (102) of the target zone (40) and the patient's (30) medical history, current medical conditions, clinical observations and/or medical test results in a memory (402);

d)        using a processor (406) and a software (404) to process the patients' information and generate:
                         i)        relative to a center of the patient's (30) spinal canal proximate to the target zone (40), a patient-specific coordinate (48) correlating the one or more medical scans (102) and a location of the target zone (40) with X, Y and Z axes associated with the patient-specific coordinate (48); and
                         ii)        one or more three dimensional geometric representations (42) providing precise measurements of the target zone (40), one or more metric outputs (408) and physician options for selecting the patient-specific implant (600) for manufacture, wherein the physician options include making the patient-specific implant (600) according one of the metric outputs (408) comprising two or more connected distinct regions; the three dimensional geometric representations (42), metric outputs (408) and physician options viewable on one or more displays (206); and e)        transferring a physician approved metric output (408) for the patient-specific implant (600) to a manufacturing apparatus (500); the metric output (408) controlling the manufacturing apparatus (500) making the patient-specific implant (600) comprising one or more biocompatible substances; and
                     optionally, a physical model of the target zone (40).

FIG 32

Process 123-102 steps

The process (123) of making a patient-specific implant (600) of process 123-100 ; the patient-specific implant (600) comprising a first region (616), a second region (626p), a third region (636p) and a fourth region (646), wherein at least one of the regions (616, 626p, 636p, 646) is connectable to a device distinct from the patient-specific implant (600).

FIG 33

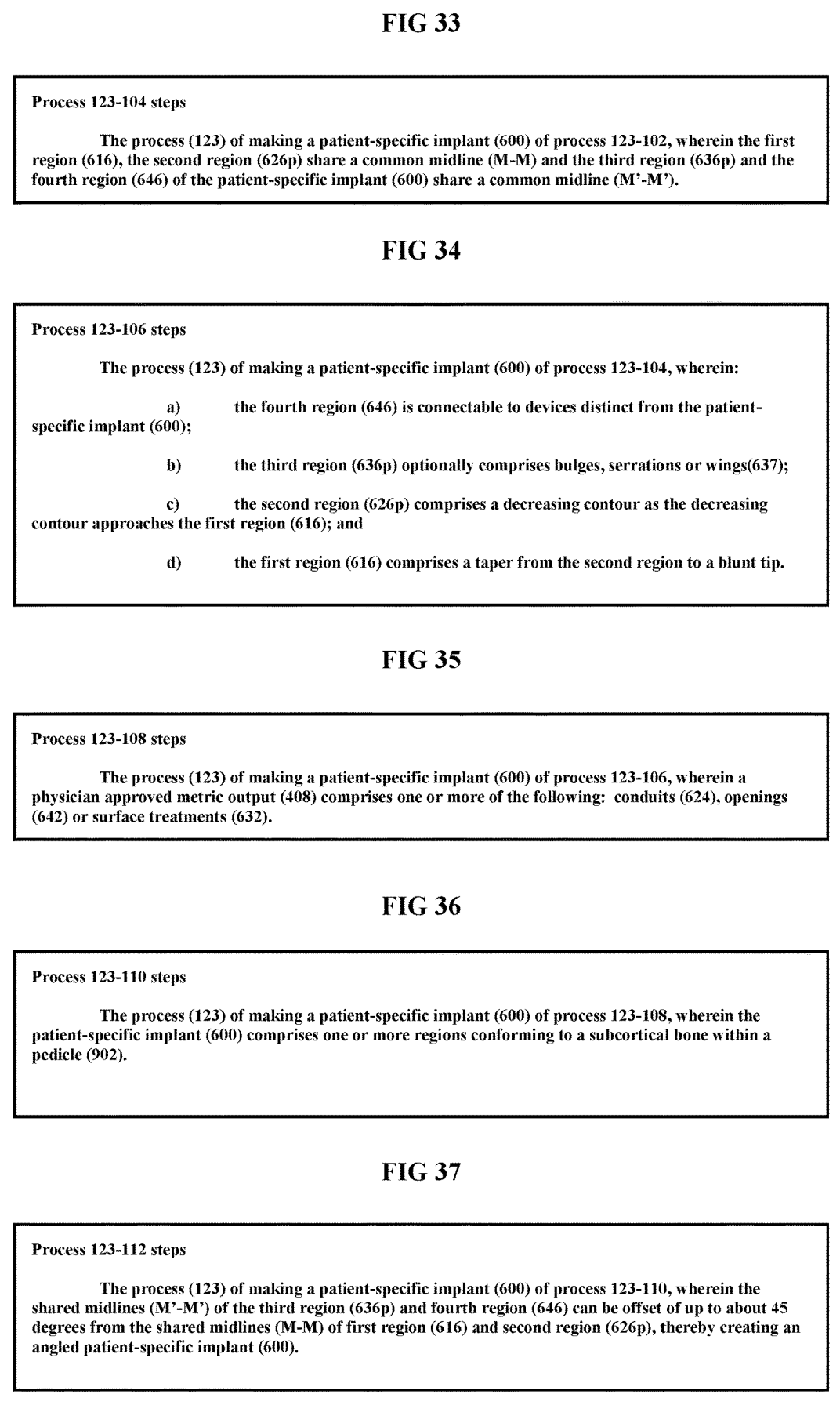

Process 123-104 steps

The process (123) of making a patient-specific implant (600) of process 123-102, wherein the first region (616), the second region (626p) share a common midline (M-M) and the third region (636p) and the fourth region (646) of the patient-specific implant (600) share a common midline (M'-M').

FIG 34

Process 123-106 steps

The process (123) of making a patient-specific implant (600) of process 123-104, wherein:

a)        the fourth region (646) is connectable to devices distinct from the patient-specific implant (600);

b)        the third region (636p) optionally comprises bulges, serrations or wings(637);

c)        the second region (626p) comprises a decreasing contour as the decreasing contour approaches the first region (616); and d)        the first region (616) comprises a taper from the second region to a blunt tip.

FIG 35

Process 123-108 steps

The process (123) of making a patient-specific implant (600) of process 123-106, wherein a physician approved metric output (408) comprises one or more of the following: conduits (624), openings (642) or surface treatments (632).

FIG 36

Process 123-110 steps

The process (123) of making a patient-specific implant (600) of process 123-108, wherein the patient-specific implant (600) comprises one or more regions conforming to a subcortical bone within a pedicle (902).

FIG 37

Process 123-112 steps

The process (123) of making a patient-specific implant (600) of process 123-110, wherein the shared midlines (M'-M') of the third region (636p) and fourth region (646) can be offset of up to about 45 degrees from the shared midlines (M-M) of first region (616) and second region (626p), thereby creating an angled patient-specific implant (600).

FIG 38

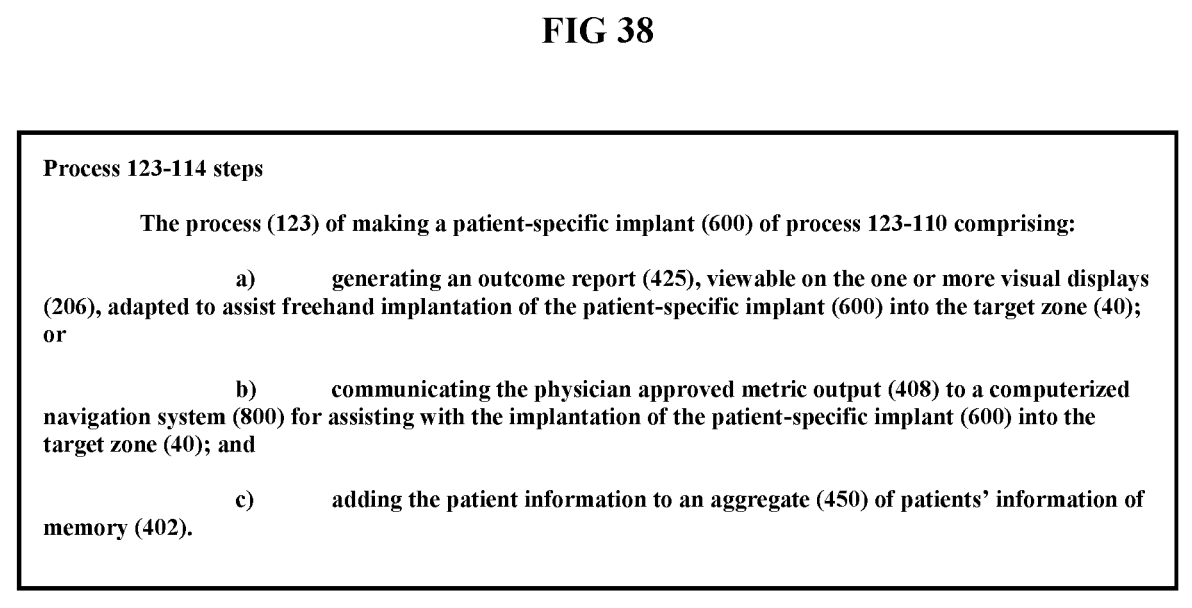

Process 123-114 steps

The process (123) of making a patient-specific implant (600) of process 123-110 comprising:

a)  generating an outcome report (425), viewable on the one or more visual displays (206), adapted to assist freehand implantation of the patient-specific implant (600) into the target zone (40); or b)  communicating the physician approved metric output (408) to a computerized navigation system (800) for assisting with the implantation of the patient-specific implant (600) into the target zone (40); and c)  adding the patient information to an aggregate (450) of patients' information of memory (402).

FIG 39

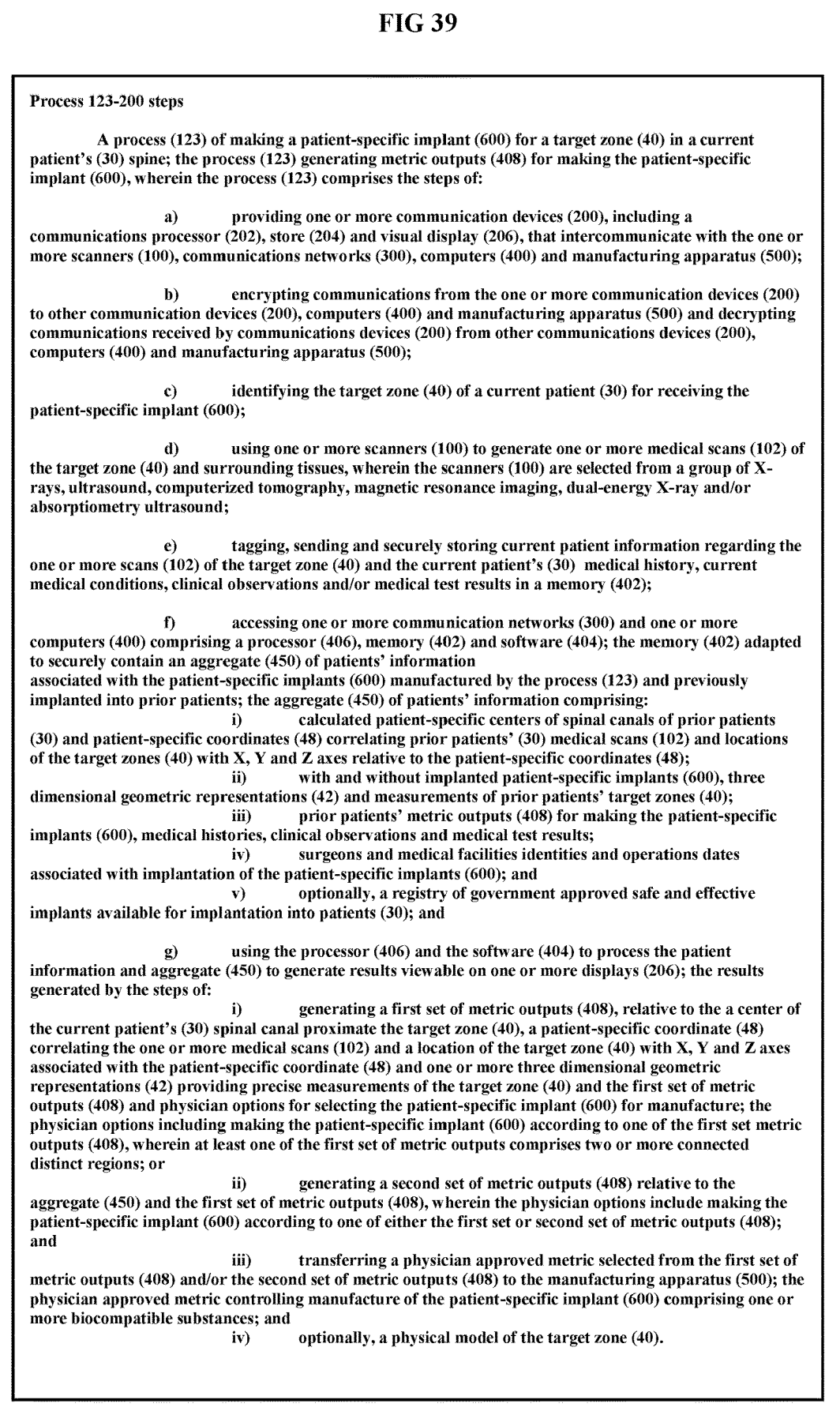

Process 123-200 steps

A process (123) of making a patient-specific implant (600) for a target zone (40) in a current patient's (30) spine; the process (123) generating metric outputs (408) for making the patient-specific implant (600), wherein the process (123) comprises the steps of:

a)        providing one or more communication devices (200), including a communications processor (202), store (204) and visual display (206), that intercommunicate with the one or more scanners (100), communications networks (300), computers (400) and manufacturing apparatus (500);

b)        encrypting communications from the one or more communication devices (200) to other communication devices (200), computers (400) and manufacturing apparatus (500) and decrypting communications received by communications devices (200) from other communications devices (200), computers (400) and manufacturing apparatus (500);

c)        identifying the target zone (40) of a current patient (30) for receiving the patient-specific implant (600);

d)        using one or more scanners (100) to generate one or more medical scans (102) of the target zone (40) and surrounding tissues, wherein the scanners (100) are selected from a group of X-rays, ultrasound, computerized tomography, magnetic resonance imaging, dual-energy X-ray and/or absorptiometry ultrasound;

e)        tagging, sending and securely storing current patient information regarding the one or more scans (102) of the target zone (40) and the current patient's (30)  medical history, current medical conditions, clinical observations and/or medical test results in a memory (402);

f)        accessing one or more communication networks (300) and one or more computers (400) comprising a processor (406), memory (402) and software (404); the memory (402) adapted to securely contain an aggregate (450) of patients' information
associated with the patient-specific implants (600) manufactured by the process (123) and previously implanted into prior patients; the aggregate (450) of patients' information comprising:
          i)        calculated patient-specific centers of spinal canals of prior patients (30) and patient-specific coordinates (48) correlating prior patients' (30) medical scans (102) and locations of the target zones (40) with X, Y and Z axes relative to the patient-specific coordinates (48);
          ii)        with and without implanted patient-specific implants (600), three dimensional geometric representations (42) and measurements of prior patients' target zones (40);
          iii)        prior patients' metric outputs (408) for making the patient-specific implants (600), medical histories, clinical observations and medical test results;
          iv)        surgeons and medical facilities identities and operations dates associated with implantation of the patient-specific implants (600); and
          v)        optionally, a registry of government approved safe and effective implants available for implantation into patients (30); and g)        using the processor (406) and the software (404) to process the patient information and aggregate (450) to generate results viewable on one or more displays (206); the results generated by the steps of:
          i)        generating a first set of metric outputs (408), relative to the a center of the current patient's (30) spinal canal proximate the target zone (40), a patient-specific coordinate (48) correlating the one or more medical scans (102) and a location of the target zone (40) with X, Y and Z axes associated with the patient-specific coordinate (48) and one or more three dimensional geometric representations (42) providing precise measurements of the target zone (40) and the first set of metric outputs (408) and physician options for selecting the patient-specific implant (600) for manufacture; the physician options including making the patient-specific implant (600) according to one of the first set metric outputs (408), wherein at least one of the first set of metric outputs comprises two or more connected distinct regions; or
          ii)        generating a second set of metric outputs (408) relative to the aggregate (450) and the first set of metric outputs (408), wherein the physician options include making the patient-specific implant (600) according to one of either the first set or second set of metric outputs (408); and
          iii)        transferring a physician approved metric selected from the first set of metric outputs (408) and/or the second set of metric outputs (408) to the manufacturing apparatus (500); the physician approved metric controlling manufacture of the patient-specific implant (600) comprising one or more biocompatible substances; and
          iv)        optionally, a physical model of the target zone (40).

FIG 40

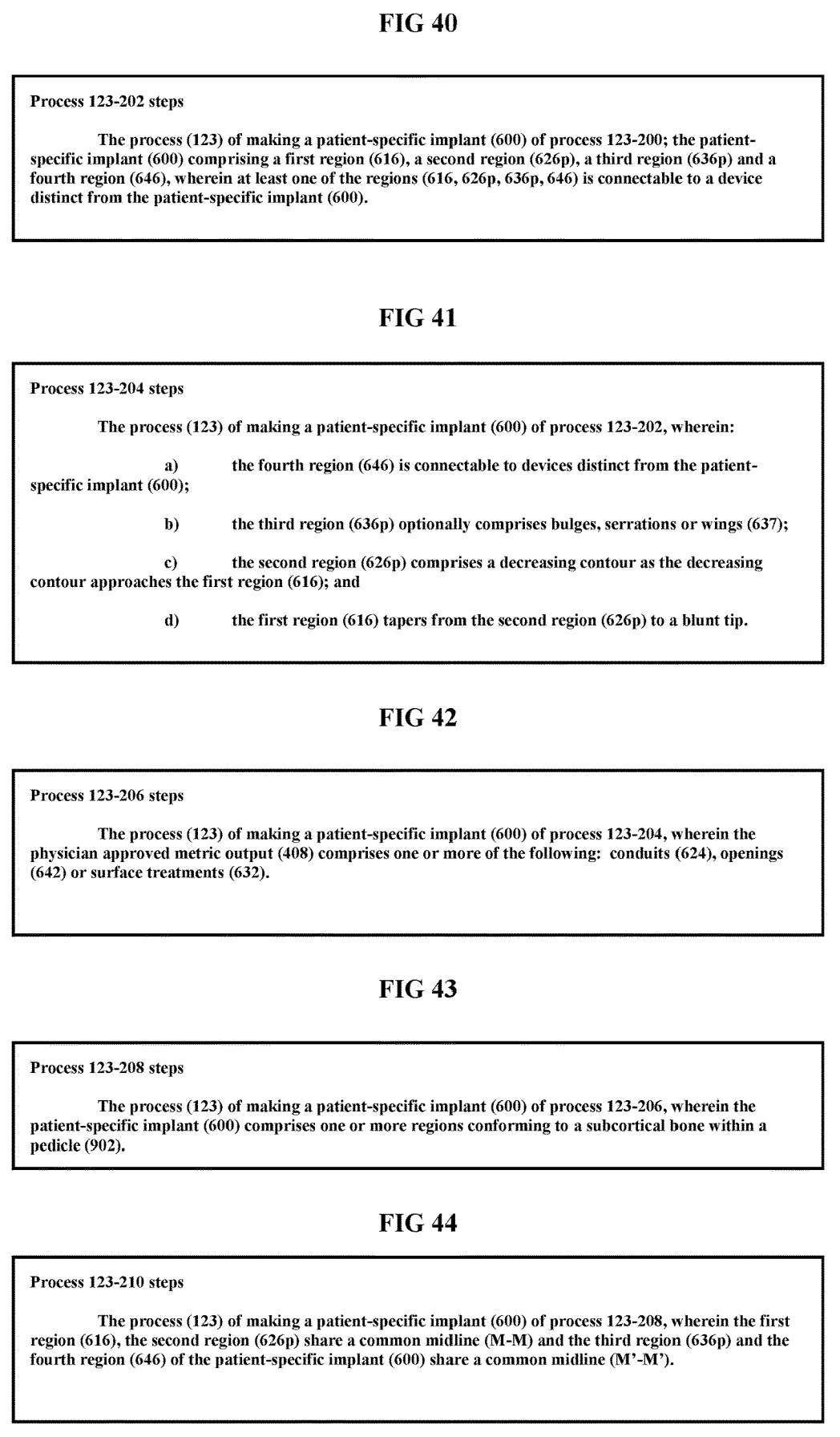

Process 123-202 steps

The process (123) of making a patient-specific implant (600) of process 123-200; the patient-specific implant (600) comprising a first region (616), a second region (626p), a third region (636p) and a fourth region (646), wherein at least one of the regions (616, 626p, 636p, 646) is connectable to a device distinct from the patient-specific implant (600).

FIG 41

Process 123-204 steps

The process (123) of making a patient-specific implant (600) of process 123-202, wherein:

a)     the fourth region (646) is connectable to devices distinct from the patient-specific implant (600);

b)     the third region (636p) optionally comprises bulges, serrations or wings (637);

c)     the second region (626p) comprises a decreasing contour as the decreasing contour approaches the first region (616); and d)     the first region (616) tapers from the second region (626p) to a blunt tip.

FIG 42

Process 123-206 steps

The process (123) of making a patient-specific implant (600) of process 123-204, wherein the physician approved metric output (408) comprises one or more of the following:  conduits (624), openings (642) or surface treatments (632).

FIG 43

Process 123-208 steps

The process (123) of making a patient-specific implant (600) of process 123-206, wherein the patient-specific implant (600) comprises one or more regions conforming to a subcortical bone within a pedicle (902).

FIG 44

Process 123-210 steps

The process (123) of making a patient-specific implant (600) of process 123-208, wherein the first region (616), the second region (626p) share a common midline (M-M) and the third region (636p) and the fourth region (646) of the patient-specific implant (600) share a common midline (M'-M').

FIG 45

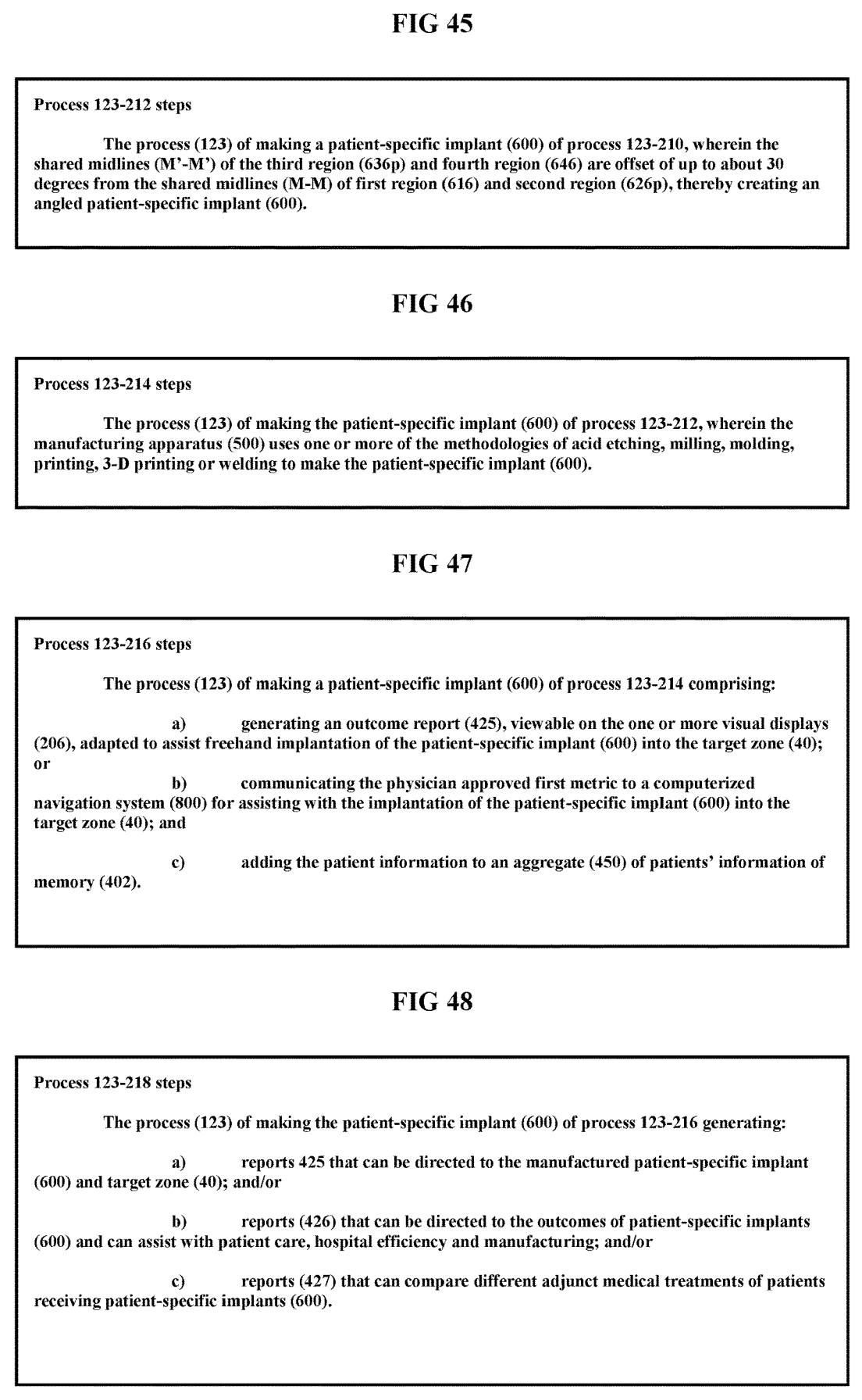

Process 123-212 steps

The process (123) of making a patient-specific implant (600) of process 123-210, wherein the shared midlines (M'-M') of the third region (636p) and fourth region (646) are offset of up to about 30 degrees from the shared midlines (M-M) of first region (616) and second region (626p), thereby creating an angled patient-specific implant (600).

FIG 46

Process 123-214 steps

The process (123) of making the patient-specific implant (600) of process 123-212, wherein the manufacturing apparatus (500) uses one or more of the methodologies of acid etching, milling, molding, printing, 3-D printing or welding to make the patient-specific implant (600).

FIG 47

Process 123-216 steps

The process (123) of making a patient-specific implant (600) of process 123-214 comprising:

a)          generating an outcome report (425), viewable on the one or more visual displays (206), adapted to assist freehand implantation of the patient-specific implant (600) into the target zone (40); or b)          communicating the physician approved first metric to a computerized navigation system (800) for assisting with the implantation of the patient-specific implant (600) into the target zone (40); and c)          adding the patient information to an aggregate (450) of patients' information of memory (402).

FIG 48

Process 123-218 steps

The process (123) of making the patient-specific implant (600) of process 123-216 generating:

a)          reports 425 that can be directed to the manufactured patient-specific implant (600) and target zone (40); and/or b)          reports (426) that can be directed to the outcomes of patient-specific implants (600) and can assist with patient care, hospital efficiency and manufacturing; and/or c)          reports (427) that can compare different adjunct medical treatments of patients receiving patient-specific implants (600).

FIG 49

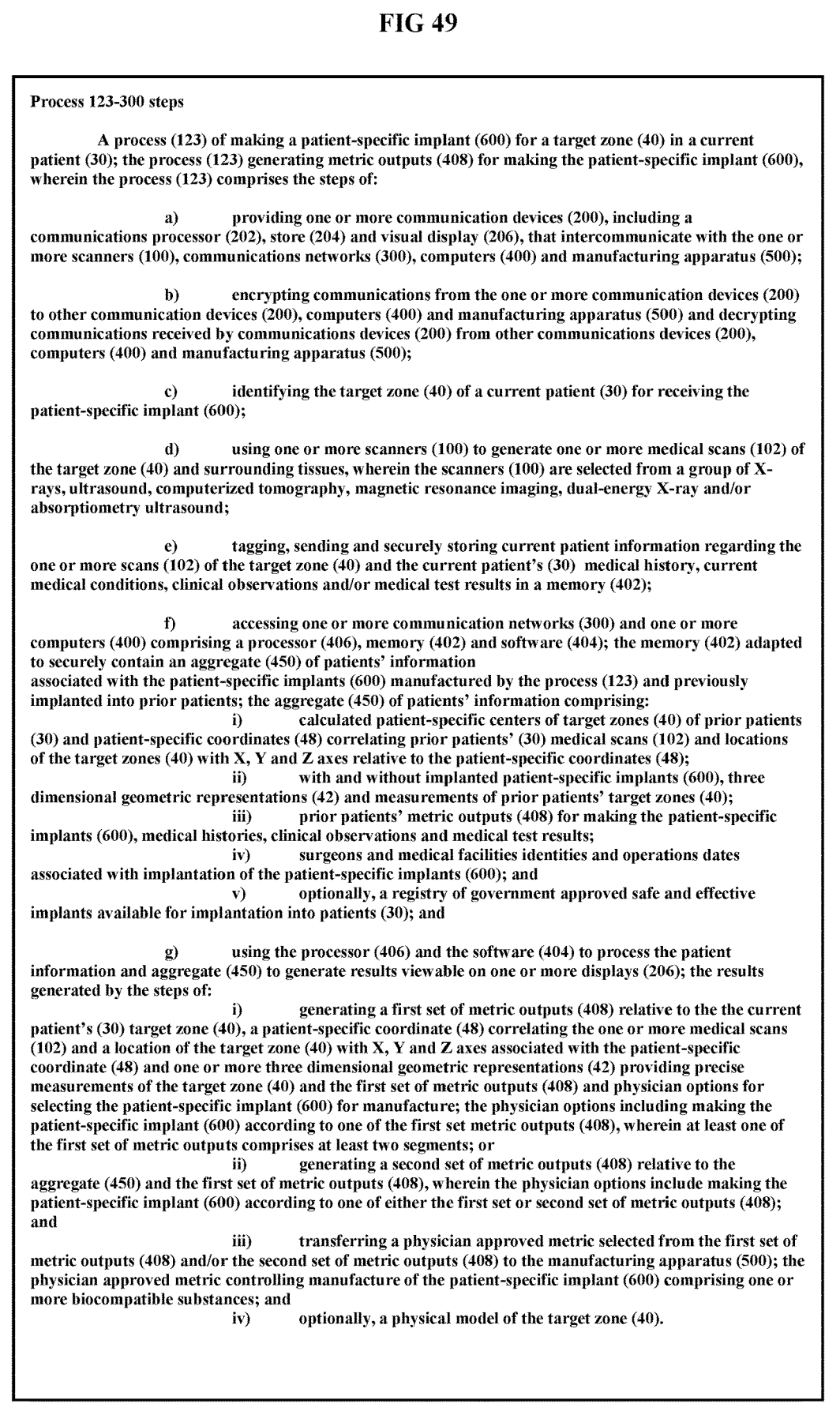

Process 123-300 steps

A process (123) of making a patient-specific implant (600) for a target zone (40) in a current patient (30); the process (123) generating metric outputs (408) for making the patient-specific implant (600), wherein the process (123) comprises the steps of:

a)      providing one or more communication devices (200), including a communications processor (202), store (204) and visual display (206), that intercommunicate with the one or more scanners (100), communications networks (300), computers (400) and manufacturing apparatus (500);

b)      encrypting communications from the one or more communication devices (200) to other communication devices (200), computers (400) and manufacturing apparatus (500) and decrypting communications received by communications devices (200) from other communications devices (200), computers (400) and manufacturing apparatus (500);

c)      identifying the target zone (40) of a current patient (30) for receiving the patient-specific implant (600);

d)      using one or more scanners (100) to generate one or more medical scans (102) of the target zone (40) and surrounding tissues, wherein the scanners (100) are selected from a group of X-rays, ultrasound, computerized tomography, magnetic resonance imaging, dual-energy X-ray and/or absorptiometry ultrasound;

e)      tagging, sending and securely storing current patient information regarding the one or more scans (102) of the target zone (40) and the current patient's (30) medical history, current medical conditions, clinical observations and/or medical test results in a memory (402);

f)      accessing one or more communication networks (300) and one or more computers (400) comprising a processor (406), memory (402) and software (404); the memory (402) adapted to securely contain an aggregate (450) of patients' information associated with the patient-specific implants (600) manufactured by the process (123) and previously implanted into prior patients; the aggregate (450) of patients' information comprising:
i)      calculated patient-specific centers of target zones (40) of prior patients (30) and patient-specific coordinates (48) correlating prior patients' (30) medical scans (102) and locations of the target zones (40) with X, Y and Z axes relative to the patient-specific coordinates (48);
ii)      with and without implanted patient-specific implants (600), three dimensional geometric representations (42) and measurements of prior patients' target zones (40);
iii)      prior patients' metric outputs (408) for making the patient-specific implants (600), medical histories, clinical observations and medical test results;
iv)      surgeons and medical facilities identities and operations dates associated with implantation of the patient-specific implants (600); and
v)      optionally, a registry of government approved safe and effective implants available for implantation into patients (30); and g)      using the processor (406) and the software (404) to process the patient information and aggregate (450) to generate results viewable on one or more displays (206); the results generated by the steps of:
i)      generating a first set of metric outputs (408) relative to the the current patient's (30) target zone (40), a patient-specific coordinate (48) correlating the one or more medical scans (102) and a location of the target zone (40) with X, Y and Z axes associated with the patient-specific coordinate (48) and one or more three dimensional geometric representations (42) providing precise measurements of the target zone (40) and the first set of metric outputs (408) and physician options for selecting the patient-specific implant (600) for manufacture; the physician options including making the patient-specific implant (600) according to one of the first set metric outputs (408), wherein at least one of the first set of metric outputs comprises at least two segments; or
ii)      generating a second set of metric outputs (408) relative to the aggregate (450) and the first set of metric outputs (408), wherein the physician options include making the patient-specific implant (600) according to one of either the first set or second set of metric outputs (408); and
iii)      transferring a physician approved metric selected from the first set of metric outputs (408) and/or the second set of metric outputs (408) to the manufacturing apparatus (500); the physician approved metric controlling manufacture of the patient-specific implant (600) comprising one or more biocompatible substances; and
iv)      optionally, a physical model of the target zone (40).

FIG 50

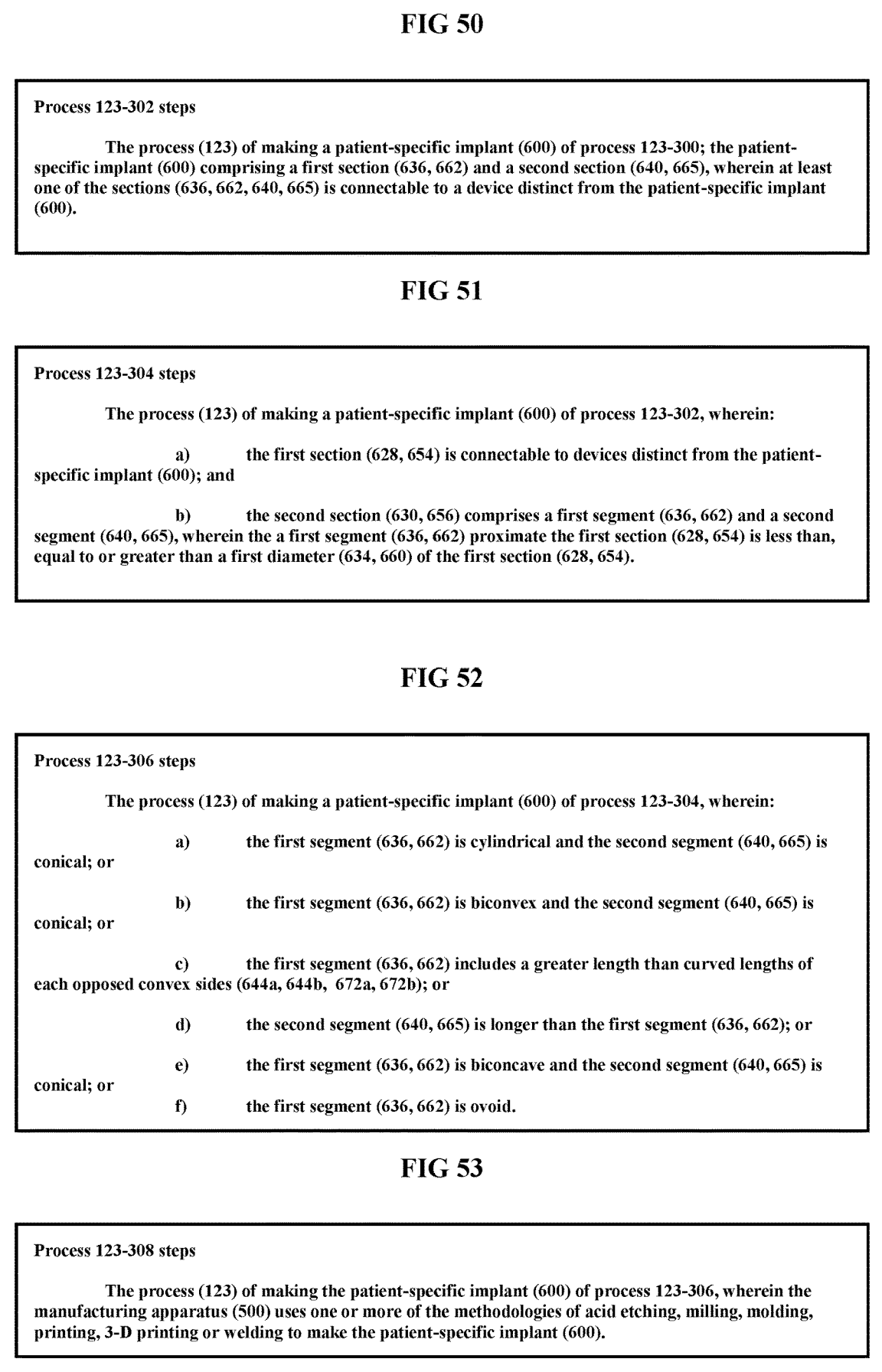

Process 123-302 steps

The process (123) of making a patient-specific implant (600) of process 123-300; the patient-specific implant (600) comprising a first section (636, 662) and a second section (640, 665), wherein at least one of the sections (636, 662, 640, 665) is connectable to a device distinct from the patient-specific implant (600).

FIG 51

Process 123-304 steps

The process (123) of making a patient-specific implant (600) of process 123-302, wherein:

a)      the first section (628, 654) is connectable to devices distinct from the patient-specific implant (600); and b)      the second section (630, 656) comprises a first segment (636, 662) and a second segment (640, 665), wherein the a first segment (636, 662) proximate the first section (628, 654) is less than, equal to or greater than a first diameter (634, 660) of the first section (628, 654).

FIG 52

Process 123-306 steps

The process (123) of making a patient-specific implant (600) of process 123-304, wherein:

a)      the first segment (636, 662) is cylindrical and the second segment (640, 665) is conical; or b)      the first segment (636, 662) is biconvex and the second segment (640, 665) is conical; or c)      the first segment (636, 662) includes a greater length than curved lengths of each opposed convex sides (644a, 644b, 672a, 672b); or d)      the second segment (640, 665) is longer than the first segment (636, 662); or e)      the first segment (636, 662) is biconcave and the second segment (640, 665) is conical; or f)      the first segment (636, 662) is ovoid.

FIG 53

Process 123-308 steps

The process (123) of making the patient-specific implant (600) of process 123-306, wherein the manufacturing apparatus (500) uses one or more of the methodologies of acid etching, milling, molding, printing, 3-D printing or welding to make the patient-specific implant (600).

FIG 54

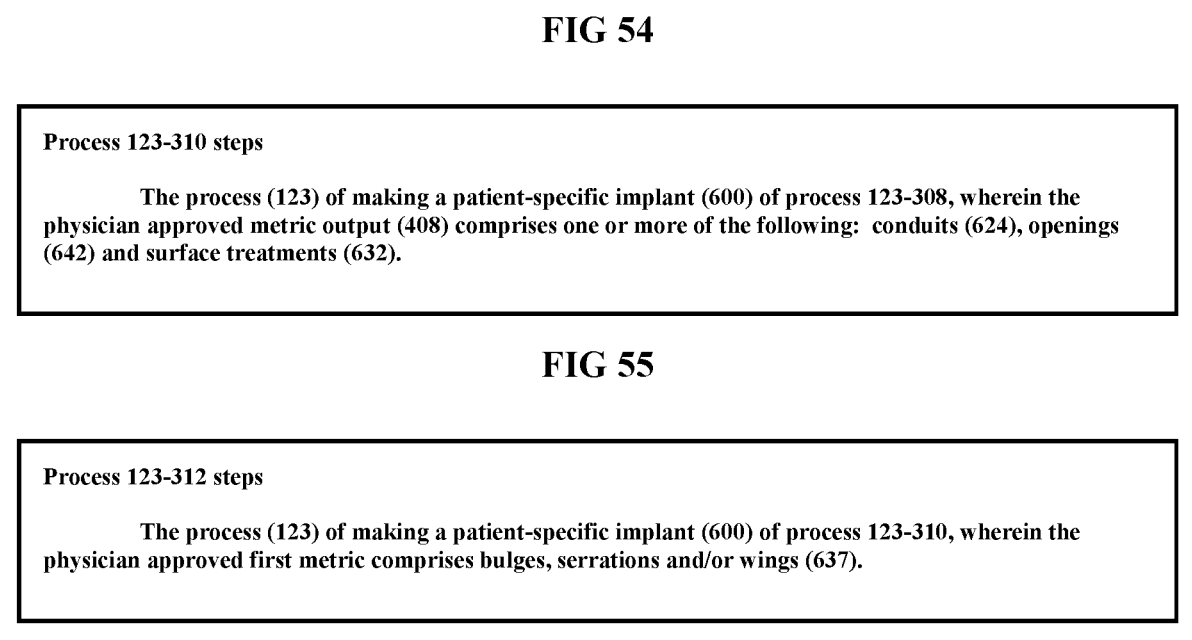

Process 123-310 steps

The process (123) of making a patient-specific implant (600) of process 123-308, wherein the physician approved metric output (408) comprises one or more of the following: conduits (624), openings (642) and surface treatments (632).

FIG 55

Process 123-312 steps

The process (123) of making a patient-specific implant (600) of process 123-310, wherein the physician approved first metric comprises bulges, serrations and/or wings (637).

COMPUTERIZED PROCESS FOR MAKING A PATIENT-SPECIFIC IMPLANT

PRIORITY

Applicant claims the benefit of U.S. Provisional Application No. 63/310,189, filed Feb. 15, 2022 and U.S. Provisional Application 63/317,041, filed Mar. 3, 2022.

BACKGROUND OF THE INVENTION

A. Field of the Invention

Among other things, the present invention uses a process to make a patient-specific implant for one or more target zones within bone. Fixation or other types of implants can be manufactured by the current process.

B. Description of the Previous Art

In the field of spinal surgery, prolonged bedrest in the supine position was the initial treatment for patients with unstable spinal conditions. Pain and the possibility of paralysis forced patients to lie still in bed for months to years at a time. This activity restriction, of not even being able to sit up in bed, was accompanied by increased rates of pneumonia, psychiatric problems and skin ulcerations. Subsequently, cast and brace stabilization of the spine allowed for earlier patient mobilization. External braces allowed patients to sit up and stand within weeks of their injury. Unfortunately, the length of time patients could sit or stand up was limited. Still, early mobilization via external bracing reduced the treatment complication rate and improved the overall success rate.

Internal bracing with spinal instrumentation, specifically constructs using pedicle screws, further reduced the treatment area to be immobilized and provided increased stability within that area. The increased stability provided by pedicle screw instrumentation optimized the environment for healing and significantly reduced the pain. Patients were seen to heal faster and with less pain. Unfortunately, the implantation of screws in and around the spine can damage nearby nerves, blood vessels and bones. Spinal implants which loosen often become painful, fail to provide sufficient stability for healing to occur, and frequently require surgical revision.

Iatrogenic fracture, neurovascular complication, and construct loosening rates are so high in patients with osteoporosis that the surgical treatment option for spinal stabilization is avoided. The quality and quantity of osteoporotic cancellous bone is so poor that the holding power or pullout strength of a pedicle screw is solely dependent upon thread engagement of the subcortical bone within the pedicle. The cancellous bone inside the pedicle and vertebral body do not appreciably change a pedicle screw's fixation strength. When surgeons use larger diameter screws, the threads often cut through the walls of the pedicle and the risk of neurovascular injury increases. Even smaller diameter screws placed with a suboptimal insertion trajectory can breech the pedicle wall and cause a neurovascular injury. Toggle during screw insertion, which is significantly easier in osteoporotic bone, can alter the trajectory of the screw and result in a complication.

Any discussion of references cited in this Description of the Previous Art merely summarizes the disclosures of the cited references and Applicant makes no admission that any cited reference or portion thereof is relevant prior art.

Applicant reserves the right to challenge the accuracy, relevancy and veracity of the cited references.

References that may indicate a state-of-the-art for the current invention include: 1) US Published Patent Application 20150223939—Miles et al. discloses a method incorporating computer-implemented steps, a computing device and a computer readable storage medium for developing manufacturing parameters for manufacturing an orthopaedic implant; 2) US Published Patent Application 20140081400—Azernikov et al discloses semi-automatic customization of plates for internal fracture fixation; 3) US Published Patent Application 20180353299—Wei discloses 3D printing of mesh implants for bone delivery; 4) US Published Patent Application 20200129296—Chary et al. discloses implantable device for temporomandibular joint and method of production thereof; 5) U.S. Pat. No. 6,532,299—Sachdeva et al. discloses a system and method for mapping a surface; 6) US Published Patent Application 20080275558—Clifford et al. discloses extra-articular implantable mechanical energy absorbing systems and implantation method; 7) US Published Patent Application 20190321193—Casey et al. discloses systems and methods for orthopedic implantation fixation; 8) U.S. Pat. No. 10,799,295—Tjon discloses computer-aided design and preparation of bone graft; 9) US Published Patent Application 20040015327—Sachdeva et al discloses a unified workstation for virtual craniofacial diagnosis, treatment planning and therapeutics; 10) US Published Patent Application 20200170802—Casey discloses systems and methods for orthopedic implants; 11) US Published Patent Application 20190167435—Cordonnier discloses systems and methods for multi-planar orthopedic alignment; 12) US Published Patent Application 20220039965—Casey et al. discloses patient-specific artificial discs, implants and associated systems and methods; 13) US Published Patent Application 20180271661—Kamer et al. discloses method for manufacturing an auxiliary device suitable for the manufacture of a patient customized implant; US Published Patent Application 20210053291—Bouvier et al. discloses method for manufacturing a complex substitute object from a real object; 15) U.S. Pat. No. 7,993,347—Michlelson discloses a guard for use in performing human interbody surgery; 16) US Published Patent Application 20090312763—McCormack et al. discloses facet joint implants and delivery tools; 17) U.S. Pat. No. 8,012,186—Pham et al. discloses a uniplanar screw; 18) U.S. Pat. No. 8,764,804—Rezach discloses a bone fastener and methods of use; 19) U.S. Pat. No. 9,826,986—Donner et al. discloses systems for and methods of preparing a sacroiliac joint for fusion; and 20) US Published Patent Application 20150250518—Chirico et al. discloses implantable devices and methods for treating micro-architecture deterioration of bone tissue.

SUMMARY OF THE INVENTION

The present invention involves a process of making unique spinal fixation devices and generating reports related to those devices. A simplistic representation of the current process is: scanning the target zone that will receive the implant, transforming the scans of the target zones into metrics for making the patient-specific implants and using the metrics to control the making of the patient-specific implant for the patient's target zone. More often than not, it is expected that the preoperative, operative and postoperative medical assessments of the patient, scanning of the target zone, creation of the metrics for making the patient-specific implant, generation of the reports related to the patient-specific implants, the manufacture of the patient-specific implant and the implantation of the patient-specific implant will occur at locations distinct from each other. It is anticipated that the present process of making a patient-specific implant for a patient has the annual worldwide capability to create millions of patient-specific spinal implants and reports.

The present process meets the long felt but unfulfilled need of manufacturing a patient-specific implant tailored specifically for the dimensions of the patient's target zone with consideration given to the physiological conditions in the target zone and the medical conditions of the patient. Along with providing a patient-specific implant, the current process can generate a model of the target zone, reports for the benefit of patients, medical personnel, insurers, hospitals, and manufacturers. One report can detail the advantages and disadvantages of several patient-specific implant options during the pre-operative period. Another report can provide technical guidance during the surgical procedure. And other reports can suggest rehabilitation protocols during the post-operative period. Software associated with the current process of making a patient-specific implant can utilize the cumulative data from all previously implanted patient-specific devices to increase the probability of a successful patient outcome for all subsequent patient-specific device implantations.

Currently, surgeons use prefabricated standard-sized generic implants. Size discrepancies between the implant and target zone can result in patient injury. By way of illustration, prior art standard-sized cylindrical corpectomy cages are manufactured in 10.0 millimeter length increments and three diameters for all cases in which the length of the corpectomy trough, or target zone, is greater than 30 millimeters. Thus, if a corpectomy cavity is 45 millimeters in height, 15 millimeters in width and 14 millimeters in depth, then all prior art standard-sized cylindrical cages 40 millimeters in height or less would not be useful or utilized.

The surgeon has three options available for implantation of the cylindrical cage 12 millimeters in diameter and 50 millimeters in length. The first option involves enlarging the corpectomy cavity. The surgeon can use a spreading device, in combination with the chemical paralysis of the paraspinal muscles during surgery, to separate the endplates an additional 5 millimeters. In addition to stretching the adjacent muscles, ligaments and capsules, the exiting neurovascular structures would also be stretched 5 millimeters. Most surgeons avoid this option. Stretching a nerve can result in a neurapraxic or paralytic injury. When the chemical paralysis wears off, the additional compressive forces on the oversized implant can result in either device expulsion or fracture of a vertebral endplate. The unrelenting stretch of capsules and ligaments may also result in neck stiffness and pain. The second option of enlarging the corpectomy trough involves removing an additional 5×15×14 millimeters of bone. Removal of even one cortical endplate can result in a loose implant shortly after surgery. The cancellous bone inside the vertebral body can collapse when positioned next to a metal implant. The third option involves shortening the 50 millimeter prior art cylindrical cage by 5 millimeters. Even though the US Food and Drug Administration recommends that the physical properties of a premanufactured implant not be altered, this is the option most often chosen. Reducing the height of a prior art standard-sized implant can result in sharp edges that can pierce the vertebral endplates or create microfractures, minor problems compared to paralysis or chronic pain.

Patient-specific spinal implants represent an improvement in spinal surgery. Biomechanical and biological stabilization provided by the use of patient-specific implants will optimize the environment for healing over a longer period of time, reduce the surgical complication rate, and increase the outcome success rate as compared to prior art implants.

It is the novel and unique interaction of these simple elements which creates the processes within the ambit of the present invention. Pursuant to Title 35 of the United States Code, descriptions of preferred embodiments follow. However, it is to be understood that the best mode descriptions do not limit the scope of the present invention.

BRIEF DESCRIPTION OF THE DRAWINGS

FIG. 3 is an axial Z-plane view of L3 vertebra (923) of FIG. 2 that references coronal slices C1 and C2.

FIGS. 4a-4c show prior art pedicle screw (666) traversing a first target zone (40) and threadless patient-specific pedicle fixation device (series 600, 620. 650, 690) traversing a second target zone (40). The C1 representation corresponds to the coronal slice near the entrance to the pedicle. The C2 representation corresponds to the area within the pedicle (902) with the smallest circumference.

FIGS. 26a-26f illustrate patient specific implants that can be manufactured by process (123).

FIGS. 27a-27j illustrate patient specific implants that can be manufactured by process (123).

FIGS. 31-55 illustrate steps associated with process (123) of making a patient-specific implant.

DESCRIPTION OF THE PREFERRED PROCESS (123) AND PHYSICAL EMBODIMENTS

Figure 1:
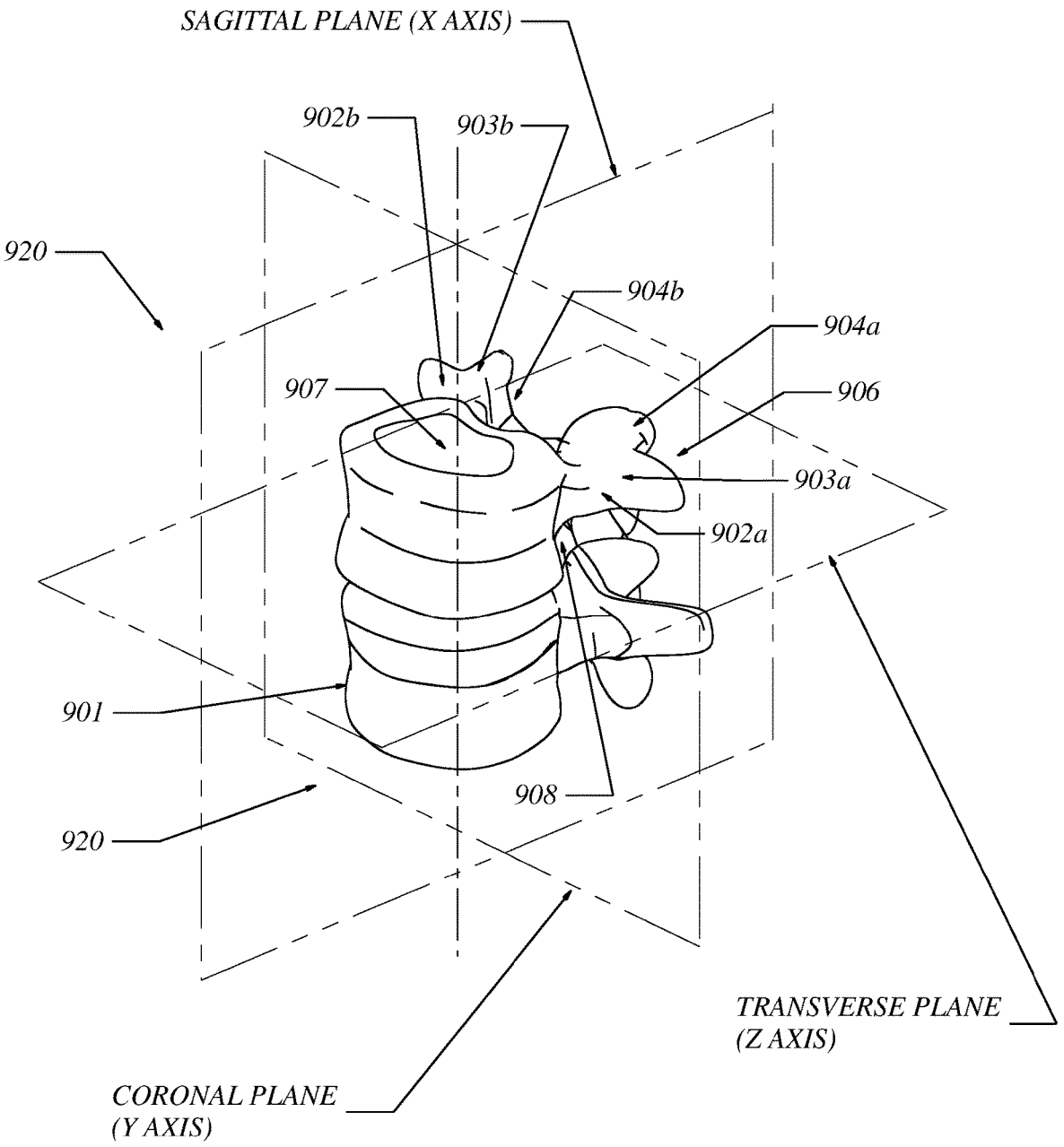
FIG. 1 is a representation of sagittal (X-axis), coronal (Y-axis) and transverse planes (Z-axis) of a spinal segment.

Although the disclosure hereof is detailed to enable those skilled in the art to utilize the process (123) and resulting patient specific implants, the embodiments published herein merely exemplify select patient specific implants.

As used herein, whether identified as singular or plural, implant (600), screw (600), patient-specific spinal fixation device (600), pedicle fixation device (600), patient-specific fixation device (600) are spinal implants made by the current process (123) of making a patient-specific implant (600). As used herein, reference number (600) can reference a patient-specific implant (620, 650, 690) or any other patient-specific implant manufactured by the current process (123) of making a patient-specific implant (600). Any reference to process (123) also means the current process (123) of making a patient-specific implant (600).

As used herein, with regard to vertebra (920): each vertebra (920) has body (901), two pedicles (902a, 902b), two transverse processes (903a, 903b), two mammillary processes (904a, 904b), two lamina (905a, 905b), and one spinous process (906). Depending on the context of the sentence, reference numbers (902, 902a, 902b) refer to one or more pedicles; reference numbers (904, 904a, 904b) refer to one or more mammillary processes; and reference numbers (905, 905a, 905b) refer to one or more lamina.

In the most general sense, the present invention is a process (123) of making a patient-specific pedicle fixation device (600) for a target zone (40) within the patient's (30) vertebra (920). Preferred embodiments of the pedicle fixation device (600) can have four distinct regions. First region (616) guides the pedicle fixation device (600) into its desired location. First Region (616) has a blunt leading edge in front and connects posteriorly to second region (626p). The respective heights and respective widths of the patient-specific fixation device (600) in first region (616) are less than any height or width in second region (626p). The patient-specific pedicle fixation device (600) in second region (626p) can have dimensions that maximize surface contact area (602) with the geometric dimensions (42) of target zone (40) and the subcortical bone within the pedicle (902). Second region (626p) is connected to first region (616) and third region (636p). Third region (636p) corresponds to the area in between pedicle (902) and the mammillary process (904). Wings, bulges and other process (123) metric output (408) customized features (637) can be added to third region (636p). Process (123) metric output (408) can make bends or curves in third region (636p); the bends or curves can be relative to the shared midlines (M1-M1) of the third region (636p) and fourth region (646) and the shared midlines (M-M) of first region (616) and second region (626p). In select preferred embodiments of the current patient-specific implant (600), shared midlines (M1-M1) of the third region (636p) and fourth region (646) are offset of up to about 45 degrees from the shared midlines (M-M) of first region (616) and second region (626p) to create an angled patient-specific implant (600). The angled patient-specific implant (600) can improve ease of interconnection with spinal devices distinct from patient-specific implant (600). Fourth region (646) connects with third region (636p). Fourth region is connectable to devices distinct from patient-specific fixation device (600). Fourth region (646) can be connected with a post (639) to accommodate side loading connectors or a tulip head (not shown) to serve as a top loading connector. Among the plethora of patient-specific pedicle fixation devices (600) that could be made by the current process (123), select examples follow.

Example 1

The current process (123) collects, stores, analyzes and synthesizes three dimensional geographic representations (42) associated with patient's (30) target zones (40), patient-specific fixation devices (600), and records of clinical outcomes. The patient-specific medical implants (600) and the reports (425-427) created from this process (123) can increase the likelihood of a successful treatment outcome as compared to similar surgeries using prior-art implants (666). The process (123) can result in a patient-specific threaded implant (600) with physical dimensions that better approximate the three dimensional geometry of the target zone (40).

By way of illustration, when the fifth lumbar (L5) vertebra (925) and the first sacral (S1) vertebra (926) are to be surgically coupled, the identified target zones (40) will extend from the mammillary process (904), through the pedicle (902), and into the vertebral body (901). The millimeter dimensions of the pedicles (902) in height (Ht), width (Wt) and length (L), along with the medial-lateral (ML) insertion angles and overall pedicle shape as determined by a CT scan (102) are as follows:

| Pedicle | (C1) Ht/Wt | (C2) Ht/Wt | (C3)* Ht/Wt | L | ML** | Pedicle Shape |
|---|---|---|---|---|---|---|
| Right L5 | 18; 20 | 10; 10 | 10; 10 | 20 | 30 | Tubular round |
| Left L5 | 18; 20 | 14; 14 | 10, 10 | 20 | 30 | Round conical |
| Right S1 | 20; 25 | 20; 15 | 15; 10 | 15 | 40 | Oval conical |
| Left S1 | 20; 25 | 20; 15 | 18; 10 | 15 | 40 | Oblong conical |

*C1 is the area measured in the coronal plane near the entry point of the pedicle (902). C2 is the area measured in the coronal plane at the midpoint of the pedicle (902). C3 is the smallest coronal plane measurement within the pedicle (902). The location of C3 varies but it is usually between the pedicle's (902) midpoint and the vertebral body (901).
**ML is medial-lateral angulation using the spinous process (906) as a midline vertical, zero reference relative to the channel of the pedicle (902).

Figures 4, 4A, 4B, 4C:
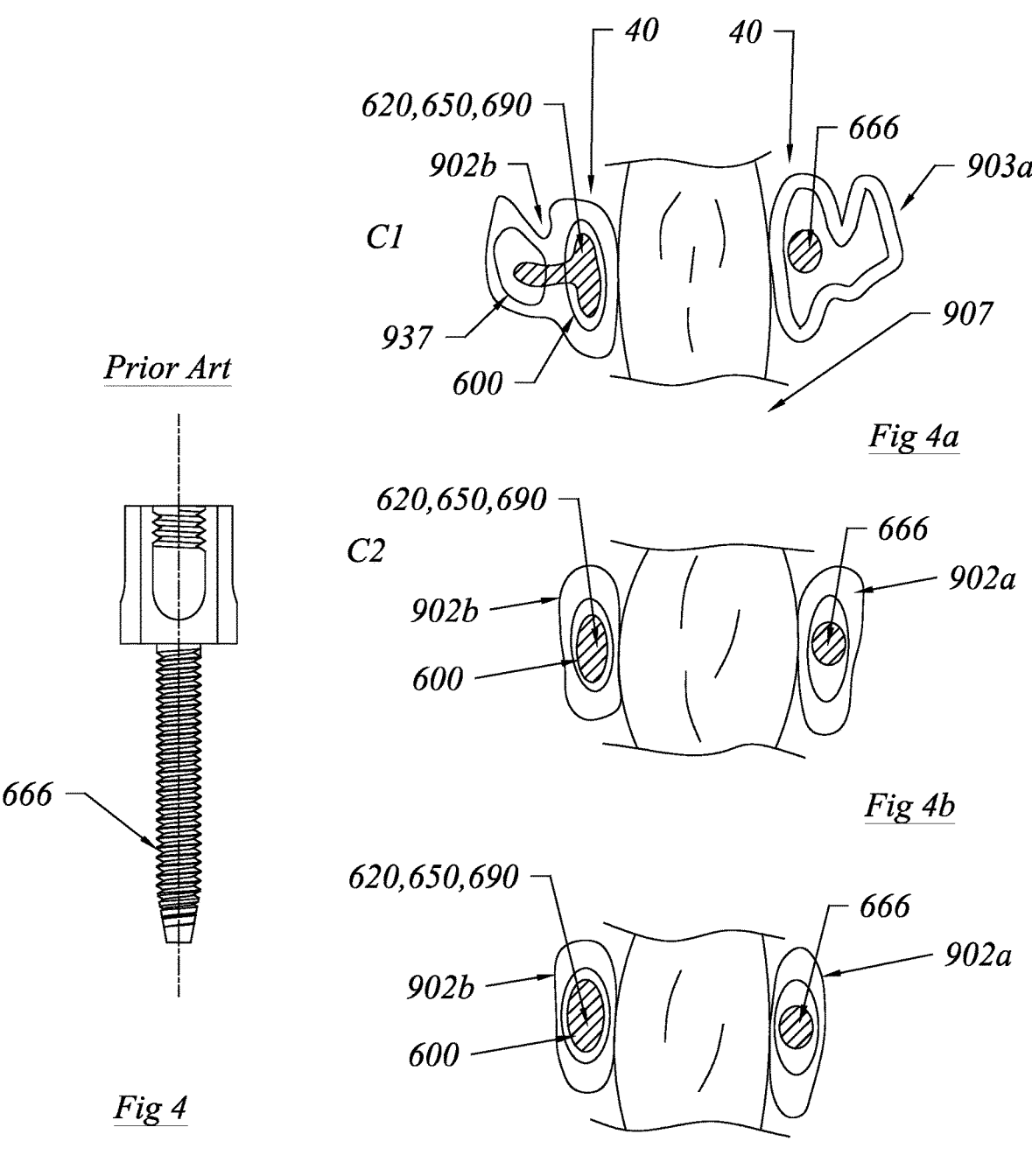
FIG. 4 is a depiction of a prior art screw portrayed in FIGS. 4a-4c.
FIGS. 4a-4c are two dimensional Y-axis portrayals of C1 and C2 slices of the L3 vertebra (923) of FIG. 3.

A skilled surgeon would probably implant round prior art screws (666) with an outer thread diameter of 9.5 millimeters for all four target zones using a freehand insertion technique. The implant's (666) fill of the pedicle (902) is illustrated in FIG. 4. The limiting geometric factors are the pedicle's 10 millimeter widths and the prefabricated screw's 0.5 millimeter diameter increments. The L5 pedicle screws (666) would have 20 millimeters of threads within their pedicles (902); the S1 screws (666), 15 millimeters. A round prior art pedicle screw (666), 9.5 millimeters in diameter, placed into the right L5 pedicle (902) would have better biomechanical holding power than the 9.5 millimeter prior art pedicle screw (666) placed into the left L5 pedicle (902). The threads of the prior art screw (666) on the right would engage more subcortical bone than those on the left. The left S1 prior art pedicle screw (666), having the worst holding power of all four screws, is most likely to loosen, initiating a series of events leading to a poor surgical outcome. Prior art pedicle screws (666) larger than 10 millimeters in diameter could either cut through the pedicle (902) wall or cause a fracture. Either complication can increase the risk of a neurovascular injury, a construct failure, and an outcome failure. As prior art screws (666) decrease in diameter below 9.0 millimeters, the risk of screw loosening increases, especially in patients with osteoporosis. As the screws (666) or the destabilized spinal segment start to move relative to one another, the risk of pain and an unsuccessful outcome increase.

A surgeon using computerized navigation (800) assistance could use round prefabricated screws (666) with a 10 millimeter outer diameter for placement of for all four target zones (40). The navigation system (800) can ensure 30 degrees of medial angulation at L5 and 40 degrees of medial angulation at S1. The surgeon using prior art conically-shaped pedicle screws (666) would appreciate greater holding power of the bone in the left L5 and both S1 pedicles as compared to round prior art screws (666) in those same pedicles. A conical shaped patient-specific pedicle fixation device (600) for the left L5 pedicle would have an outer thread diameter taper from 18 millimeters at the pedicle's entrance (C1) to 14 millimeters at the pedicle's midpoint (C2) then to 10 millimeters at C3. The tapers could be smooth or abrupt depending on patient (30) anatomy. The process (123) can accommodate both smooth and abrupt tapers. The patient-specific conical pedicle screws (600) for the S1 pedicles (902) would taper from a millimeter outer diameter at the pedicle's entrance (C1) to 15 millimeters at pedicle midpoint (C2) and to 10 millimeters from C3 to the entrance to the vertebral body (901). These patient-specific conical screw (600) tapers would be steeper than those required for the patient-specific conical pedicle screws (600) for L5. As the contact surface area of the screw threads and the subcortical bone within the pedicles (902) increases, so does construct stability and durability.

Example 2

The process (123) can create threaded or threadless implants with physical dimensions approximating the three dimensional geometry of the target zone (40). As demonstrated in Example 1, conical shaped patient-specific threaded implants (600) can be manufactured to better approximate the geometry of the target zone (40) as compared to prior art prefabricated conical pedicle screws (666). Threadless patient-specific pedicle fixation devices (600) can approximate the geometry of the target zone (42) even better than threaded patient-specific implants (600) with a conical shaft.

Threadless implants (600) have at least five significant advantages when compared to threaded implants. Most pedicles (902) are oval when viewed in the coronal plane and conical when viewed in the sagittal plane. Thus, the circumferential engagement of round prior art threaded pedicle screws (666) by strong subcortical bone is limited to a small area near the pedicle's (902) exit (similar to that shown in FIG. 4, area C3 on the left). Biomechanically, the loads transmitted from L5 (925) to S1 (926) in a fusion construct are concentrated to an area near the entrance of the S1 pedicle (similar to that shown in FIG. 4 area C1 on the left). In patients with normal bone densities, the cancellous bone within the pedicle (902) can prevent toggle. In patients with osteoporosis, vertical motion at the entrance to the S1 pedicle (area C1), frequently occurs. A majority of L5-S1 construct failures occur by either screw loosening at their fixation point near the S1 pedicle's exit point (area C3) or by S1 screw fracture at a point near the pedicle's entrance point (area C1).

Surgical success occurs when the spinal level fuses or the fractured bone heals before the level destabilizes. The biomechanical fixation strength of constructs made with highly polished, prior art pedicle screws (666), only weaken with time and applied stresses. For patients with osteoporosis, the time interval between implantation and destabilization is short and fewer applied stresses of lower magnitude are required for an outcome failure to occur. Construct loosening is also accelerated when a conical pedicle screw is turned counterclockwise.

Placement of threadless patient-specific implants (600) places fewer technical demands on the surgeon than placement of prefabricated threaded pedicle screws (666). Threadless patient-specific implants (600) can be gently tapped into position one millimeter at a time. The tapping direction is parallel to the channel of the target zone (40). A sudden increase in the amount of force required to advance the implant would indicate that the implant's trajectory is either suboptimal or that the implant is completely inserted. Threadless patient-specific implants (600) advanced with a suboptimal trajectory, by design, can autocorrect by bouncing off the subcortical pedicle wall.

The tapping force required to advance a threadless implant (600) forward is smaller and easier to calibrate than those required to advance a comparably sized threaded screw. The surgeon must simultaneously apply a rotational force perpendicular to the longitudinal axis of pedicle (902) and an advancement force parallel to the longitudinal axis of the pedicle (902) when inserting threaded screws. When the torsional and advancement forces are not perfectly coordinated with the anatomic and physiologic properties of target zone (40), toggle and/or misdirection of the threaded screw can occur. Toggle during threaded screw insertion may facilitate threads cutting through the pedicle (902) wall, fracture of the pedicle (902) wall, or placement of a loose pedicle screw. Toggle always increases the risk of neuro-vascular injury, construct failure and outcome failure.

Figure 2:
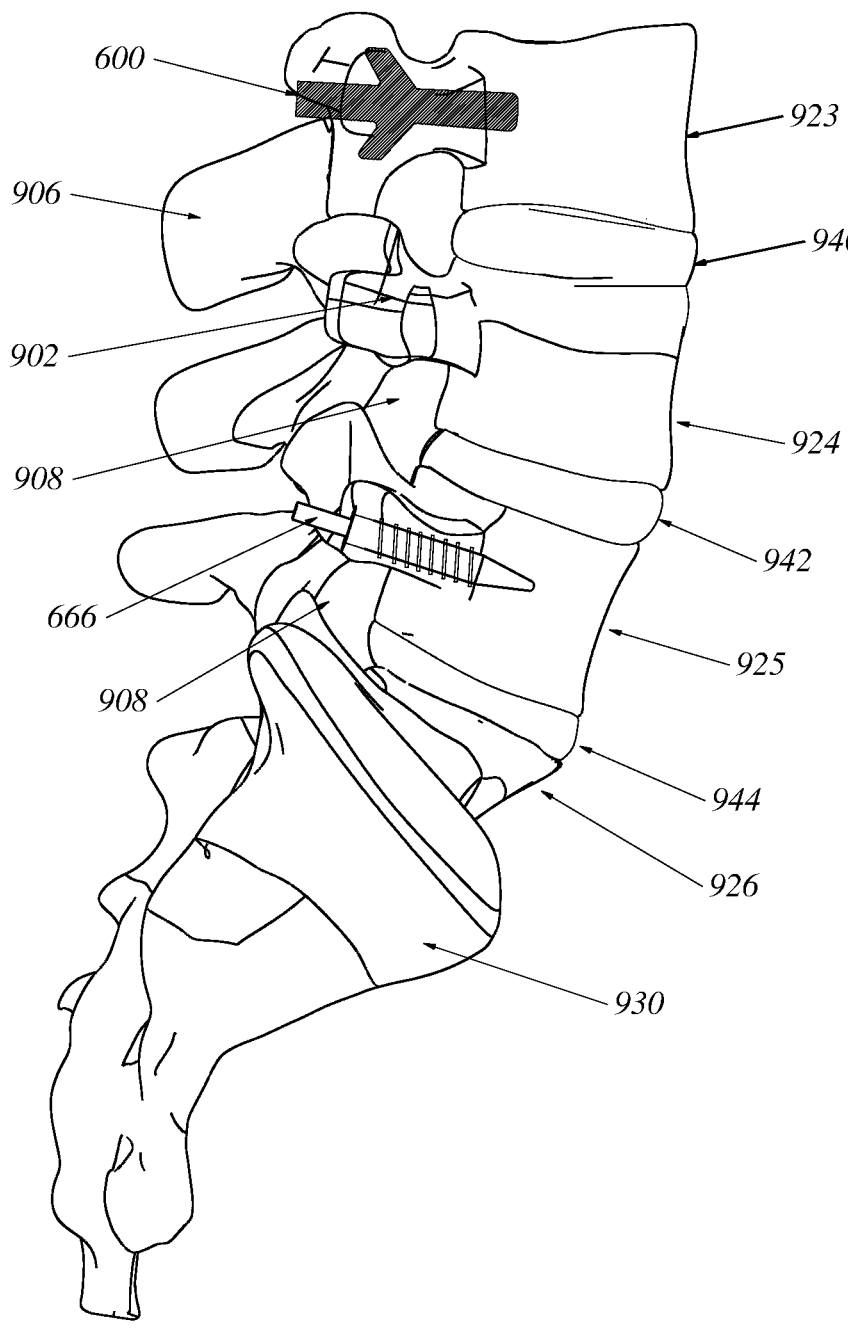
FIG. 2 is a two dimensional sagittal X-plane portrayal of the spine, from the third lumbar (L3) vertebra (923) to the sacrum (930) including disks (940; L3-4), (942; L4-5), (944; L5-S).

Threadless patient-specific pedicle fixation devices (600) allow for modifications which can improve safety during implantation, optimize the final implant location, and improve biomechanical features of the construct. In patients with osteoporosis the cancellous bone inside the vertebral body (901) contributes only minimally to construct stability. Most surgeons use the longest, largest pitched screw possible to (theoretically) maximize the biomechanical factors contributing to fixation strength. The increased outer diameter of the threads, however, increases the risk of a neuro-vascular injury. Whereas a prefabricated threaded pedicle screw (666) might need to be 70 millimeters in length, a threadless pedicle fixation device (600) for the same target zone might only need to be 45 millimeters in total length (FIGS. 2 and 6). The patient-specific threadless implant (600) can terminate five to seven millimeters inside the vertebral body (901). Patient-specific threadless implants (600) can also have bulges, serrations, or wings (637) that would prevent over-insertion, optimize the juxtaposition of its porous ingrowth surface with the pedicle's (902) subcortical bone, and increase the surface area over which transmitted loads are dissipated (FIGS. 2-6).

FIGS. 4a-4c show prior art pedicle screw (666) traversing a first target zone (40) and threadless patient-specific pedicle fixation device (series 600, 620. 650, 690) traversing a second target zone (40).

By way of illustration, in a spinal surgery where the fifth lumbar (L5) vertebra (925) and the first sacral (51) vertebra (926) are to be fused. The millimeter dimensions of the L5 and S1 pedicles (902) in height (Ht), width (Wt) and length (L), along with the medial-lateral (ML) insertion angles and overall pedicle shape could be as follows:

| Pedicle | (C1) Ht/Wt | (C2) Ht/Wt | (C3) Ht/Wt | L | ML | Pedicle Shape |
|---|---|---|---|---|---|---|
| Right L5 | 18; 20 | 10; 10 | 10; 10 | 20 | 30 | Tubular round |
| Left L5 | 18; 20 | 14; 14 | 10, 10 | 20 | 30 | Round conical |
| Right S1 | 20; 25 | 20; 15 | 15; 10 | 15 | 40 | Oval conical |
| Left S1 | 20; 25 | 20; 15 | 18; 10 | 15 | 40 | Oblong conical |

The surgeon can use threadless patient-specific implants (600) to maximize the contact surface area between the pedicle's (902) subcortical bone and the patient-specific implant (600) shown in FIGS. 4c and 4d. The threadless patient-specific dimensions would be as follows:

| Pedicle | (C1) Ht/Wt | (C2) Ht/Wt | (C3) Ht/Wt L | ML | Pedicle Shape |
|---|---|---|---|---|---|
| Right L5 | 17.8; 19.8 | 9.8, 9.8 | 10, 10 20 | 30 | Tubular round |
| Left L5 | 17.8; 19.8 | 13.8; 13.8 | 10, 10 20 | 30 | Round conical |
| Right S1 | 19.8; 24.8 | 19.8; 14.8 | 15, 10 15 | 40 | Oval conical |
| Left S1 | 19.8; 24.8 | 19.8; 14.8 | 18, 10 15 | 40 | Oblong conical |

Patient-specific threadless implants (600) can achieve immediate biomechanical fixation strength from their geometric compatibility in region 2 (626p) with the target zone's (40) subcortical bone in pedicle (902). Long-term biological stability can be enhanced by bone ingrowth into patient-specific spinal implant's (600) porous ingrowth surface (638p). As the surface contact area between the patient-specific spinal implant (600) and the pedicle's (902) subcortical bone within the target zone (40) increases, there is a greater probability that bone will grow into and stabilize the patient-specific spinal implant (600).

Threadless patient-specific spinal fixation devices (600) can also be manufactured with safety features in third region (636p). A circumferential enlargement or wing (637) might limit the depth of implant (600) insertion as illustrated in FIGS. 4c-6. The additional contact surface area near the pedicle's entrance (area C1) might better disperse loads transmitted across the fixation construct. Dispersing loads over a greater surface area can reduce the possibility of implant loosening. The biomechanical strength of a threadless porous ingrowth patient-specific implant (600) can increase over time. Fixation strength increase as the amount of subcortical bone inside the pedicle (902) grows into the porous ingrowth surface (638p) of the patient-specific pedicle fixation device's (600) second region (626p).

Example 3

Among other things, the process (123) of making a patient-specific spinal fixation device (600) for a patient (30) can create patient-specific implants (600) with physical attributes that allow for safer and easier surgical implantation (FIG. 6).

By way of illustration, consider a spinal surgery where the third lumbar (L3) vertebra (923) through the first sacral (S1) vertebra (926) will be fused. The millimeter dimensions of the right L3, L4, L5 and S1 pedicles in height (Ht), width (Wt) and length (L), along with the medial-lateral (ML) insertion angles are as follows:

| Pedicle | (C1) Ht/Wt | (C2) Ht/Wt | (C3) Ht/Wt | L | ML_ |
|---|---|---|---|---|---|
| L3 | 15; 10 | 12; 10 | 8; 8 | 22 | 10 |
| L4 | 18; 18 | 14; 12 | 10; 8 | 22 | 15 |
| L5 | 18; 20 | 14; 14 | 10; 10 | 20 | 30 |
| S1 | 20; 25 | 20; 15 | 18; 10 | 15 | 40 |

Larger medial-lateral insertion angles can require greater surgical dissection. Skin incisions are longer and muscle dissections are wider with larger medial-lateral insertion angles. Larger dissections are also required for obese patients compared to non-obese patients. Larger dissection areas increase the time required to perform the surgery, the risk of tissue devascularization, and the risk of a post-operative infection. If the surgeon wanted to minimize the dissection, the following patient-specific implants (600) can be made:

| Pedicle | C1 Ht/Wt | C2 Ht/Wt | C3 Ht/Wt L | Degree bend towards midline in region 3 |
|---|---|---|---|---|
| L3 | 14.9; 9.9 | 11.9; 9.9 | 8; 8 22 | 0 |
| L4 | 17.9; 17.9 | 13.9; 11.9 | 10; 8 22 | 5 |
| L5 | 17.9; 19.9 | 13.9; 13.9 | 10; 10 20 | 20 |
| S1 | 19.9; 24.9 | 19.9; 14.9 | 18; 10 15 | 30 |

Less lateral dissection for implantation would be required and the alignment of posts for connection could be improved. The surgeon's request for angled fixation devices might cause the current process (123) to generate a report (425) with the following: (A) threadless implants (600) with a S1 fixation post angled 30 degrees towards the midline have a third region (636p) fracture rate of 15%, a post-operative infection rate of four percent, and an overall success rate of 86%; (B) threadless implants (600) with a S1 fixation post angled 20 degrees towards the midline have a third region (636*p*) fracture rate of 10%, a post-operative infection rate of seven percent, and an overall success rate of 90%; and, (C) threadless implants (600) with a fixation post angled 10 degrees towards the midline or less have a third region (636*p*) fracture rate of 5%, a post-operative infection rate of 12%, and an overall success rate of 88%.

The surgeon might recommend to a patient (30) with previous wound infections that patient-specific implant option (A) be manufactured. If the surgeon was concerned about a third region (636*p*) fracture, due to patient obesity, the surgeon might recommend option (B). If the patient had a significant rotational deformity (scoliosis) of the lumbar spine which was going to be surgically corrected, the surgeon might recommend option (C).

Example 4

The current process (123) of making a patient-specific spinal fixation device (600) for a patient (30) includes a memory (402) storing data associated with a patients' pre-operative target zone(s) and medical history, clinical observations, etc. For example, patients' (30) medical histories including Bone Mineral Density (BMD) can be associated with the patients target zones (40) and implants (600 and 666).

In the above examples, the BMDs of the target zones (40) were assumed to be the same. But each target zone (40) could have had a different BMD. By way of illustration, the L5 pedicles (902) could have had a localized BMD of –1.5 while the BMD of the S1 pedicles (902) could have been –2.4. In accordance with the current process (123) of making a patient-specific spinal fixation device (600), this additional information could change the metric output (408) as follows:

| Pedicle | C1 Ht/Wt | C2 Ht/Wt | C3 Ht/Wt | L | BMD | Metric Output |
|---|---|---|---|---|---|---|
| Right L5 | 17.8; 19.8 | 9.8; 9.8 | 10; 10 | 20 | –1.5 | Unchanged |
| Left L5 | 17.8; 19.8 | 13.8; 13.8 | 10, 10 | 20 | –1.5 | Unchanged |
| Right S1 | 19.8; 24.8 | 19.8; 14.8 | 15; 10 | 15 | –1.5 | Previous output |
| Left S1 | 19.8; 24.8 | 19.8; 14.8 | 18, 10 | 15 | –1.5 | Previous output |
| Right S1 | 19.6; 24.6 | 19.5; 14.5 | 15; 10 | 15 | –2.4 | Updated output |
| Left S1 | 19.6; 24.6 | 19.5; 14.5 | 18; 10 | 15 | –2.4 | Updated output |

In addition to the metric output (408) change at C1 and C2, the report to the surgeon (425) can delineate that the forces needed to impact the threadless patient-specific implants (600) into the S1 (926) will be lower than those needed to insert the patient-specific implants (600) into the L5 (925). During the surgical implantation of the patient-specific implants (600) the surgeon can appreciate a tactile difference between the two levels. If a computerized navigation system (800) is used during surgery, the process' (123) three dimensional geometric representations (42) of the patient's (30) target zone(s) (40) and the physician approved metric output (408) for the implants (600) can be communicated to the computerized navigation system (800). Among other things, process (123) sends commands to navigation system (800) regarding the trajectory angle into the target zone(s) (40), appropriate insertion forces, and depth of insertion details could also be included.

Example 5

As previously indicated, the current process (123) of making a patient-specific spinal fixation device (600) for patient (30) uses memory (402) than can store an aggregate of encrypted and tagged information associated with a patient's target zones (40), implants (600 and 666), and surgeon.

By way of illustration, the patient has a BMD of –3.0 and the subcortical or inner diameter of a round pedicle is 7.0 millimeters. During the process (123) of making a patient-specific implant (600), memory (402) can generate report (425) and a visual three dimensional representation (42) of: (A) a round 6.80 millimeter in diameter threadless implant (600) which will have an iatrogenic pedicle fracture rate of 5%, a post-operative implant loosening rate of 20%, and an overall success rate of 78%; (B) a round 6.90 millimeter in diameter threadless implant (600) which will have an iatrogenic pedicle fracture rate of 10%, a post-operative implant loosening rate of 10%, and an overall success rate of 85%; and, (C) a round 6.95 millimeter in diameter threadless implant (600) which will have an iatrogenic pedicle fracture rate of 20%, a post-operative implant loosening rate of 5%, and an overall success rate of 85%.

The patient (30) and surgeon can discuss the process' (123) generated surgical options (FIG. 7), and select the preferred patient-specific implant (600). The surgeon could explain to the patient that since the patient-specific implants will be inserted freehand, they could approve patient-specific implant option (B). If the surgeon has recently obtained access to a computerized navigation system (800), option (C) could be selected as the risk of iatrogenic fracture with navigation assistance (800) is lower than that stated in report (425).

Example 6

The current process (123) of making a patient-specific pedicle fixation device (600) for a patient (30) can create a patient-specific implant (600) while taking into account a patient's medical history, the patient's surgical history and the medical and surgical histories of all patients currently in the memory (402) database.

Examples of significant medical history include but are not limited to age, weight, body mass index (BMI), gender, bone mineral density (BMD), smoking history, anatomical location of implants, number of implants, navigation system usage, and other variables that might influence postsurgical outcome. Three important variables in predicting the long-term success of staged spinal procedures using porous ingrowth technology are: the patient's current medical condition, the initial postoperative stability of the implant, and the time between the initial implantation and definitive surgical procedure (when the patient-specific spinal implants are coupled together).

By way of illustration, a patient (30) has severe stenosis resulting in neurogenic claudication, a painful dynamic spondylolisthesis, takes prednisone for asthma, and has osteoporosis. Spinal instrumentation is indicated as the spine is already unstable, the dynamic spondylolisthesis. The decompression of the stenosis will further destabilize the spine. By splitting the stabilization part of the procedure from the decompression and fusion part of the procedure into two surgeries, the probability of a long-term successful outcome is increased. The first procedure will involve the percutaneous implantation of the threadless patient-specific implants (600) into their respective target zones (40). This is followed by a 90 to 120 day interval which allows for bone ingrowth into second region (626*p*) of the patient-specific pedicle fixation device (600). Minimal loads are being transferred across the implant-bone interface during this interval, as the implants have not been connected. The biological fixation strength increases as subcortical bone grows into the porous surface (638p) of second region of the patient-specific fixation device (600). When the patient (30) returns for the definitive decompression and fusion procedure the threadless patient-specific implants (600) will have significantly better fixation strength than if the procedure were not staged. The probability of these well fixed threadless patient-specific fixation devices (600) loosening will also be lower than if the procedure were not staged. A surgeon encountering a loose threadless patient-specific fixation device (600) has three options to improve fixation that would not have existed if the procedure were not staged. The first option would be to replace the threadless patient-specific fixation devices (600) with a larger one. The second option would be to instrument additional levels into the fixation construct. The third option would be to use an adhesive, such as polymethylmethacrylate to better secure the device in place.

The patient-specific pedicle fixation devices (600) are coupled at the time of the definitive surgery. Loads now crossing the bone-implant interfaces will be much higher. The time between the initial implantation of a patient-specific implant and the definitive surgical procedure will vary based on medical conditions specific to each patient. Smokers usually require longer intervals to achieve adequate bone ingrowth than non-smokers. Patients taking prednisone usually require longer intervals to achieve adequate bone ingrowth than patients not taking prednisone. And patients with osteoporosis typically require longer intervals to achieve adequate bone ingrowth than patients with normal bone mineral densities. Over time, use of the current process' (123) software (404) and memory (402), can generate improved recommendations regarding the interval between staged procedures and post-operative activities.

Example 7

Among other things, the aggregate (450) of encrypted and tagged information stored in the memory (402) of process (123) of making a patient-specific spinal fixation device (600) for a patient (30) can include: identity of surgeon, the patient-specific fixation device (600) implanted during the surgery, devices utilized in the surgery, length of the surgery, target zones (40) of the surgery, type of surgery, navigation assistance (800) utilized, use of compositions and devices ancillary to implantation of patient-specific implant (600) and postoperative results associated with patient-specific implant (600). Search capabilities of aggregate (450) of encrypted and tagged information associated with the current process (123) of making a patient-specific spinal implant (600) are available. The search capabilities can group information such as identities, postoperative outcomes associated with the surgeons' implantations of the patient-specific implants (600) into patients in view of the patients' (30) past medical histories, current medical observations and/or current medical test results. Generated efficiency reports (426) associated with the outcomes of patient-specific implants (600) can assist in patient care, hospital efficiency, and manufacturing.

By way of illustration, the average time required per patient-specific fixation devices (600) implantation is 20 minutes for the initial 50 procedures, 15 minutes for procedures 51 through 100, and 10 minutes per implantation thereafter. If an efficiency report (426) for a surgeon or hospital showed that the first 50 implantations took 25 minutes and implantations 51-200 took 20 minutes per implant. The surgeon and hospital may benefit from a training course, the purchase of a navigation system (800), or both.

Example 8

Among other things, the process (123) of making a patient-specific pedicle fixation device (600) for a patient (30) can evaluate treatment effects relative to the patient-specific implant (600). As the aggregate (450) of the process' (123) encrypted and tagged information increases, operative and post-operative protocols can undergo modification. Some surgeons might inject iliac crest bone marrow aspirate through the implant (600) to facilitate bone ingrowth. Injections can occur at the time of implantation and at any time thereafter. Educational reports (427) comparing different adjunct medical treatments of patients receiving patient-specific implants (600) made by the current process (123) can be generated. For example, results of patient (30) receiving or not receiving iliac crest bone marrow aspirate injections can be made available through peer review publications.

Example 9

Among other things, the process (123) of making a patient-specific spinal fixation device (600) for a patient (30) may include preoperative and postoperative scans (102) of the target zones (40).

Postoperative scans (102) can provide visual information regarding three dimensional representations (42) of the patient-specific implants (600), including but not limited to, the target zone (40) and placement therein, migration, radiographic loosening, percent bone in-growth, fracture of bone, neurovascular injury, implant fracture, postoperative complications and changes to the implant required because of the patient's medical condition and history. Process' (123) postoperative data added to memory (402) may change the metric output (408) of the next patient-specific implant (600) manufactured.

Example 10

Figure 5:
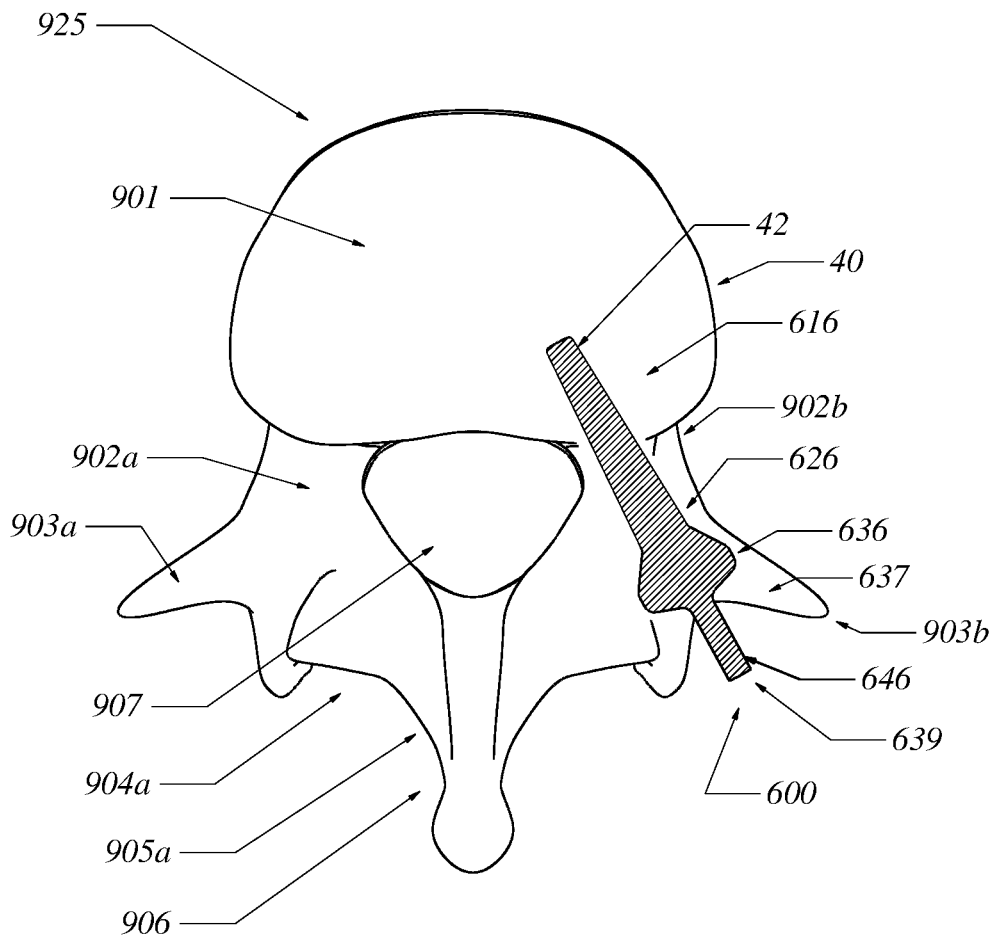
FIG. 5 is a L5 axial plane view of a target zone (40) of L5 vertebra (925).
Figure 6:
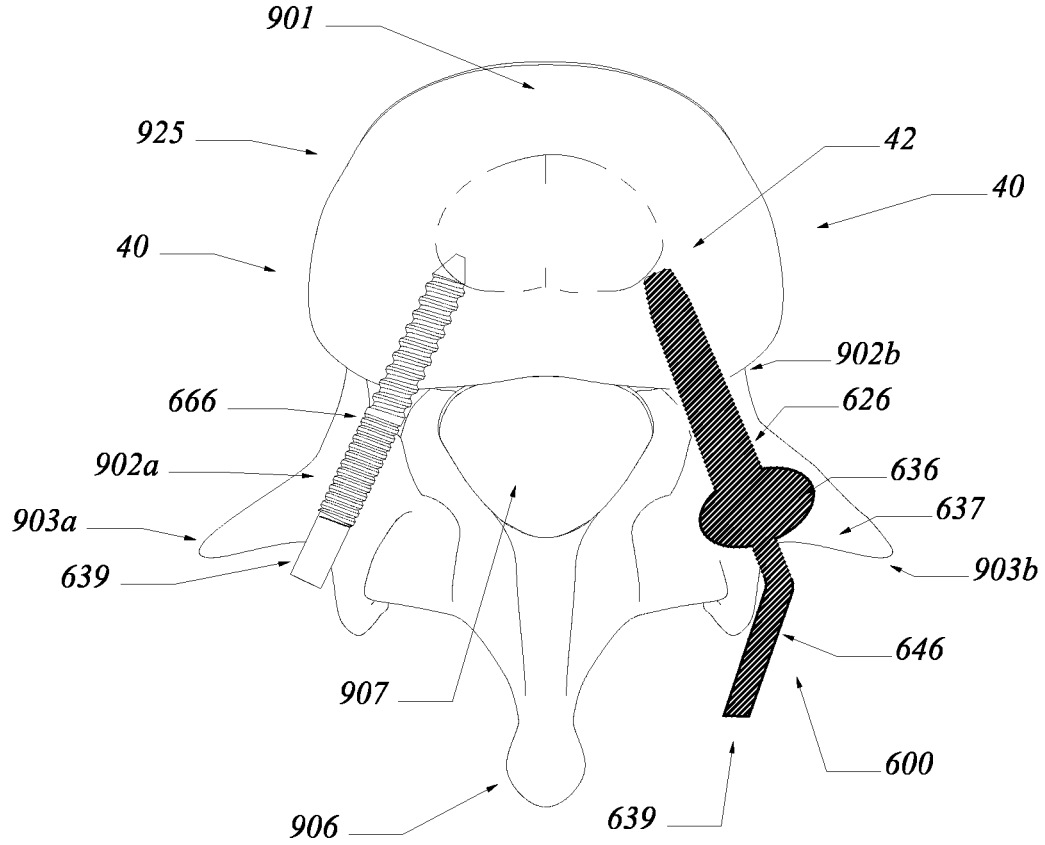
FIG. 6 is a L5 axial plane view of first and second target zones (40) of L5 vertebra (925).

Another advantage of the present process (123) of making a patient-specific spinal fixation device (600) for a patient (30) is that the metric output (408) can create additional structures for patient safety (FIGS. 5 and 6).

By way of illustration, an L5 vertebra (925) has an oval pedicle 10 millimeters in length, 15 millimeters in height, and 11 millimeters in width. The distance from the mammillary process to the entrance of the pedicle in 8 millimeters. The surgeon has 8.0 millimeters of cancellous bone and the cortical bone adjacent to the entry site that may assist with implant stabilization. The current process (123) can make a threadless personalized L5 pedicle fixation device (600) for this target zone (40) with the following four zones. First region (616) has a blunt oval tip 5 millimeters in height and 3 millimeters in width. The tip can expand over a 6 millimeter length to 15 millimeters in height, and 11 millimeters in width at the junction between first region (616) and second region (626p). The patient-specific spinal implant (600) would have the same dimensions, 15 millimeters in height, and 11 millimeters in width, for the entirety of second region (626p). Third region (636p) can have an enlargement to 18 millimeters in height, and 14 millimeters in width for six of its eight millimeters in length. Fourth region (646) can have a 7 millimeter by 15 millimeter highly polished post. Third region (636p) can be made to have an outward side angled at 30 degrees relative to longitudinal axis (X-X) of patient-specific pedicle fixation device (600). These customizable options can be included in a patient-specific report (425) to the surgeon.

FIG. 1 is a representation of sagittal (X-axis), coronal (Y-axis) and transverse planes (Z-axis) of a spinal segment. Among other things, vertebra (920) has a body (901), two pedicles (902a, 902b), two transverse processes (903a, 903b), two mammillary processes (904a, 904b), two lamina (905a, 905b), and one spinous process (906). The central spinal canal (907) contains the spinal cord and cauda equina. The neuroforamin (908a. 908b) allow nerves and blood vessels to enter and exit the spinal canal (907).

Figure 3:
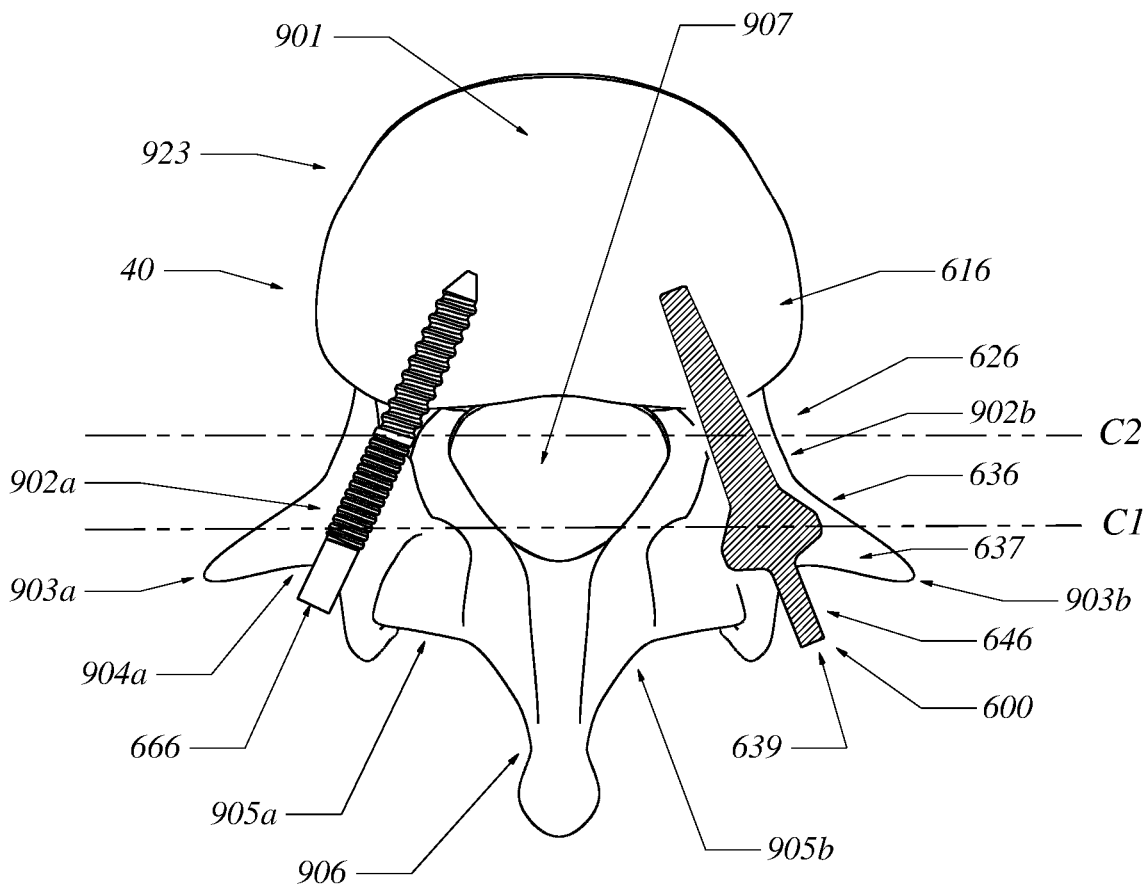
FIG. 3 is a comparative perspective of first and second pedicles portraying traditional threaded pedicle screw (666) inserted into a target zone (40) of the first pedicle and a patient specific implant (600) implanted into a target zone (40) of the second pedicle.

FIGS. 2 and 3 are two dimensional portrayals of a spine. FIG. 2 is a sagittal X-plane portrayal from the third lumbar (L3) vertebra (923) to the sacrum (930) including disks (940; L3-4), (942; L4-5), (944; L5-S1). A patient-specific pedicle fixation device (600) is positioned inside the target zone (40) of L3 (923). A round prior art threaded pedicle screw (666) positioned inside the target zone (40) of L5 (925). Both implants (600, 666) have a leading section inside the vertebral body (901), a middle section within the pedicle (902a, 902b), a section between the pedicle (902a-902b) and the mammillary process (904a-904b) and a section posterior to the mammillary process (904a, 904b) that can connect to other medical devices. Neuroforamin (908) is located beneath each pedicle (902a, 902b). Nerves passing through neuroforamin (908) connect the central nervous system with the peripheral nervous system.

FIG. 3 is an axial Z-plane view of L3 vertebra (923) of FIG. 2 providing reference to coronal slices C1 and C2. A traditional threaded pedicle screw (666) traverses a first target zone (40) and a patient-specific implant traverses a second target zone (40). The spinal canal (907) which houses the spinal cord and cauda equina is medial to the pedicles (902a, 902b). Both devices (600, 666) have a medial-lateral angulation of 7 degrees towards the midline. The threadless patient-specific fixation device (600) has two enlargements or wings (637a, 637b). These customized features can limit the depth of insertion, optimize the alignment of the subcortical bone within the pedicle (902b) with region 2 (626p) of patient-specific fixation device (600), increase the surface area for subcortical bone ingrowth from the transverse process (903b) and lamina (905b), and provide a larger surface area to disperse loads transmitted from adjacent spinal levels.

FIGS. 4a-4b are coronal Y-plane views of the L3 vertebra (923) shown in FIG. 3. A prior art pedicle screw (666) is traversing (C1) on the left sides of FIGS. 4a-4b. A threadless patient-specific pedicle fixation device (600) is traversing (C1) on the right sides of FIGS. 4a-4b. The C1 image corresponds to the coronal slice near the entrance to pedicle (902) as the transverse processes (903) extends laterally. The C2 image corresponds to the coronal slice of the pedicle (902) at its smallest circumference. A prior art pedicle screw (666) is traversing (C2) on the left sides of FIGS. 4a-4b. A threadless patient-specific fixation device (600) is traversing (C2) on the right sides of FIGS. 4a-4b. It is important to note that most pedicles (902) are oval or oblong and not round. Thus, the oval shape of patient-specific pedicle fixation devices (600) will have greater surface contact areas with subcortical bone inside the pedicle (902) than previous art pedicle screws (666).

FIG. 5 is an axial plane view of a target zone (40) of L5 vertebra (925). L5 pedicles (902) have larger diameters than the L3 pedicles. The medial-lateral insertion angles are also larger, averaging 45 degrees towards the midline. The current process' metric output (408) can make threadless patient-specific fixation device (600) with two enlargements or wings (637) in third region (636p) and surface treatments (632) in first, second and third regions (616, 626p, 636p). It is believed that surface treatments (632) facilitate bone ingrowth. Wings (637), rings or circumferential enlargements in the third region (636p) can limit the depth of insertion, optimize the alignment of the subcortical bone within pedicle (902) in second region (626p) of the patient-specific fixation device (600), increase the surface area for subcortical bone ingrowth from the transverse process (903) and lamina (905), increase the surface area for bone ingrowth of the inter-transverse process fusion, and provide a larger surface area to disperse loads transmitted from spinal levels adjacent to the patient-specific fixation device (600).

FIG. 6 is an axial plane view of first and second target zones (40) of L5 vertebra (925). A prior art threaded pedicle screw (666) traverses the target zone's (40) pedicle (902a). A threadless patient-specific pedicle fixation device (600) traverses the target zone's (40) pedicle (902b). In addition to wings (637), metric (408) of the process (123) for making a patient-specific spinal fixation device (600) manufactured a bend in third region (636p). As shown, first region (616) and second region (626p) are centered about shared midline (M-M) while midline (M1-M1) of third region (636p) and fourth region (646) includes an offset angle of about 30 degrees relative to shared midline (M-M) of first region (616) and second region (626p). This medial-lateral angulation adjustment can reduce the dissection area required for implantation and the risk for a post-operative infection. This personalized angulation adjustment can also simplify connection with other spinal devices.

Figure 7:
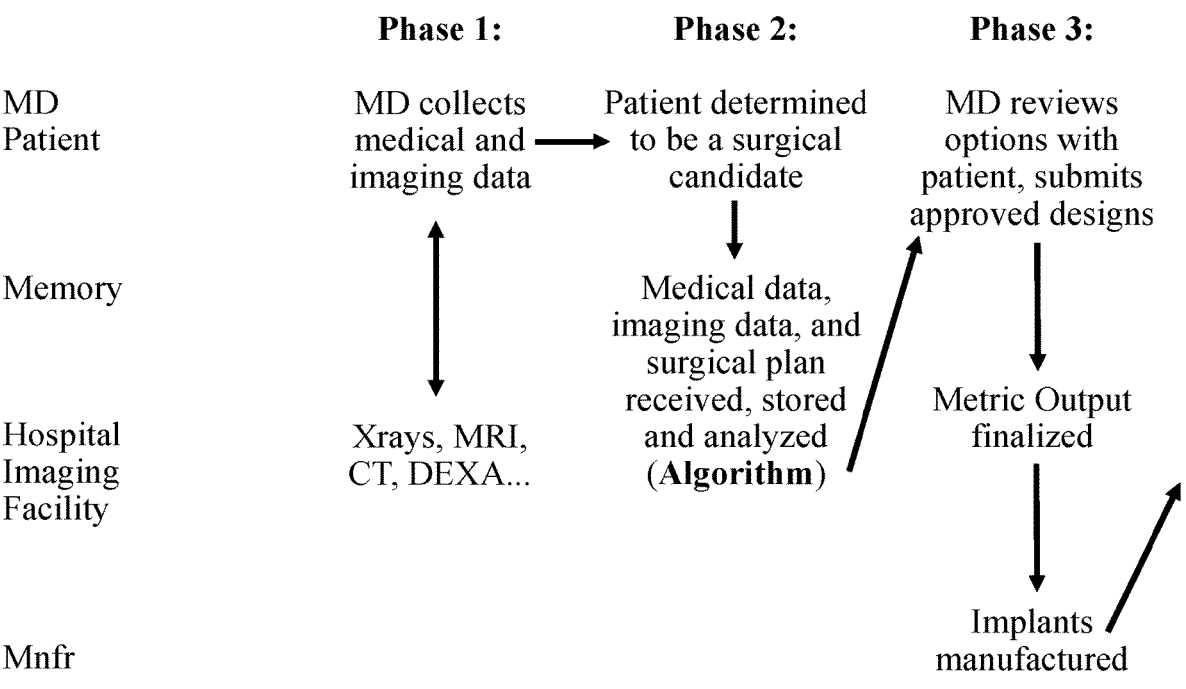
FIG. 7 is an illustrative flow chart for the process (123) of making a patient-specific implant (600).

FIG. 7 is an illustrative flow chart for the process (123) of making a patient-specific implant (600) during the pre-operative period.

Figure 8:
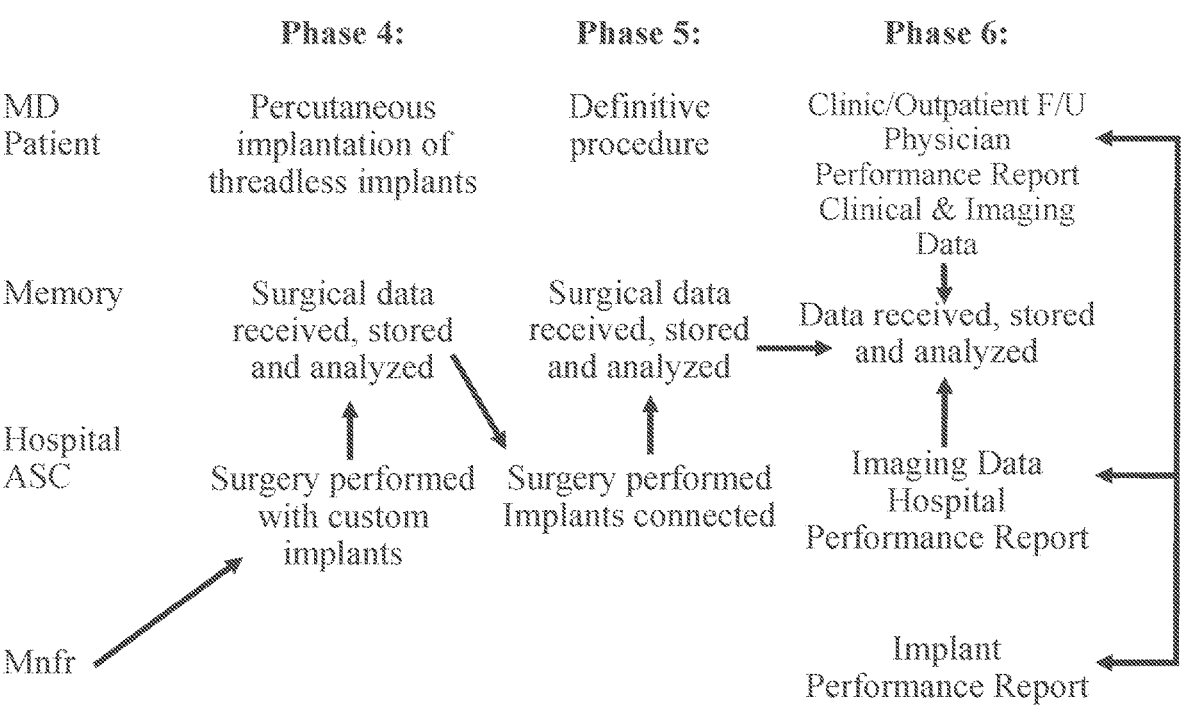
FIG. 8 is an illustrative flow chart for implantation and clinical evaluations of the patient-specific implant (600).
Figure 9:
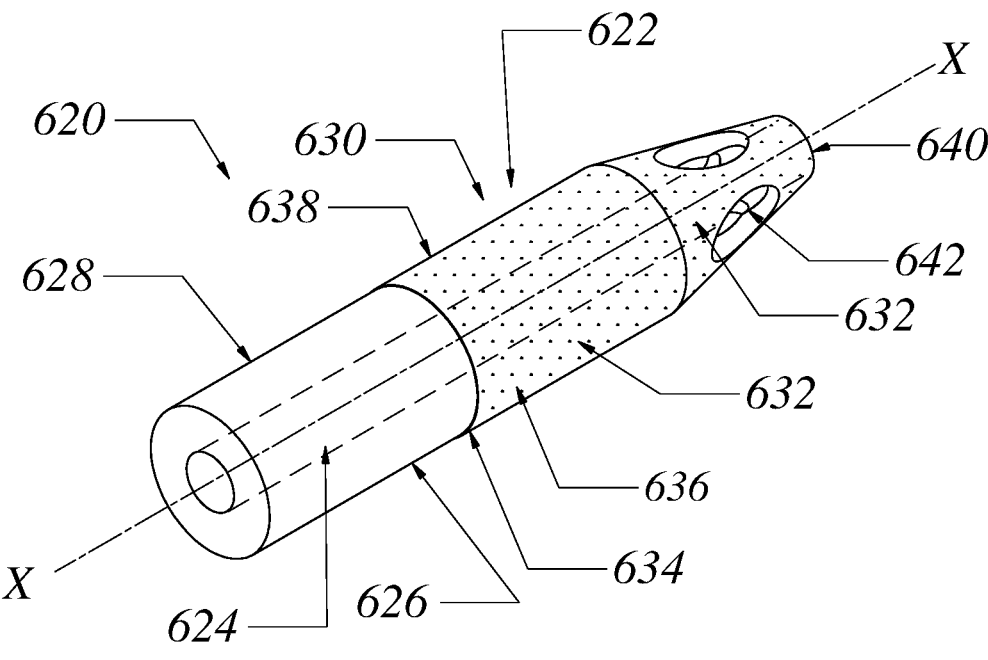
FIG. 9 illustrates a type of patient specific implant (600) that can be manufactured by the current process (123).
Figure 10:
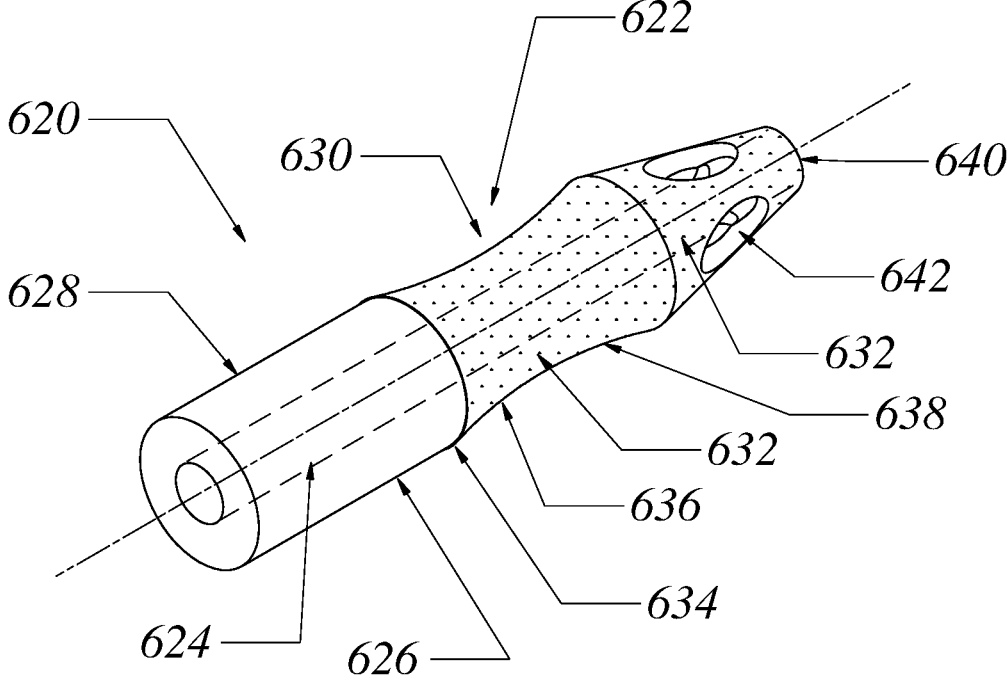
FIG. 10 illustrates a type of patient specific implant (600) that can be manufactured by the current process (123).
Figure 9A:
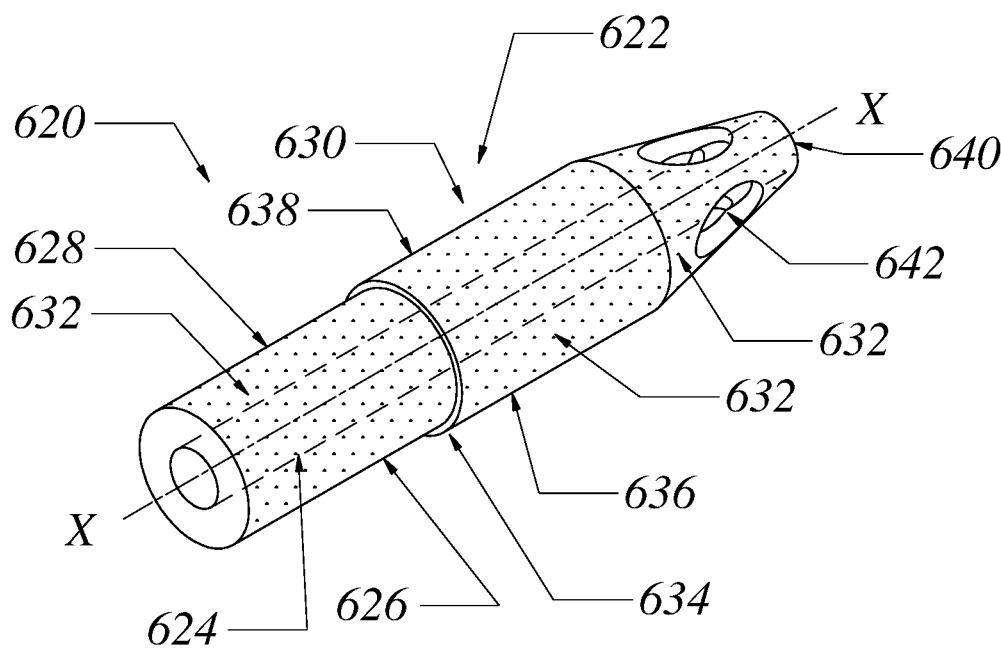
FIG. 9a illustrates a type of patient specific implant (600) that can be manufactured by the current process (123).
Figure 10A:
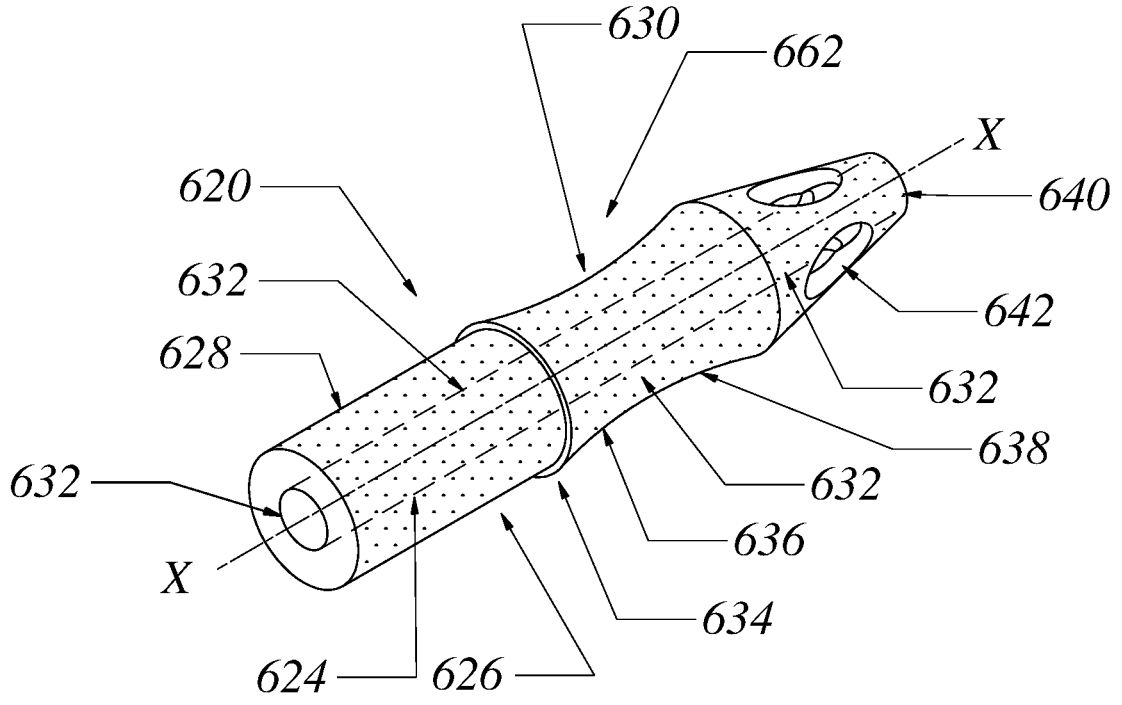
FIG. 10a illustrates a type of patient specific implant (600) that can be manufactured by the current process (123).
Figure 11:
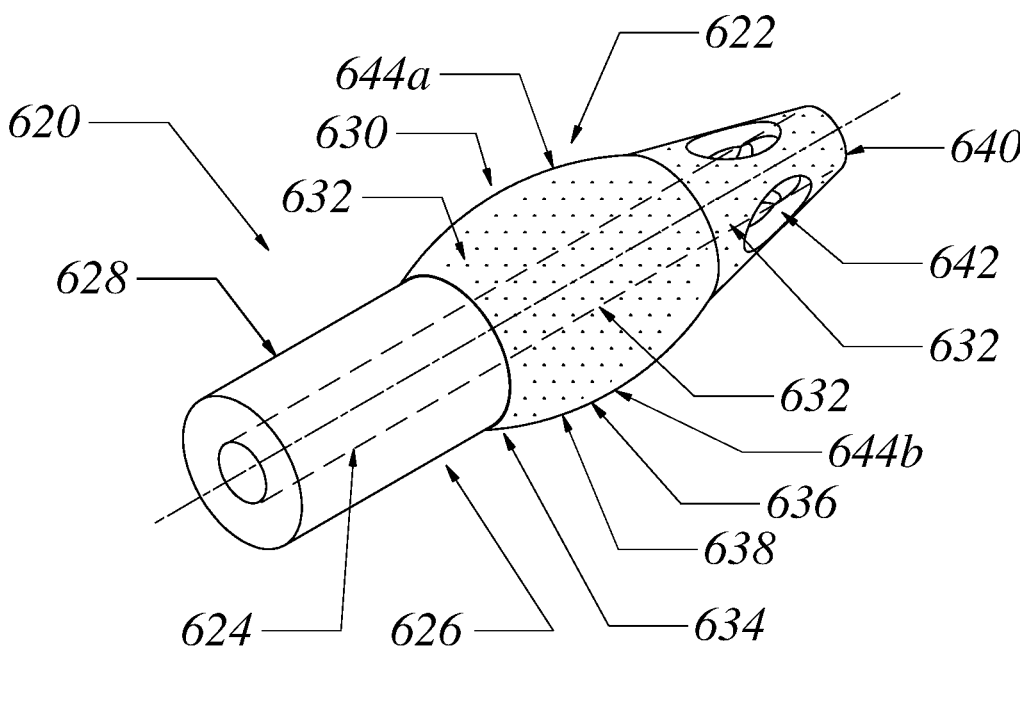
FIG. 11 illustrates a type of patient specific implant (600) that can be manufactured by the current process (123).
Figure 12:
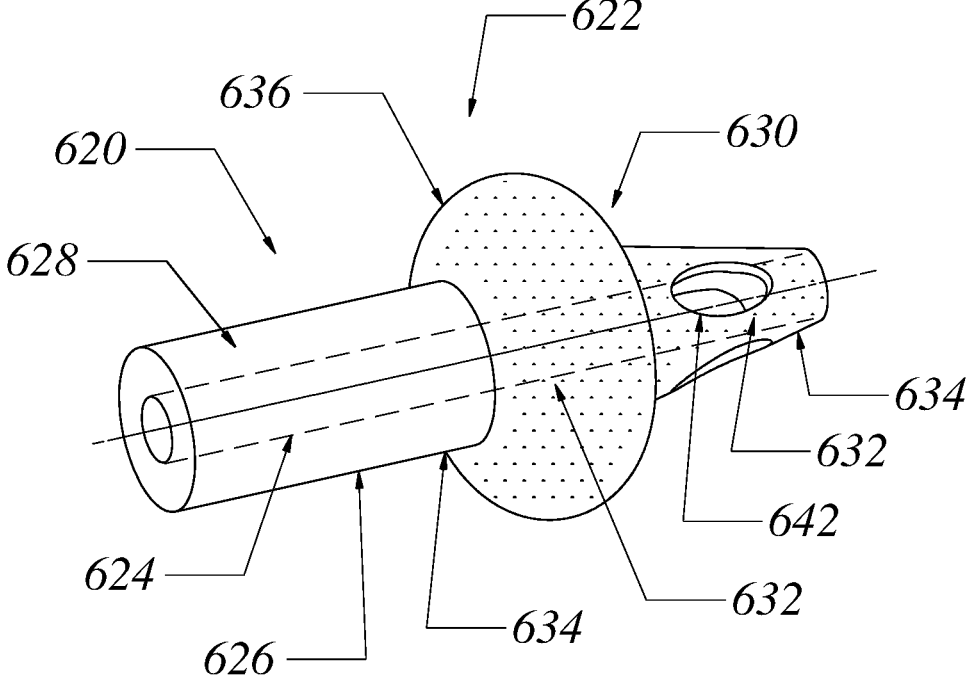
FIG. 12 illustrates a type of patient specific implant (600) that can be manufactured by the current process (123).
Figure 11A:
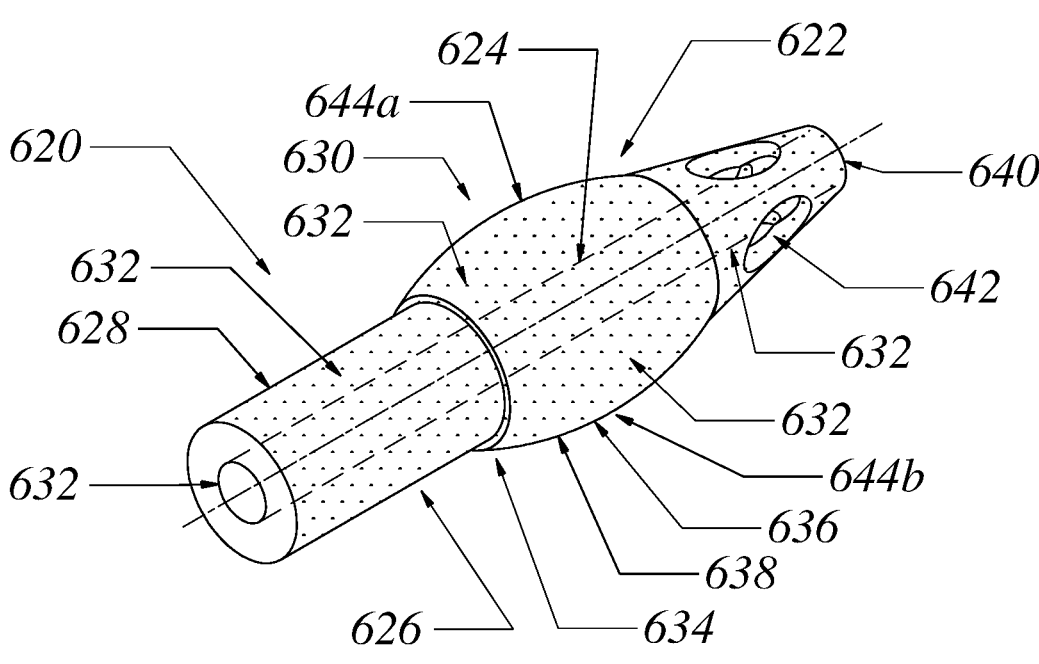
FIG. 11a illustrates a type of patient specific implant (600) that can be manufactured by the current process (123).
Figure 12A:
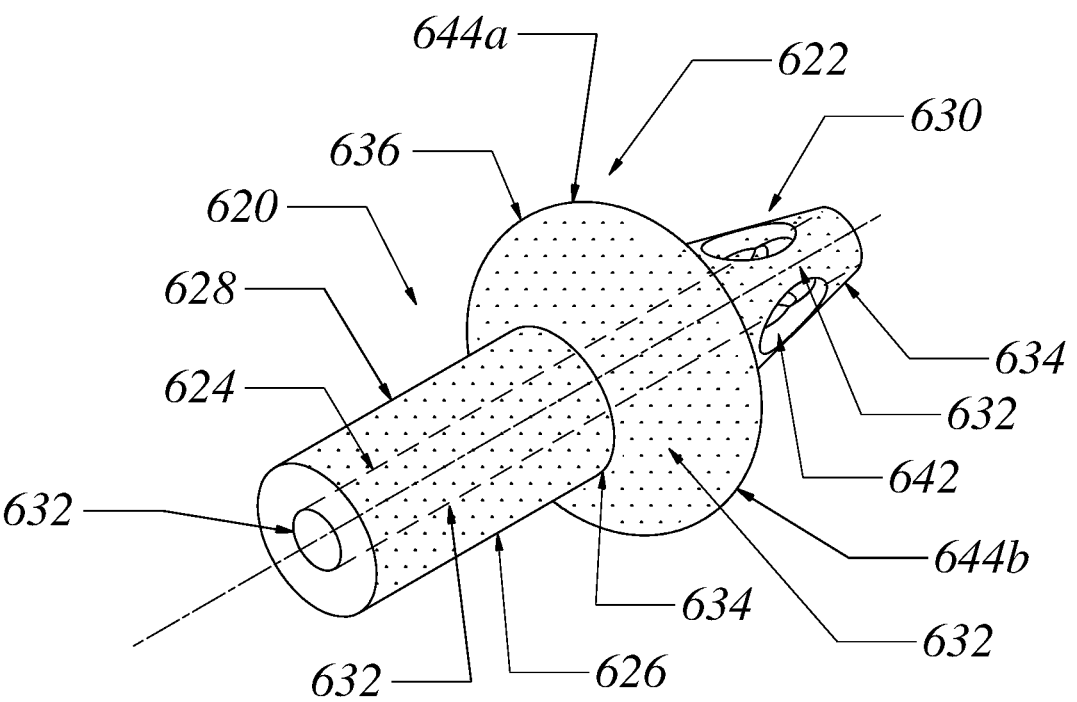
FIG. 12a illustrates a type of patient specific implant (600) that can be manufactured by the current process (123).
Figure 13:
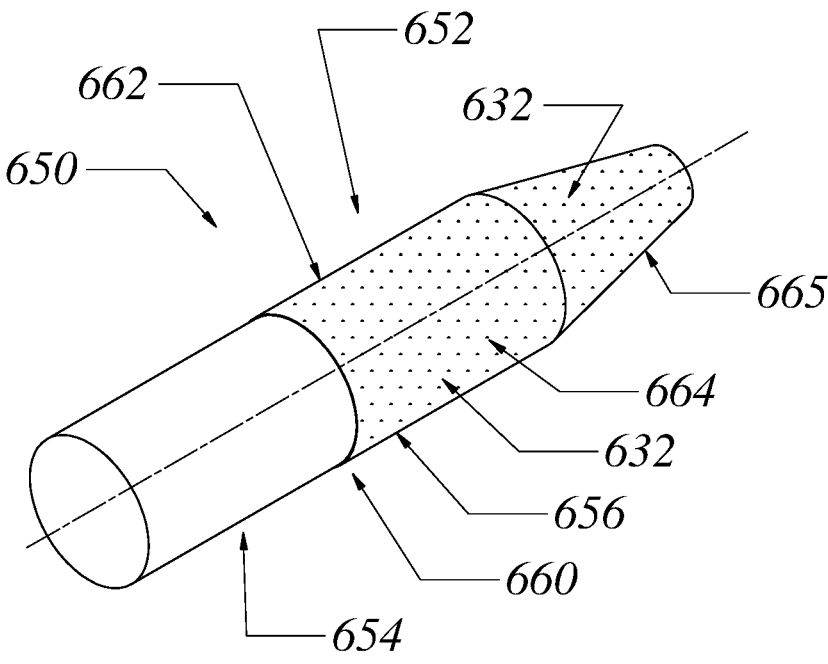
FIG. 13 illustrates a type of patient specific implant (600) that can be manufactured by the current process (123).

FIG. 8 is an illustrative flow chart for the implantation and clinical evaluations of the patient-specific implant (600).

Select Preferred Embodiments of Patient-Specific Implants that can be Manufactured by the Current Process (123)

Within the scope of the current process (123), it has advantageously been discovered that the series 600 (620, 650, 690) patient-specific implants (600) can have lengths from about 20 to about 75 millimeters; polyaxial heads (100) can have lengths of from about 10 millimeters to about 25 millimeters. However, other patient-specific implants within the scope of the current process (123) can have different measurements.

Preferred embodiments of process (123) can utilize additive techniques, such as 3D printing, to build the device out of microscopic metal particles. Implants can be built particle by particle over the height, length and width of the patient-specific implant. Particles can be fused together to maximize density and create smooth (external) surfaces exposed to a surgical environment. It is believed that densely fused particles improve a 3D printed implant's biomechanical strength. Densely fused particles can also provide the 3D printed implant a smooth surface over which connectors and other devices can be attached. In contrast, particles fused together in clumps can create a rough or a porous texture. Rough or porous surfaces may sacrifice implant strength for the facilitation of bone ingrowth. In select preferred embodiments, rough surfaces can be included with a conduit of the current implant. Bone ingrowth into the patient-specific implant can increase the implant's biomechanical strength and allow living bone or other tissues to grow into available spaces.

Preferred embodiments of process (123) can utilize subtractive manufacturing methods that start with a solid block of metal or other composition acceptable in the art that is larger in height, length and width than the patient-specific implant. Subtractive manufacturing removes portions of the block to create the preselected dimensions of the implant. Abrasive particles, lasers and/or chemical treatments can be used to roughen the surface of the implant. During subtractive manufacturing of the implant, its total size decreases with each intervention.

By way of illustration, patient-specific implants can be created by the combination of subtractive and additive manufacturing techniques where an additive rough surface is added to the implant initially created by subtractive manufacturing. For example, press-fit total hip and press-fit total knee implants can be manufactured with the combination of subtractive and additive manufacturing techniques.

It is believed that rough surfaces can assist with long term fixation of the patient-specific implants by allowing more bone ingrowth onto and/or into the implant. Within the scope of the current process (123), either additive or subtractive means or a combination thereof can create the rough surfaces for any exposed surface of the patient-specific implants. For the purposes of this Application, "rough surfaces" are defined as, "biocompatible surfaces created by additive and/or subtractive means on any surface of the patient-specific implant that can facilitate ingrowth or interdigitation of the host tissues with the implant."

Returning to the series 600 implants; FIGS. 9-27j illustrate types of patent specific implants (620, 650, 690) that can be manufactured by process (123).

In a preferred embodiment, patient-specific implant (620) is provided with cannula (622). Cannula (622) includes conduit (624) adapted to carry one or more biocompatible substances. Conduit (624) traverses an entire length of a longitudinal axis of cannula (622).

Barrier (626) surrounds conduit (624). Barrier (626) can be provided with a first cylindrical section (628) with layers of rough surfaces (632) and a second section (630), adjacent to the first cylindrical section (628), with more layers of rough surfaces (632) than the first cylindrical section (628). First cylindrical section (628) includes a first diameter (634) merged with the second section (630). Second section (630) includes first segment (636) proximate the first cylindrical section (628). A portion of a cross-sectional diameter (638) of the first segment (636) is less than, equal to or greater than the first diameter (634). Second segment (640) is merged and connected with the first segment (636). Second segment (640) is interrupted by one or more openings (642) allowing interactions between conduit (624) and a surgically created environment proximate patient-specific implant (620).

Among other things, rough surfaces (632) can include micropores, metal, abrasive particles, dense particles or clumps of particles.

When for the surgically created cavity dictates, first segment (636) is cylindrical and second segment (640) is conical.

When the surgically created cavity dictates, first segment (636) is biconvex and the second segment (640) is conical. First segment (636) can be provided with a greater length than curved lengths of each opposed convex sides (644a, 644b). First segment (636) can also be ovoid.

When the surgically created cavity dictates, first segment (636) is biconcave and second segment (640) is conical.

Figure 19:
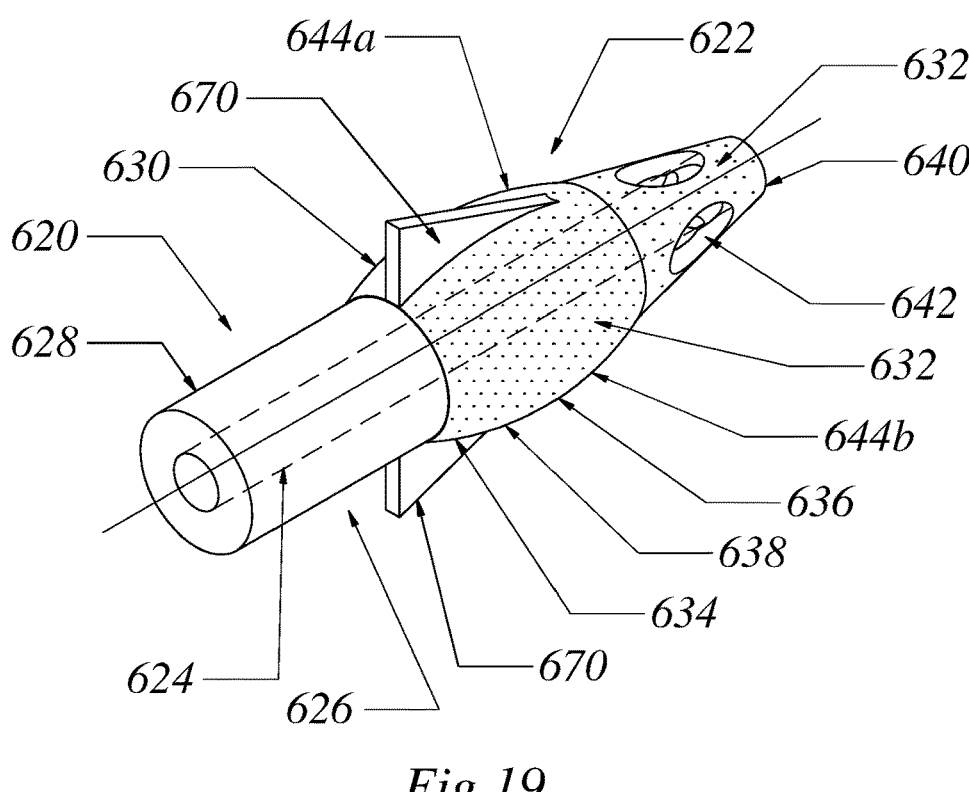
FIG. 19 illustrates a type of patient specific implant (600) that can be manufactured by the current process (123).
Figure 20:
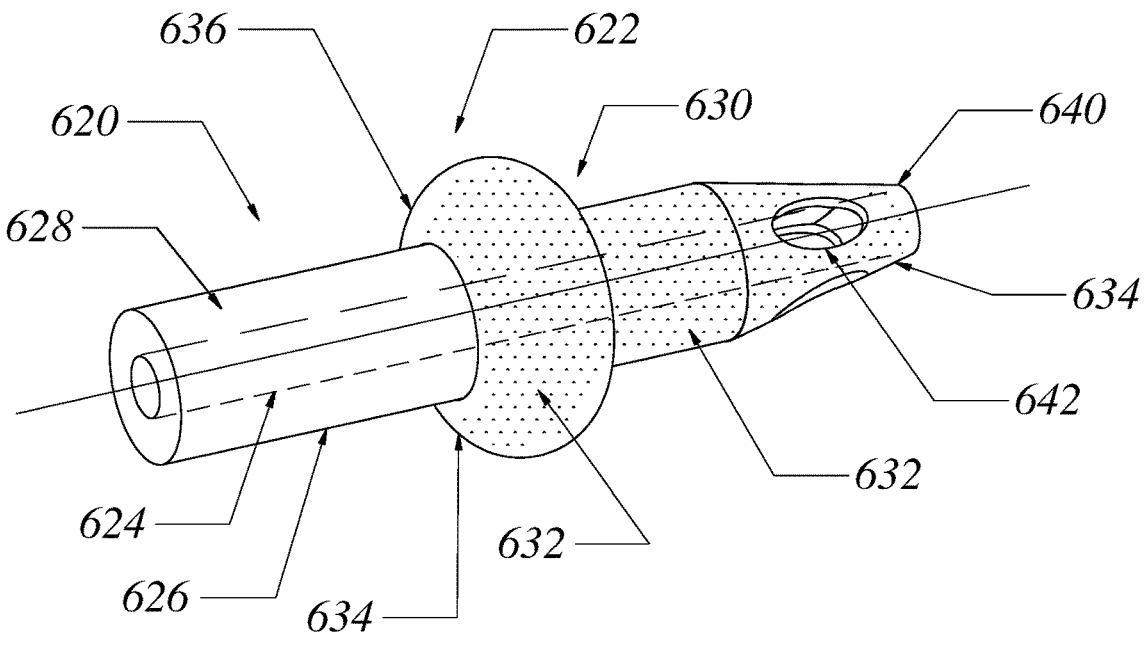
FIG. 20 illustrates a type of patient specific implant (600) that can be manufactured by the current process (123).
Figure 21:
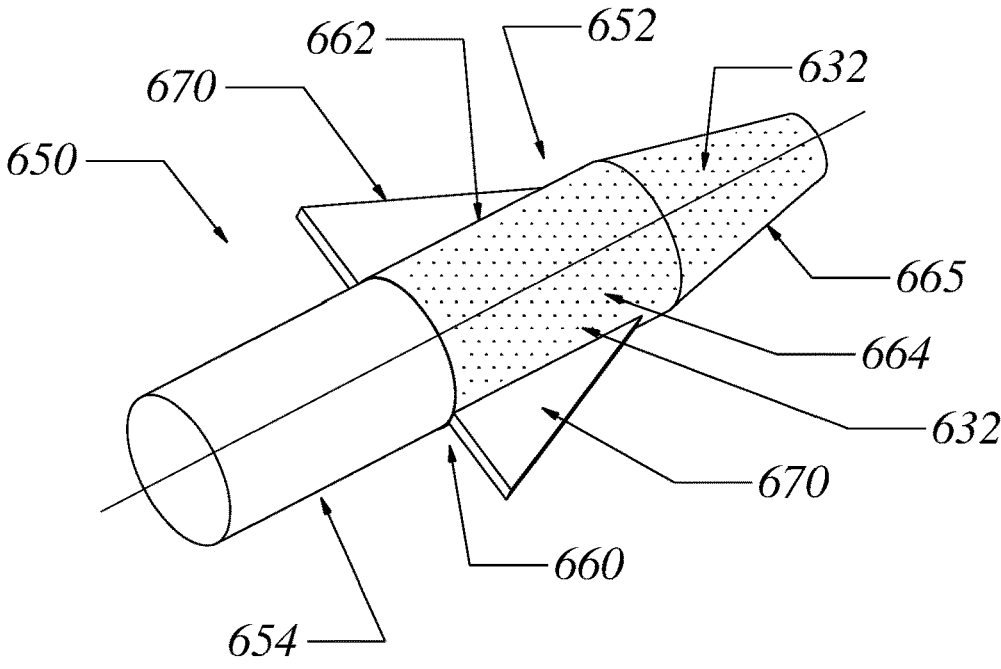
FIG. 21 illustrates a type of patient specific implant (600) that can be manufactured by the current process (123).
Figure 22:
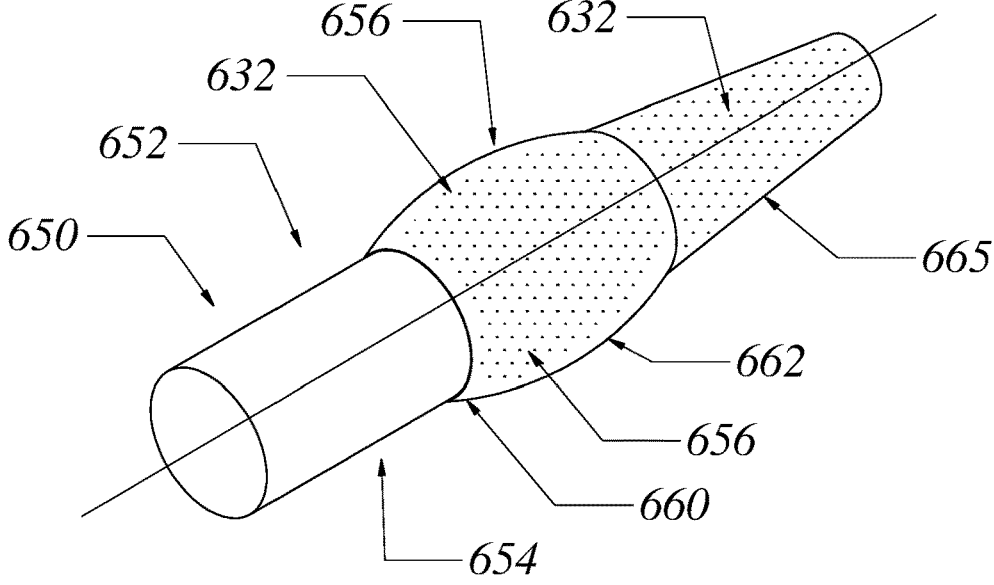
FIG. 22 illustrates a type of patient specific implant (600) that can be manufactured by the current process (123).
Figure 23:
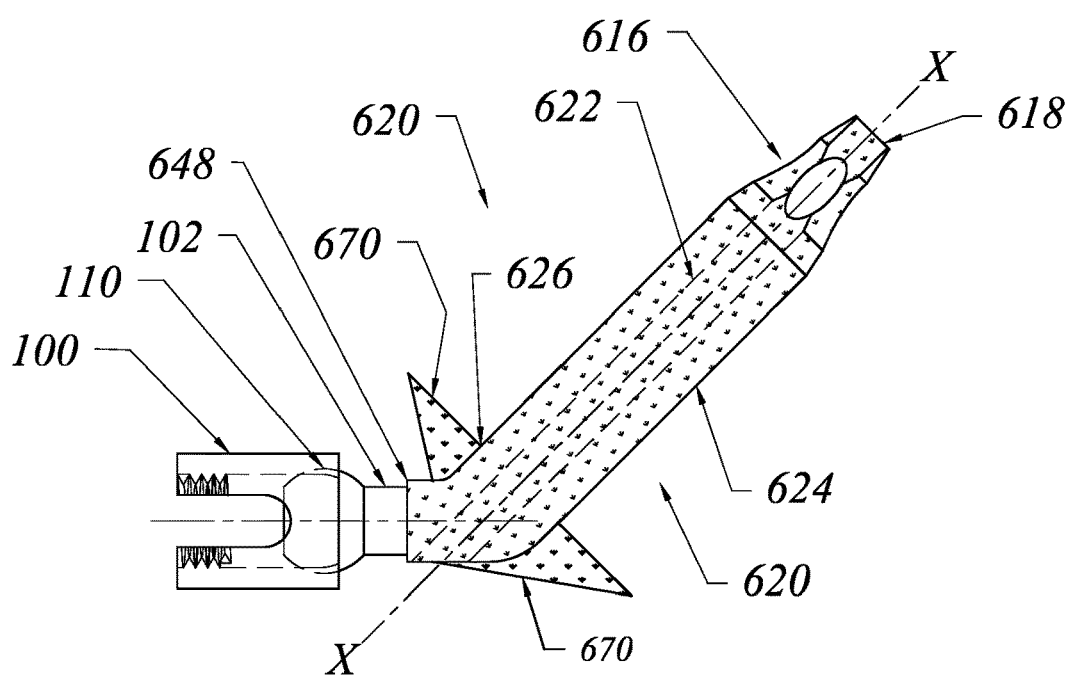
FIG. 23 illustrates a type of patient specific implant (600) that can be manufactured by the current process (123).

As shown in FIG. 19, when the surgically created cavity dictates, patient-specific implant (620) can be provided with wings or bulges (670).

Figure 17:
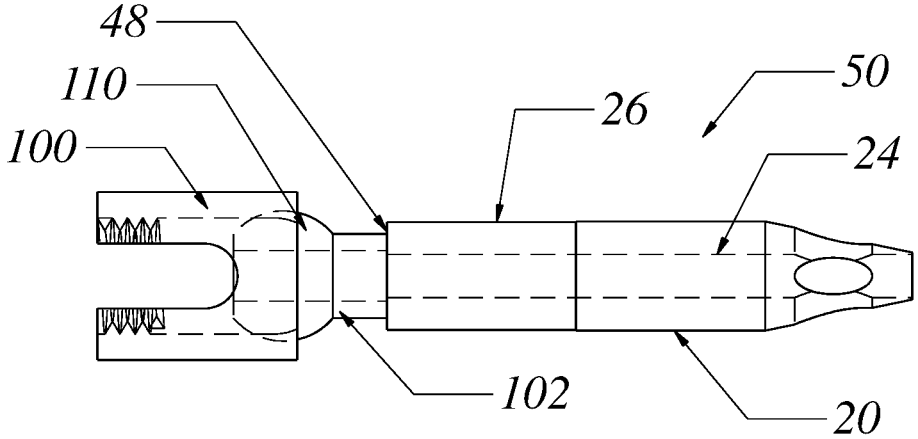
FIG. 17 illustrates a type of patient specific implant (600) that can be manufactured by the current process (123).
Figure 18:
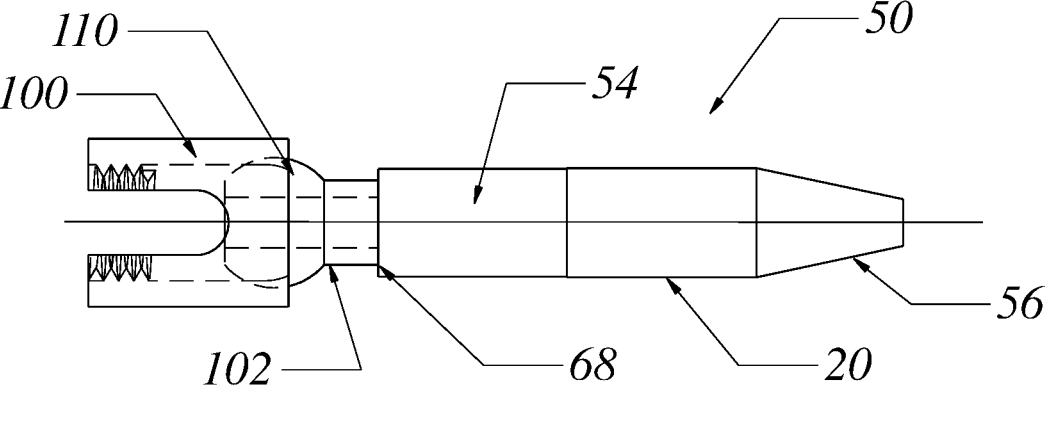
FIG. 18 illustrates a type of patient specific implant (600) that can be manufactured by the current process (123).
Figure 24:
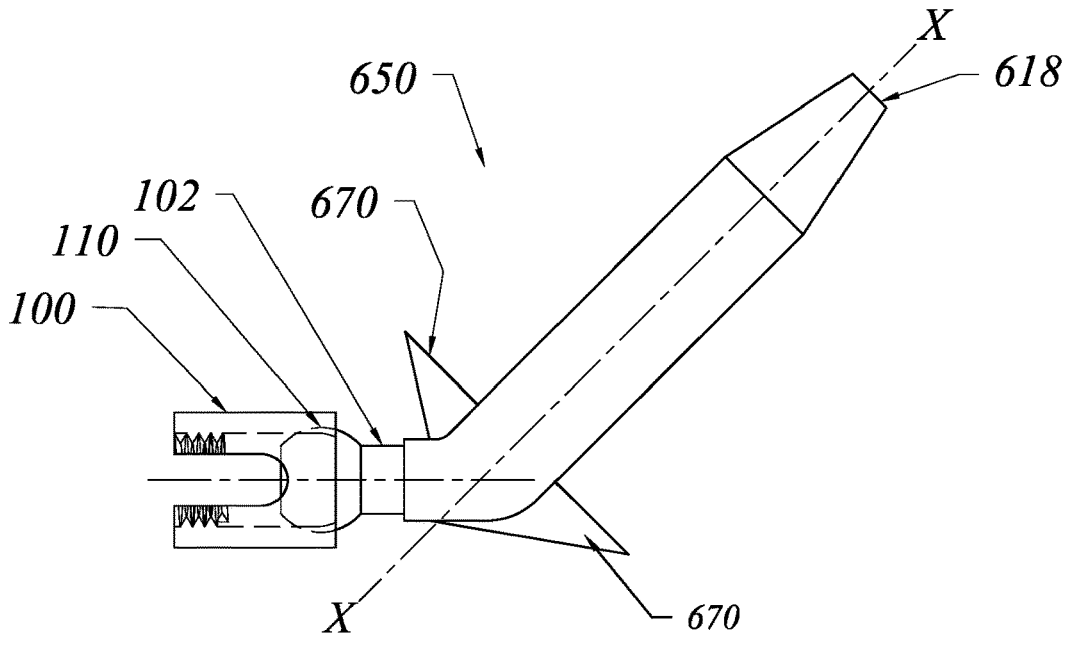
FIG. 24 illustrates a type of patient specific implant (600) that can be manufactured by the current process (123).

Select preferred embodiments of patient-specific implant (620) shown in FIG. 17 can be provided with polyaxial head (100) connected to spheroid connector (102) that is attached to first side (648) of barrier (626) opposite the second segment (640). As shown, conduit (624) reciprocates with channel (104) of spheroid connector (102). Polyaxial head (100) includes receptacle (110) that snap fits/locks over spheroid connector (102). As shown in FIG. 24, spheroid connector (102) can be offset of up to about 45 degrees from the longitudinal axis (X-X) of patient-specific implant (620).

FIGS. 13-16a are lateral perspectives of patient-specific implant (650).

In a preferred embodiment, patient-specific implant (650) has a longitudinal axis extending through the solid patient-specific implant (650). Solid patient-specific implant (650) can be provided with an uninterrupted exterior (652), first cylindrical section (654) with rough surfaces (658) and second section (656), adjacent to first cylindrical section (654), with more rough surfaces (658) than the first cylindrical section (654). First cylindrical section (654) includes a first diameter (660) merged with the second section (656).

Second section (656) is provided with first segment (662) proximate first cylindrical section (654). A portion of cross-sectional diameter (664) of first segment (662) is less than, equal to or greater than first diameter (660). Second segment (665) is merged and connected with first segment (662).

Among other things, rough surfaces (632) can include micropores, metal, abrasive particles, dense particles or clumps of particles.

When the surgically created cavity dictates, first segment (662) is cylindrical and second segment (665) is conical.

When the surgically created cavity dictates, first segment (662) is biconvex and second segment (665) is conical. First segment (662) can be provided with a greater length than curved lengths of each opposed convex side (672a, 672b). First segment (662) can also be ovoid.

When the surgically created cavity dictates, first segment (662) is biconcave or concave.

As shown in FIG. 24, when the surgically created cavity dictates, patient-specific implant (650) can be provided with wings or bulges (670).

Figure 14:
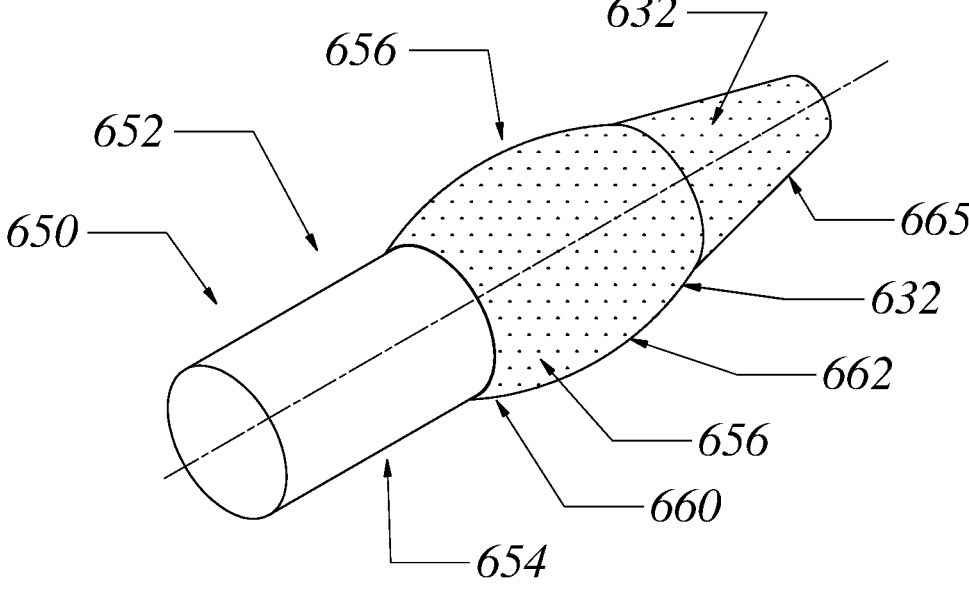
FIG. 14 illustrates a type of patient specific implant (600) that can be manufactured by the current process (123).
Figure 13A:
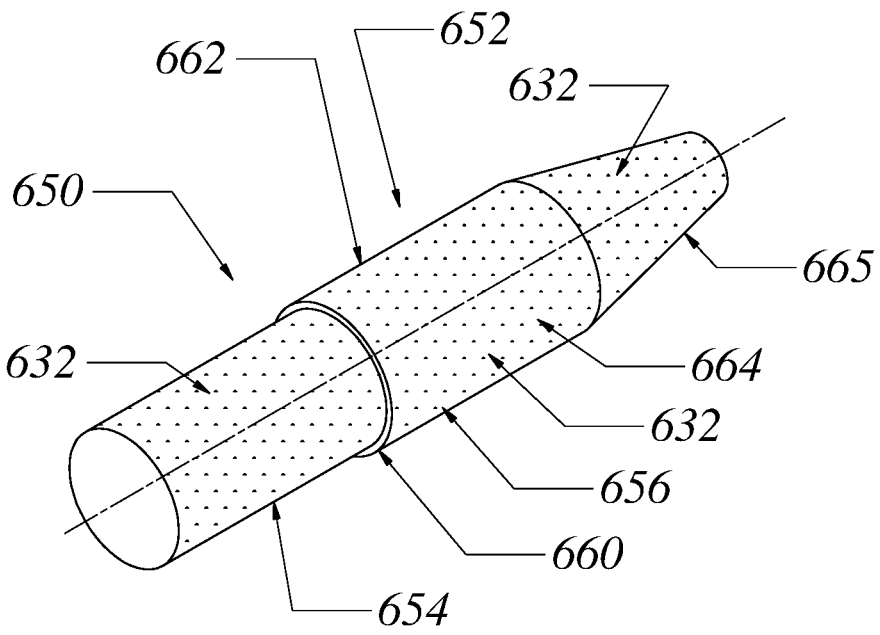
FIG. 13a illustrates a type of patient specific implant (600) that can be manufactured by the current process (123).
Figure 14A:
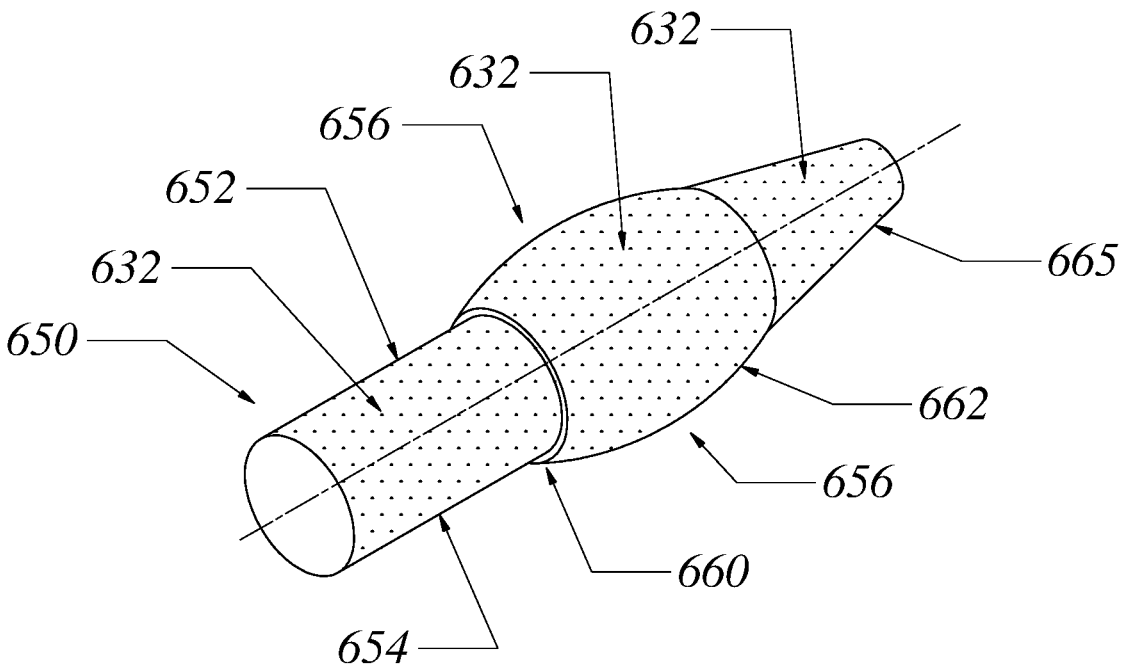
FIG. 14a illustrates a type of patient specific implant (600) that can be manufactured by the current process (123).
Figure 15:
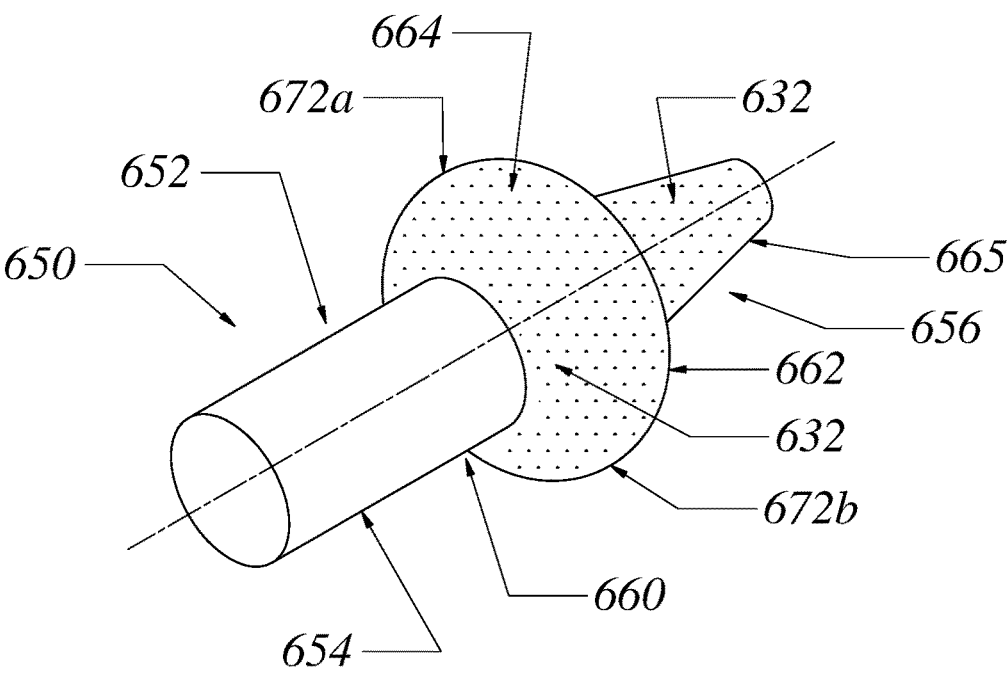
FIG. 15 illustrates a type of patient specific implant (600) that can be manufactured by the current process (123).
Figure 16:
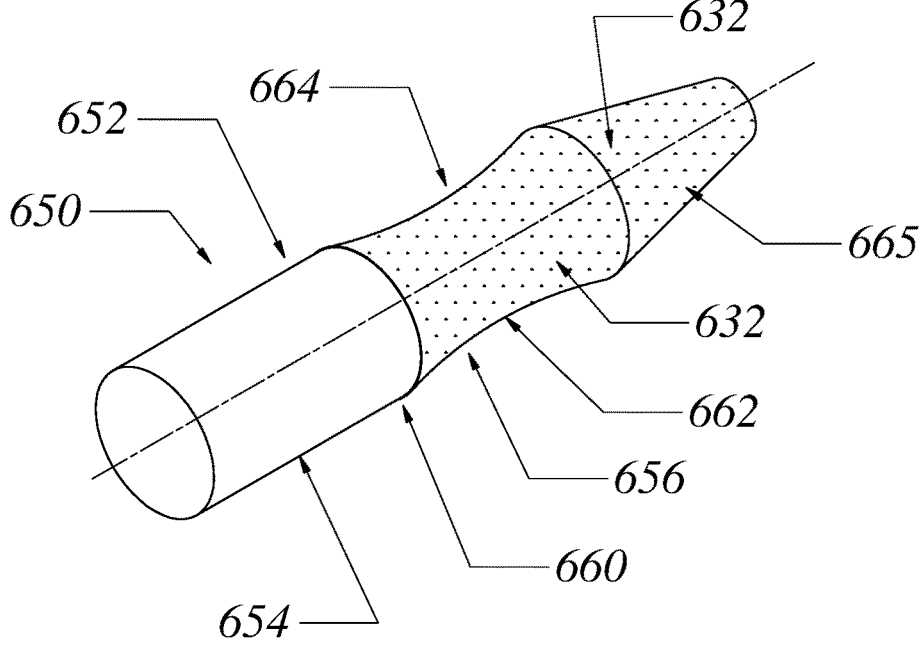
FIG. 16 illustrates a type of patient specific implant (600) that can be manufactured by the current process (123).
Figure 15A:
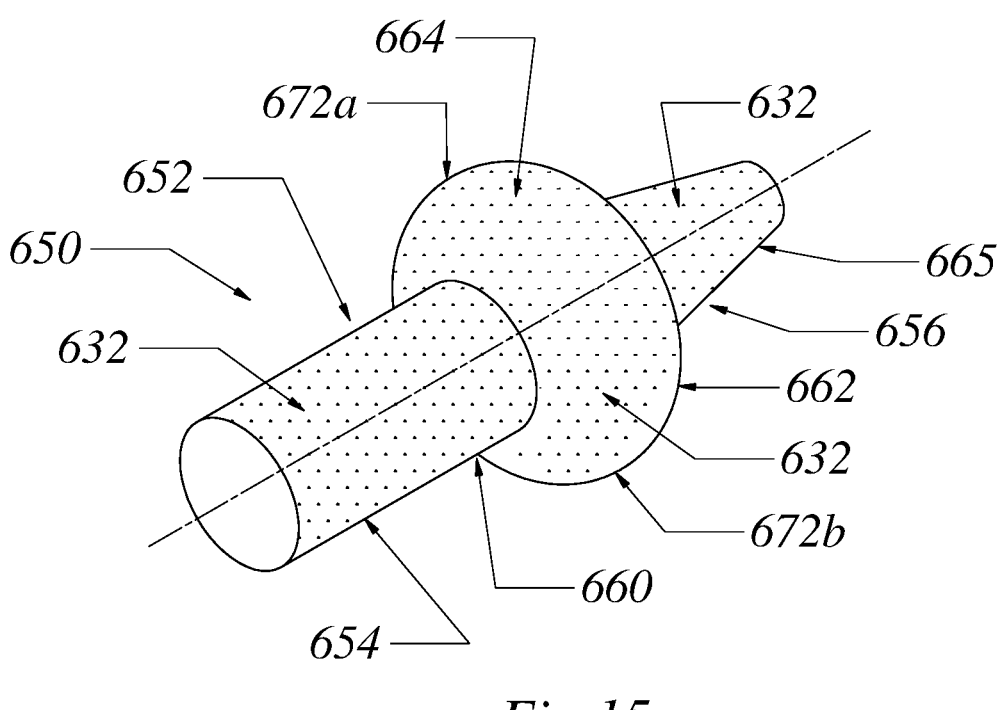
FIG. 15a illustrates a type of patient specific implant (600) that can be manufactured by the current process (123).
Figure 16A:
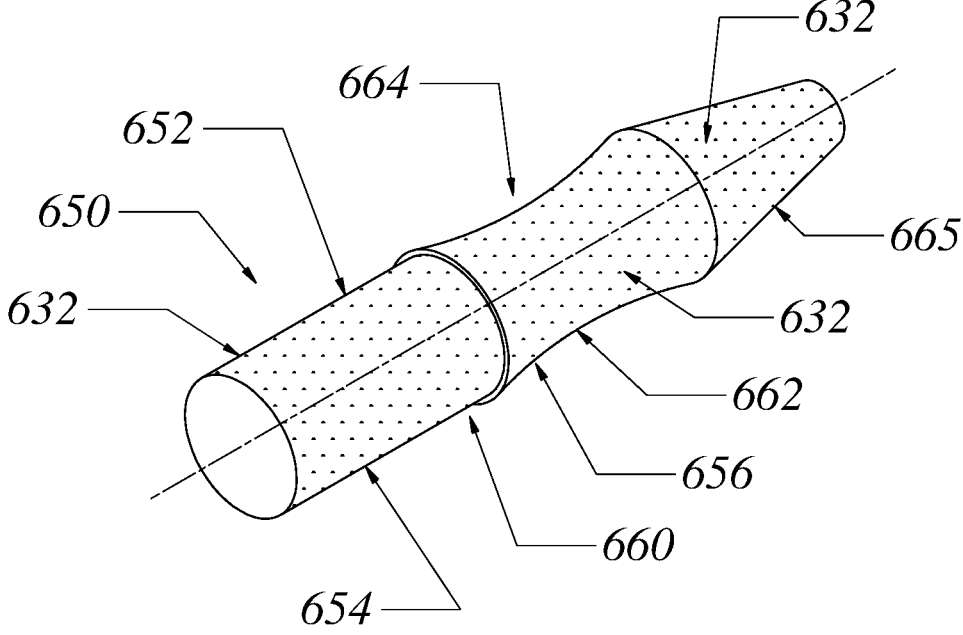
FIG. 16a illustrates a type of patient specific implant (600) that can be manufactured by the current process (123).

Select preferred embodiments of patient-specific implant (650) shown in FIG. 14 can be provided with polyaxial head (100) connected to spheroid connector (102) that is attached to first cylindrical section (654). Polyaxial head (100) includes receptacle (110) that snap fits/locks over spheroid connector (102). As shown in FIG. 24, spheroid connector (102) can be offset of up to about 45 degrees from the longitudinal axis (X-X) of patient-specific implant (650).

Figure 25:
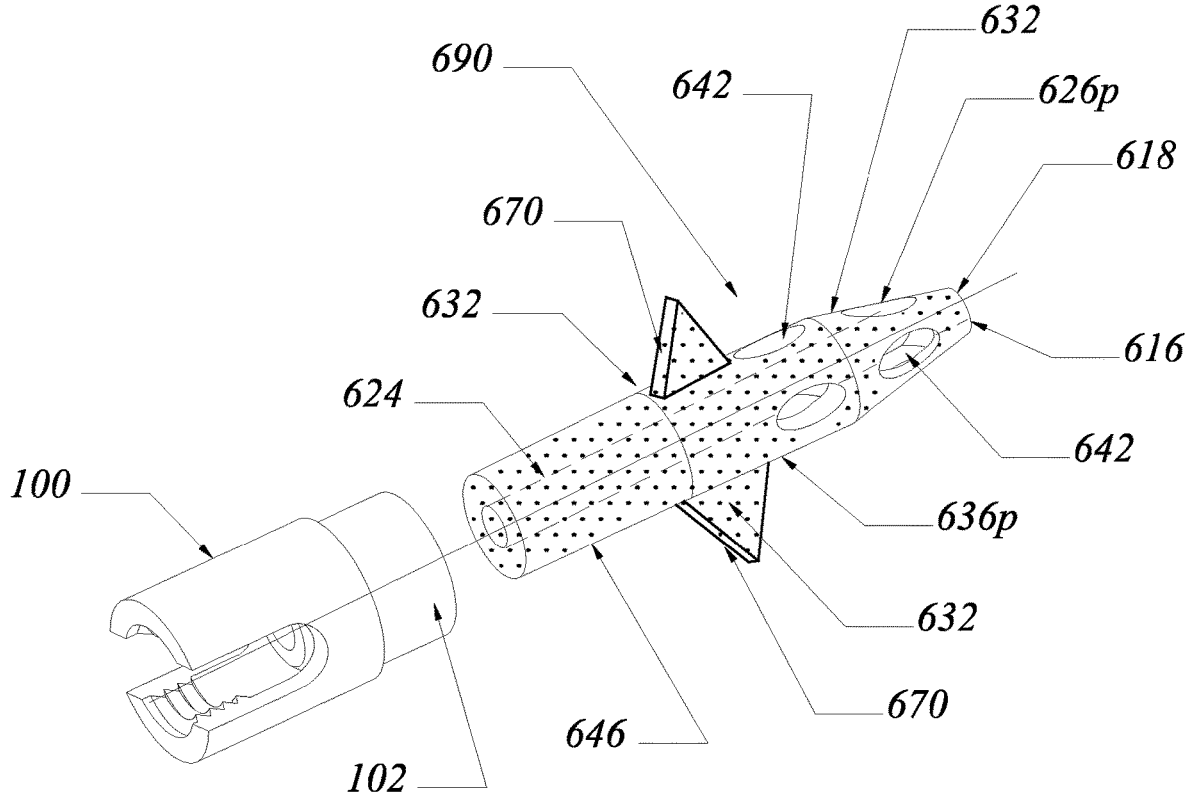
FIG. 25 illustrates a type of patient specific implant (600) that can be manufactured by the current process (123).
Figure 26D:
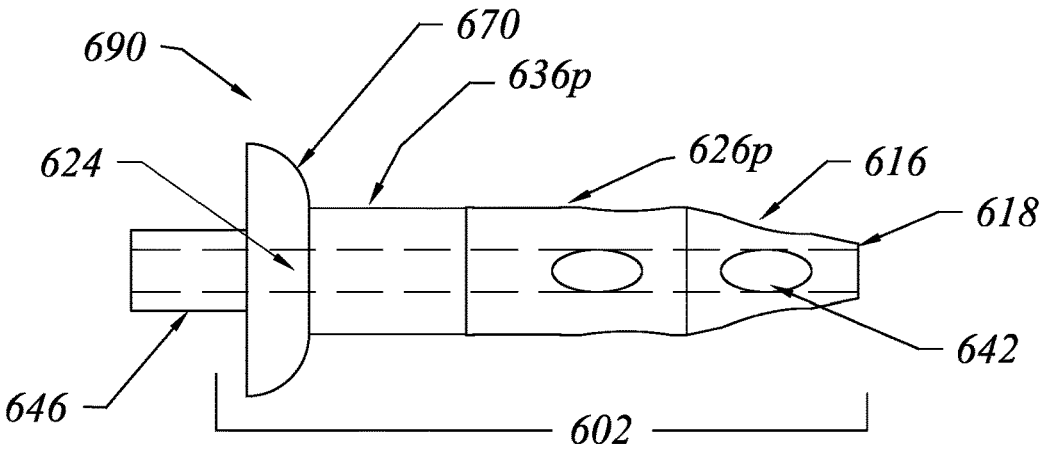
Figure 26E:
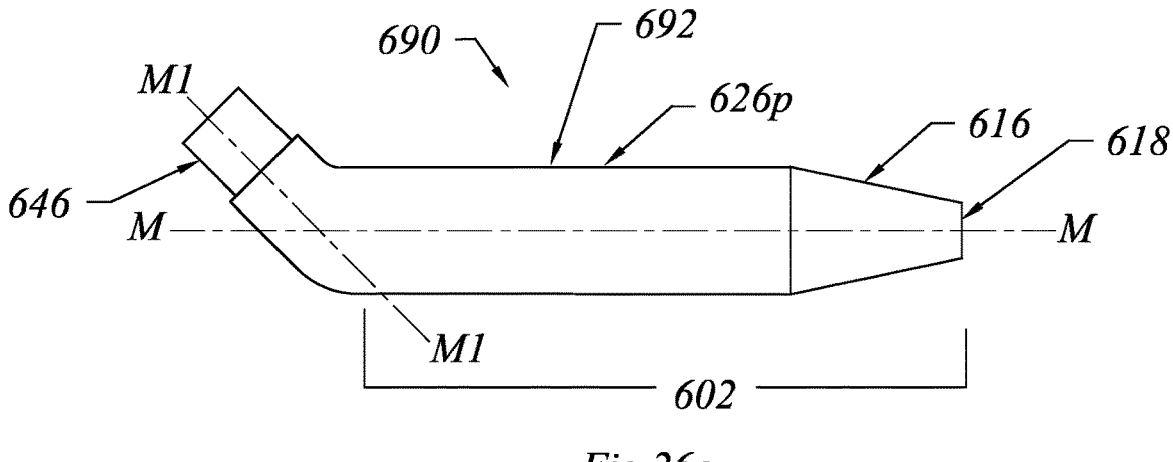
Figure 26F:
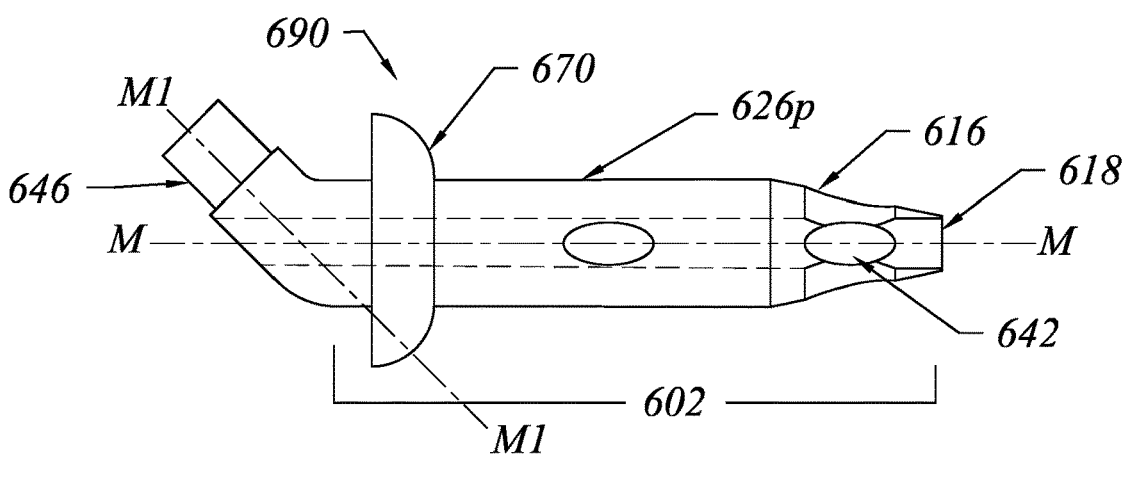
Figure 27D:
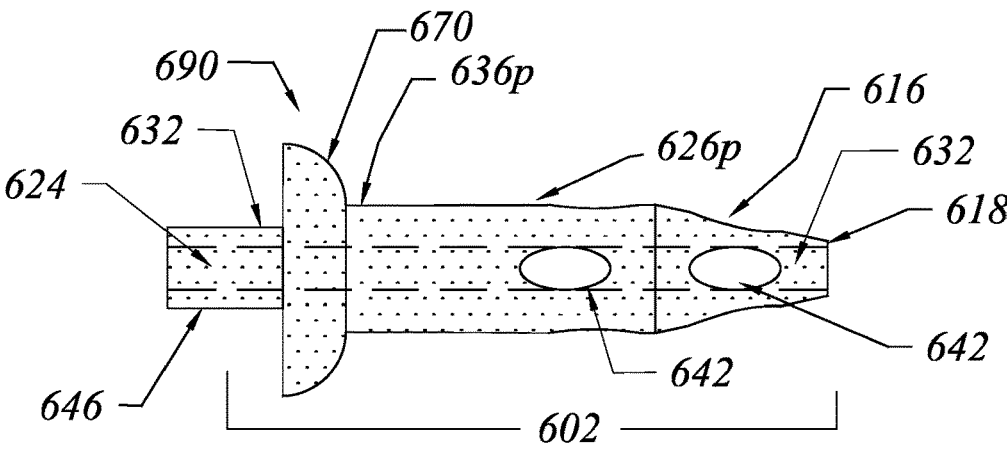
Figure 27E:
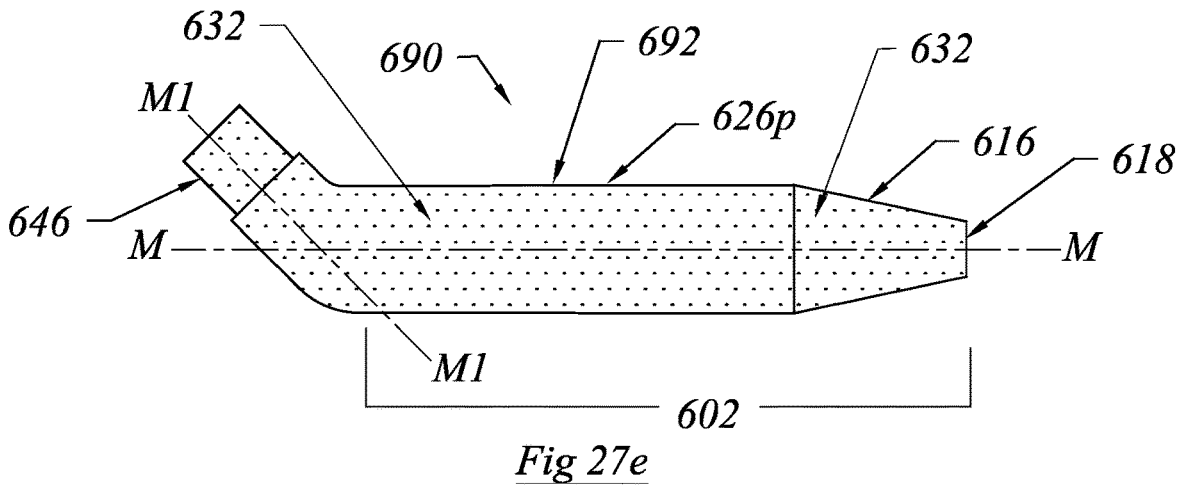
Figure 27F:
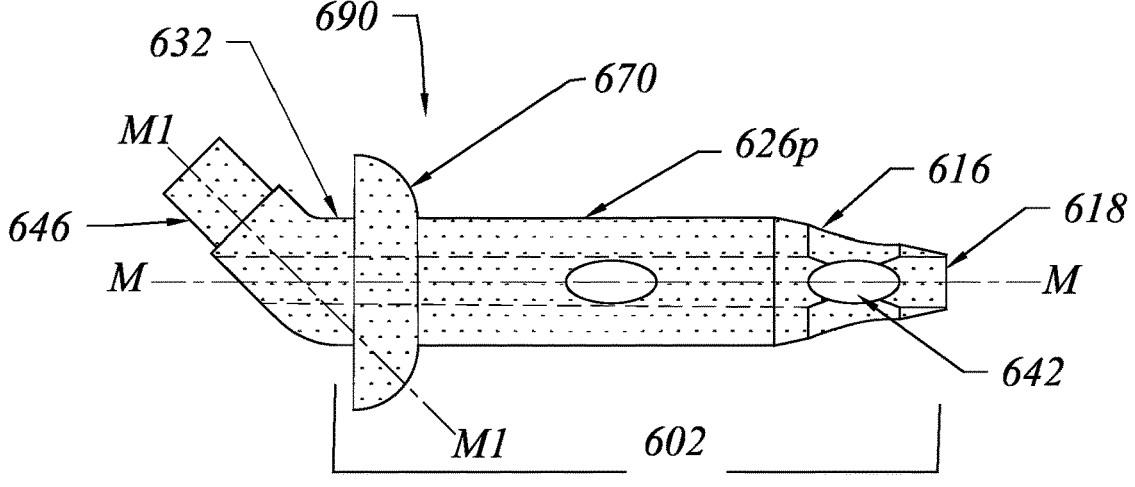
Figure 27G:
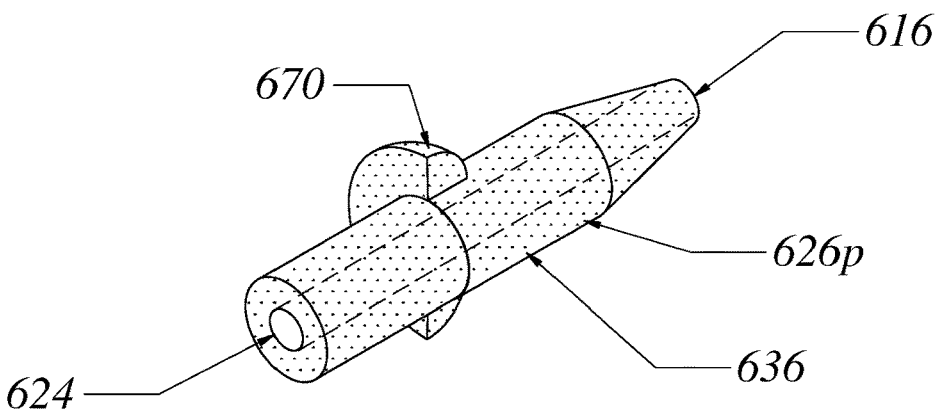
Figure 27H:
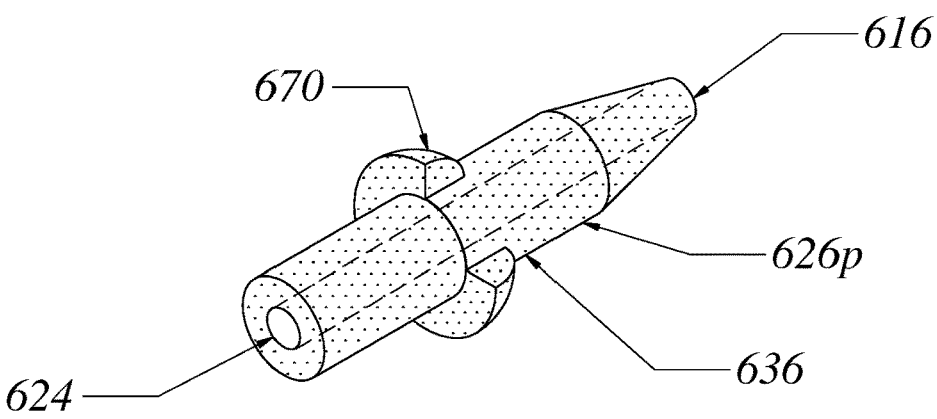
Figure 27I:
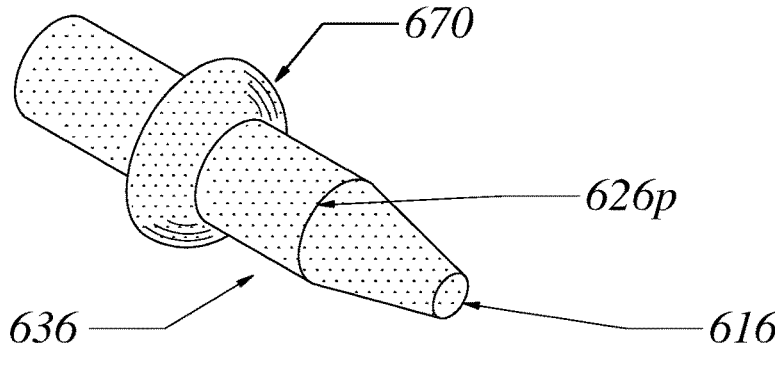
Figure 27J:
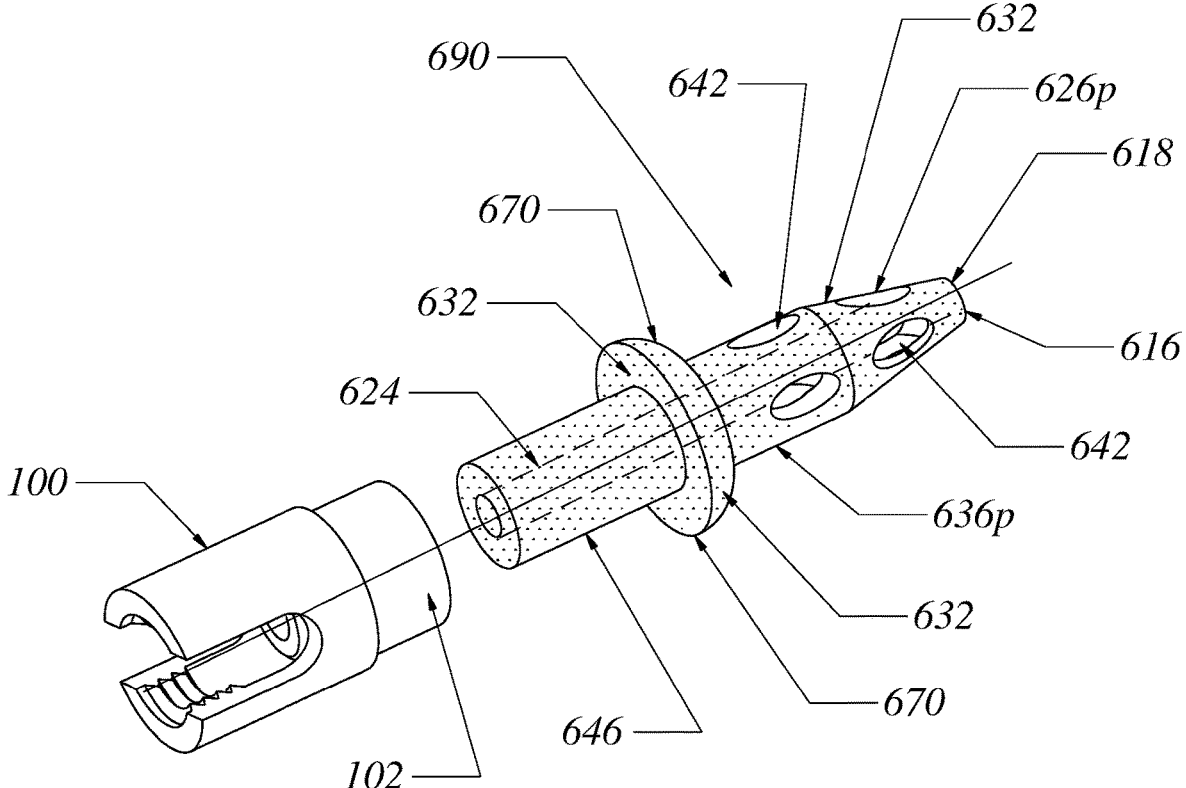

FIG. 25 is a lateral perspective of patient-specific implant (690) including an exploded view of polyaxial head (100) and spheroid connector (102). Patient-specific implant (690) is provided with first region (616), second region (626p), third region (636p) and fourth region (646). Conduit (624) traverses first region (616), second region (626p) and third region (636p), and, in select preferred embodiments, can also traverse fourth region (646). First Region (616) can have a blunt tip (618) leading edge in front and connects posteriorly to second region (626p). The threadless friction fit surgical implant (690) in second region (626p) can have dimensions that maximize surface contact area with the geometric dimensions of the target zone. Second region (626p) is connected to first region (616) and third region (636p). Wings or bulges (670) can be incorporated into third region (636*p*). When medical parameters require, bends or curves can be incorporated into fourth region (646). Threadless friction fit surgical implant (690) can be provided with one or more openings (642) allowing interactions between conduit (624) and the target zone or surgically created environment proximate threadless friction fit surgical implant (690). Depending on medical parameters, any combination of first region (616), second region (626*p*), third region (636*p*), fourth region (646) and conduit (624) can be provided with rough surfaces (632). Rough surfaces (632) can include micropores, metal, abrasive particles, dense particles or clumps of particles.

FIGS. 26*a*-26*f* show lateral perspectives of preferred embodiments of threadless friction fit surgical implant (690) for implantation into a patient. These preferred embodiments of threadless friction fit surgical implant (690) are provided with four distinct regions. First region (616) guides threadless friction fit surgical implant (690) into the target zone of the surgically created cavity. First Region (616) has a blunt tip (618) leading edge in front and connects posteriorly to second region (626*p*). The respective heights and respective widths of threadless friction fit surgical implant (690) in first region (616) are less than any height or width in second region (626*p*). The threadless friction fit surgical implant (690) in second region (626*p*) can have dimensions that maximize surface contact area with the geometric dimensions of the target zone and the subcortical bone within a pedicle. Second region (626*p*) is connected to first region (616) and third region (636*p*). Third region (636*p*) can correspond to the area in between the pedicle and the mammillary process. Wings or bulges (670) can be incorporated into third region (636*p*). Bends or curves can be incorporated into fourth region (646). First region (616), second region (626*p*) and third region (636*p*) share a common midline (M-M). Fourth region (646) can share the common midline (M-M) or fourth region (646) can be provided with secondary midline (M1-M1) that is offset of up to about 45 degrees from the common midline (M-M). It is believed that offsetting the fourth region (646) can improve connections with some devices distinct from threadless friction fit surgical implant (690).

Threadless friction fit surgical implant (690) is provided with a first region (616), a second region (626*p*), a third region (636*p*) and a fourth region (646) where the regions (616, 626*p*, 636*p*, 646) are interconnected.

A preferred embodiment of threadless friction fit surgical implant (690) includes conduit (624) adapted to carry one or more biocompatible substances. Conduit (624) traverses first region (616), second region (626*p*) and third region (636*p*). Barrier (626) also surrounds conduit (624). In select preferred embodiments, conduit (624) can traverse fourth region (646) and barrier (626) surrounds fourth region (646). First region (616) includes a blunt tip (618). Outward dimensions of first region (616) are nearer to the conduit (624) than outward dimensions of the second region (626*p*) and third region (636*p*). Third region (636*p*) can be provided with one or more wings or bulges (637) incorporated with the barrier (626) where the wings (637) correspond to a target zone for implantation. Rough surfaces (632) can be applied to first region (616), second region (626*p*) and third region (636*p*). Patient-specific implant (690) can be provided with one or more openings (642) allowing interactions between conduit (624) and the target zone or surgically created environment proximate patient-specific implant (690). Fourth region (646), without rough surfaces (632), is connectable to a device distinct from patient-specific implant (690). Rough surfaces (632) can include micropores, metal, abrasive particles, dense particles or clumps of particles. Polyaxial head (100) can be connected to fourth region (646). Fourth region (646) can be provided with secondary midline (M1-M1) that is offset of up to about 45 degrees from the common midline (M-M) of first region (616), second region (626*p*) and third region (636*p*). In select preferred embodiments, the fourth region (646) can include rough surfaces (632) and the first region (616), the second region (626*p*) and the third region (636*p*) have more of the rough surfaces (632) than the fourth region (646).

Another preferred embodiment of patient-specific implant (690) includes an uninterrupted exterior (692). First region (616) includes a blunt tip (618). Outward dimensions of first region (616) are nearer to the conduit (624) than outward dimensions of the second region (626*p*) and third region (636*p*). Third region (636*p*) can be provided with one or more wings or bulges (637) uninterrupted exterior (692) where the wings (637) correspond to a target zone for implantation. Rough surfaces (632) can be applied to first region (616), second region (626*p*) and third region (636*p*). Fourth region (646), without rough surfaces (632), is connectable to a device distinct from threadless friction patient-specific implant (690). Rough surfaces (632) care created by either additive or subtractive means or a combination thereof and can include micropores, metal, abrasive particles, dense particles or clumps of particles. Polyaxial head (100) can be connected to fourth region (646). Fourth region (646) can be provided with secondary midline (M1-M1) that is offset of up to about 45 degrees from the common midline (M-M) of first region (616), second region (626*p*) and third region (636*p*). In select preferred embodiments, the fourth region (646) can include rough surfaces (632) and the first region (616), the second region (626*p*) and the third region (636*p*) have more rough surfaces (632) than the fourth region (646).

FIGS. 27*a*-27*f* show lateral perspectives of preferred embodiments of patient-specific implants (690) shown in FIGS. 26*a*-26*f* that also include rough surfaces (632).

Within the scope of the invention, there are an unlimited number of patient-specific spinal fixation devices (600) that can be manufactured by the current process (123). Examples of patient-specific spinal fixation devices (600) manufactured by the process (123) can include, but are not limited to, threaded conical and threadless porous ingrowth pedicle fixation devices.

Preferred Steps of the Process (123) of Making a Patient-Specific Implant

Depending on patient's (30) medical condition(s), metric output (408) of the current process can adjust manufacturing apparatus (500) to manufacture patient-specific implant(s) (600) that fit exactly into the target zone(s) (40), are slightly larger or smaller than target zone(s) (40) and/or add new additional structures associated with the three dimensional geometric representations (42) of the target zone (40). A user of the current process can utilize a visual display to adjust the metric output (408) before transfer to the manufacturing apparatus (500), e.g., structures can be added or deleted from manufactured patient-specific implant (600). For example, the metric output (408) correlated with patient's (30) X, Y and Z axes, three dimensional geometric representations (42) of the target zone (40) and volume of target zones (40) can cause manufacturing apparatus (500) to add such additional structures as apertures, overlaps, surface treatments or rough surfaces (632), and wings (637), etc. For select embodiments of the current invention, in view of the aggregate of medical histories, clinical observations and medical test results for multiple patients, the process (123) of making a patient-specific implant can suggest a patient-specific composition, volume, length, depth and/or additional structures of an implant that is tailored specifically for the patient having identical or similar medical history, test results and clinical observations.

The process (123) of making a patient-specific implant (series 600) for a patient (30) can include, but is not limited to, one or more scanners or scanning devices (100), communications devices (200), communications networks (300), computing devices, cloud computing or a combination thereof (400), aggregate (450) of encrypted and tagged information, manufacturing apparatus (500) and computerized navigation system (800). It is anticipated that communication networks (300) will interconnect the computing devices, cloud computing or a combination thereof (hereinafter computers (400)) and scanners (100), communications devices (200), manufacturing apparatus (500) and computerized navigation system (800) that are situated at locations distinct from computers (400). However, the current invention can also function with scanning devices (100), communication networks (300), computers (400), manufacturing apparatus (500) and computerized navigation system (800) located at a centralized location such as a hospital.

FIGS. 1-6 portray representations of sagittal (X-axis), coronal (Y-axis) and transverse planes (Z-axis) of a portion of the spine. In particular, patient (30) presents with a L4-5 spondylolisthesis. Medical scans (102) of target zones (40) were for some of the pedicles (902) of patent's (30) vertebra (920). As shown, target zones (40) of the pedicle (902) are round, oval and oblong. In select embodiments of the present invention, the aggregate of encrypted and tagged information (450) can generate a metric output (408) that causes the manufacturing apparatus (500) to make round, oval and oblong patient-specific implants (600) fit exactly into their target zone(s) (40) with only surface treatments (632) applied to first, second and third regions (616, 626p, 636p) of implant (600). If the surgeon's medical judgments were that different designs would improve safety during insertion or distribute postoperative stress loads over a greater surface area, the surgeon can use communication device (200) to adjust the metric output (408). By way of illustration, the surgeon's input can adjust the metric output (408) to cause manufacturing apparatus (500) to make the round patient-specific implant (600) to not have surface treatments (632) and be slightly larger than its target zone (40) and the oval patient-specific implant (600) to have no threads, have surface treatments (632) and fit exactly into its target zone (40).

Within the ambit of the present invention, the current process (123) of making a patient-specific implant (series 600) for a patient (30) can include target zone(s) (40) that are associated with the spine. Target zone (40) can include patient's (30) tissue that is proximate to patient-specific implant (600) after the patient-specific spinal device (600) is surgically implanted into patient (30). Depending on the type of patient-specific implant (600) utilized, the patient's (30) tissue may or may not be surgically altered prior to implantation.

Within the scope of the current process (123), the combination of memory (402), software (404) and processor (406) can publish reports. Reports 425 can be directed to the manufactured patient-specific implant (600) and target zone (40) and include, strength, dimensions, required implantation force, visual three dimensional representations (42), customizable options, risk of iatrogenic fracture, etc. Reports (426) can be associated with the outcomes of patient-specific implants (600) and can assist in patient care, hospital efficiency, and manufacturing. Educational reports (427) can compare different adjunct medical treatments of patients receiving patient-specific implants (600) made by the current process (123) can be generated.

Figure 28:
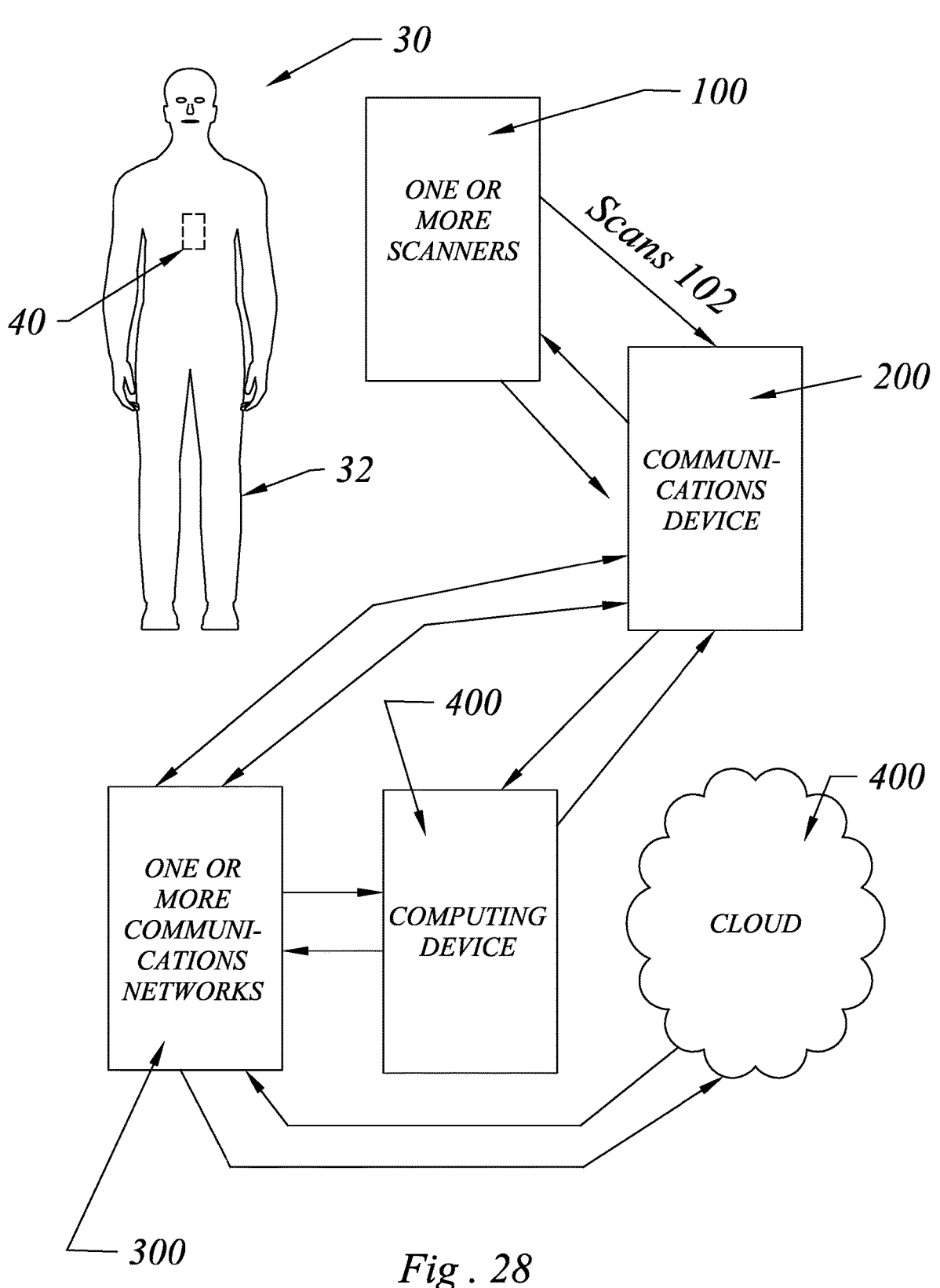
FIGS. 28-30 disclose select embodiments of combinations of hardware and software associated with the steps of process (123).
Figure 29:
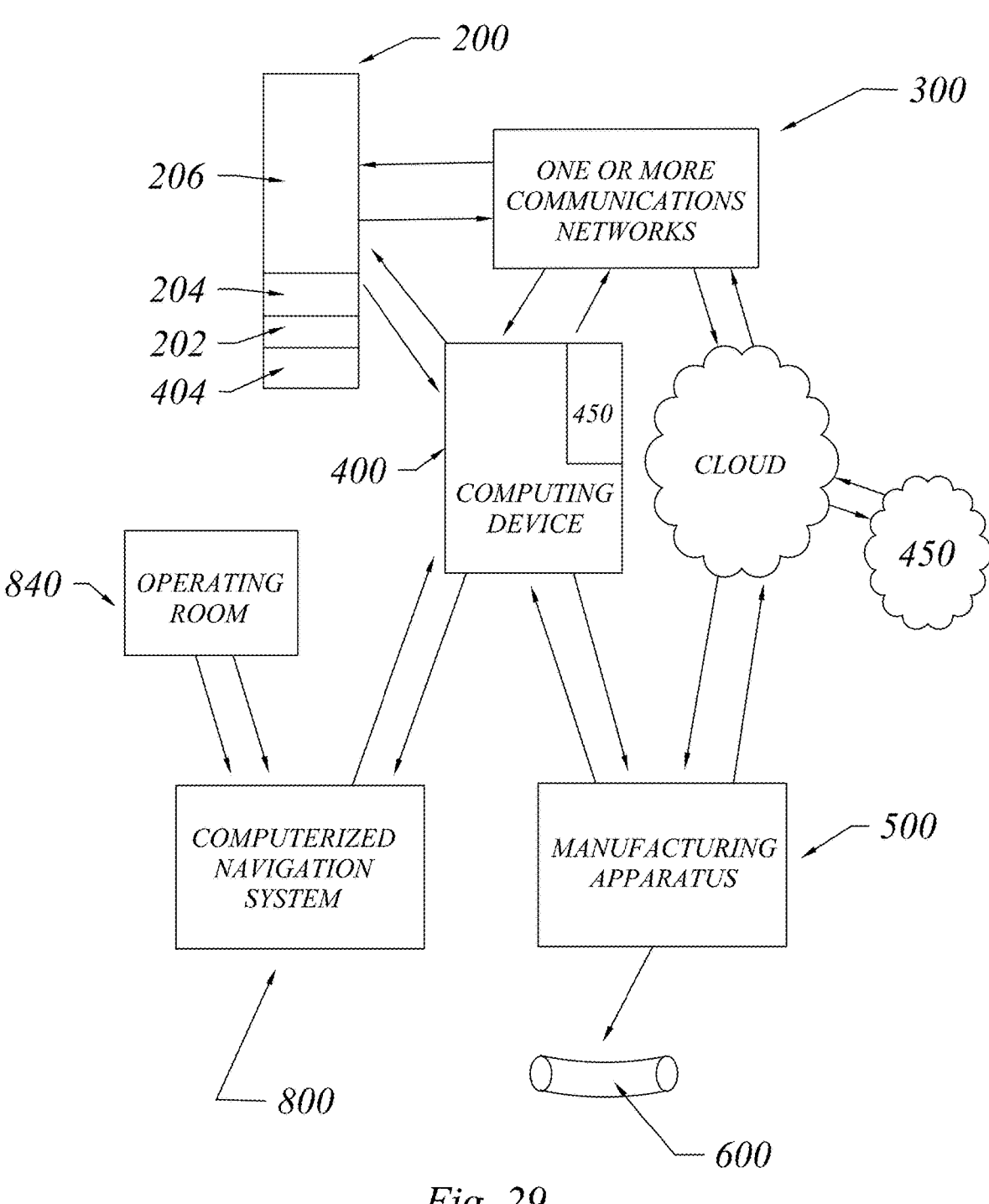
Figure 30:
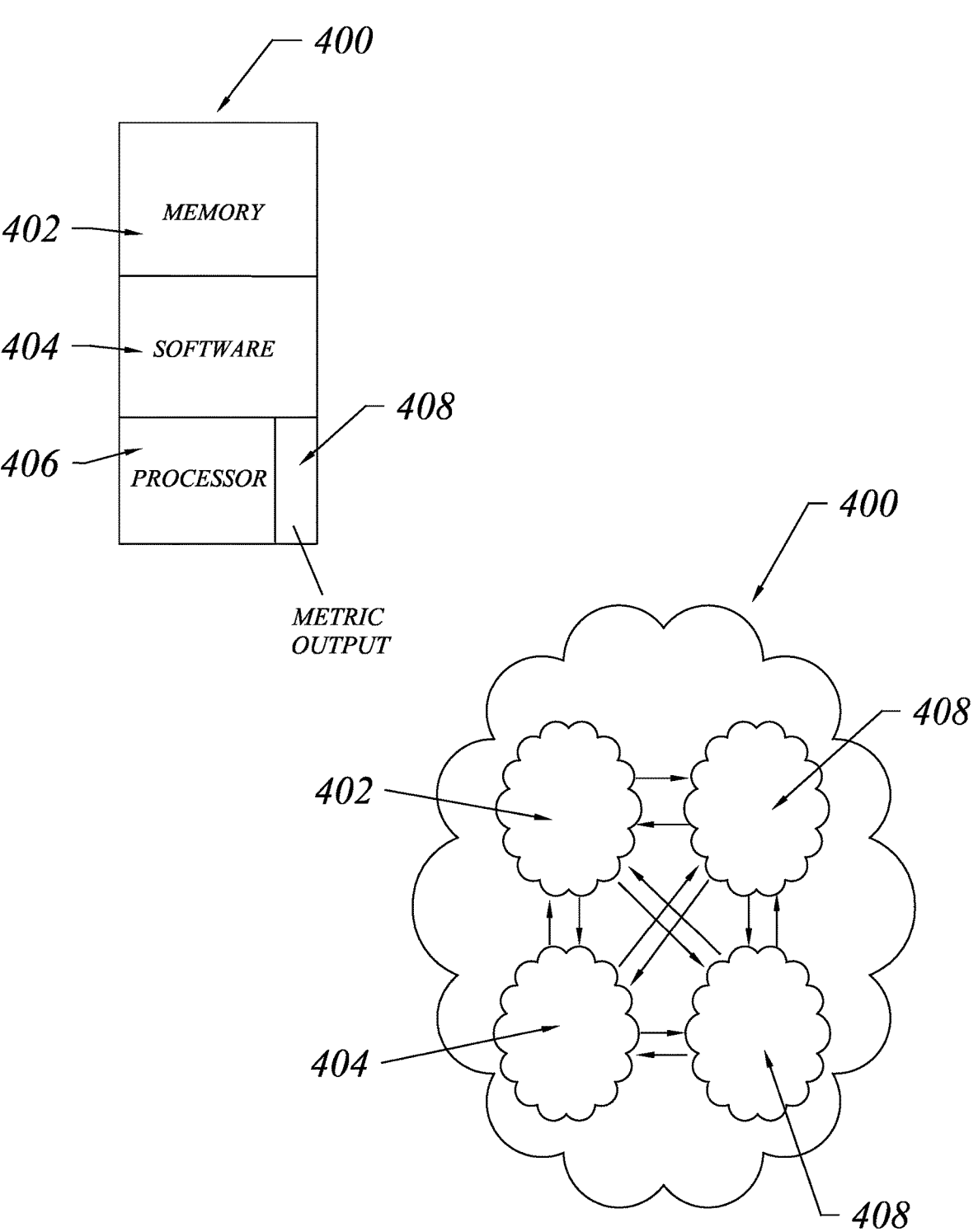

Select Embodiments of Hardware and Software Associated with Process (123) Disclosed in FIGS. 28-30.

I) A First Embodiment of the Process (123) of Making a Patient-Specific Implant (600).

Scanners (100) are adapted to intercommunicate with one or more communications devices (200). Communication devices (200) can be integral with scanners (100) or distinct from scanners (100), and within the scope of the current process of making a patient-specific implant (600) for a patient (30), communications between scanners (100) and one or more communications devices (200) can be bidirectional.

In accordance with the current process (123) of making a patient-specific implant (600) for a patient (30), scanners or scanning devices (100) utilize one or more scanning techniques selected from the group consisting of X-rays, computerized tomography (CT), magnetic resonance imaging (MRI) and dual-energy X-ray absorptiometry (DEXA), ultrasound, or any other scanning technique acceptable in the art that can be utilized to scan target zone (40).

Communications devices (200) compatible with the current process of making a patient-specific implant (600) for a patient (30) can include desktop computers, tablet computers, smart phones or any other device, acceptable in the art, capable of encrypting, sending and receiving data. Preferred communications devices (200) can be provided with communications processor (202), store (204) and visual display (206). Hereinafter, "communications processor" (202) refers to any processor associated with a communications device (200) and "store" (204) refers to any memory associated with a communications device (200).

Communications devices (200) can intercommunicate with each other and one or more communications networks (300) that can transfer bidirectional communications between communications devices (200) and computers (400). Networks (300) compatible with the current process of making a patient-specific implant (600) for a patient (30) include radio frequency, the Internet, the PTSN, a LAN, a WAN, VoIP, wired communications, wireless communications, any combination thereof or any other network acceptable in the art. All devices and systems of the current process of making a patient-specific implant (600) for a current patient (30) are provided with the necessary workings that allow intercommunications with other devices and systems of the current invention.

For select preferred embodiments, instead of using a network (300), one or more communications devices (200) can intercommunicate directly with one of the computers (400). Other select preferred embodiments of communications devices (200) that include software (404) can intercommunicate directly with manufacturing apparatus (500).

Among other things, computers (400) are provided with memory (402), software (404) and processor (406). Processor (406) and software (404) calculate metric output (408) utilized by manufacturing apparatus (500) to make patient-specific implant (600). For selected computers (400), memory (402) can include RAM and ROM.

Depending on preselected parameters, computers (400) can intercommunicate with manufacturing apparatus (500) and deliver software (404) calculated metric output (408) to manufacturing apparatus (500). Metric output (408) directs manufacturing apparatus (500) to manufacture patient-specific implant (600) for patient (30) according to the specifications of metric output (408). In select preferred embodiments of the process of making a patient-specific implant (600) for a patient (30), communications device (200) can be used to adjust metric output (408) before transfer to the manufacturing apparatus (500).

Among other things, computers (400) and software (404) correlate medical scans (102) from various diverse scanners' (100) scans (102) of the locations the target zones (40) with X, Y and Z axes of the patient (30). This correlation of data with X, Y and Z axes of the patient (30) allows software (404) and computers (400) to create viewable three dimensional geometric representations (42) of the current patient's (30) target zone (40) and generate one or more metric outputs (408).

For select preferred embodiments, a combination of one or more of three dimensional geometric representations (42) of the current patient's (30) target zone (40) and the selected metric output (408) for patient-specific implant (600) can be communicated to a computerized navigation system (800) in an operating room (840) for assisting with the implantation of patient-specific implant (600) into the patient's (30) target zone (40).

Within the scope of the current invention, manufacturing apparatus (500) can utilize one or more of the following methodologies of acid etching, milling, molding, printing, 3-D printing or welding, or any other manufacturing methodology acceptable in the art to make the patient-specific implant (600). Optionally, software (404) can cause manufacturing apparatus (500) to manufacture a model of target zone 40.

Patient-specific implants (600) of the current process are manufactured in compliance with a registry of government approved safe and effective implants for implantation into patients (30). Examples of governmental agencies approving implants for implantation into humans include the US Food and Drug Administration, the Brazilian National Health Surveillance Agency, Health Canada, the China National Medical Products Administration, the European Commission, the Indian Central Drug Standards Control Organisation, the Japanese Pharmaceuticals and Medical Devices Agency, the Philippines Food and Drug Administration and the Russian List of Essential Implantable Medical Devices.

When operating parameters require, software (404) causes the calculated metric output (408) to add surface treatments or roughness (632) to patient-specific implant (600). Surface treatments (632) can be applied to one or more sections of patient-specific implant (600) to increase frictional resistance to movement. Manufacturing apparatus (500) can be utilized to create micropores and/or barbs, etc. on surfaces of patient-specific implant (600). Surface treatments (632) can be created by multi-level printing abrasive devices, chemical, laser, metal or abrasive particles incorporated into or onto the patient-specific implant (600) or by other means acceptable in the art.

When medical conditions require, software (404) causes the calculated metric output (408) to add additional structures to patient-specific implant (600). Examples of additional structures include but are not limited to: apertures, cannulas, fenestrations, meshes, ridges, threads and wings (637). In the alternative, when medical engineering parameters require, software (404) causes the calculated metric output (408) to create a patient-specific implant (600) with smooth external surfaces.

Within the scope of the current process, biocompatible substances used to make patient-specific implants (600) include, but are not limited to, titanium alloys, stainless steel, cobalt-chrome, shape memory metals, shape memory polymers, non-resorbable polymers, any combination thereof, or any composition or material acceptable in the art.

With respect to data encryption associated with the process of making a patient-specific implant (600) for a patient (30), Hypertext Transfer Protocol Secure (HTTPS) or another protocol acceptable in the art can be utilized to encrypt data transmissions between communications devices (200), networks (300), computers (400) and manufacturing apparatus (500). After any data/information is entered into the current process of making a patient-specific implant (600) for a patient (30), one or more communication protocols secure the encrypted data/information in regards to any Cloud or Non-Cloud communications associated with preoperative, operative, postoperative, manufacturing, navigational, scanning or computing communication/intercommunication associated with the present invention.

II) Second Embodiment of the Process (123) of Making a Patient-Specific Implant (600).

Communications networks (300), computers (400) are adapted to communicate with each other. Among other things, computers (400) include processor (406), memory (402) and software (404). Memory (402) is adapted to securely contain an aggregate (450) of encrypted and tagged information correlated with patient-specific implants (600) previously implanted into prior patients (30) and manufactured by the process of making a patient-specific implant (600) for a current patent (30).

Aggregate (450) of encrypted and tagged information can include one or more of the following:

correlation of medical scans (102) and locations of the target zones (40) with X, Y and Z axes of the prior patients (30); the target zones (40);

three dimensional geometric representations (42), with or without implants (600), of the prior patients' (30) target zones (40);

prior patients' (30) medical histories, clinical observations and medical test results;

prior patients' (30) metric outputs (408) for the dimensions of prior patients' patient-specific implants (600); and/or a registry of government approved safe and effective implants available for implantation into patients.

In select preferred embodiments of the process of making a patient-specific implant (600) for a current patient (30), preoperative, operative and postoperative medical histories, medical conditions, clinical observations, medical tests and/or surgical outcomes of patients (30) previously receiving patient-specific implants (60) are added into the aggregate (450) of encrypted and tagged information. In other preferred embodiments of the process of making a patient-specific implant (600) for a current patient (30), aggregate (450) can include such information as identities of surgeons, physicians and medical facilities and dates where patient-specific implants (600) were implanted into patients (30).

Processor (406) and software (404) can be programmed to accumulate additional predetermined information for aggregate (450). In accordance with the current invention, the combination of processor (406) and software (404) provide search capabilities of the aggregate (450) of encrypted and tagged information.

Scanners (100) are adapted to intercommunicate with one or more communications devices (200). Communication devices (200) can be integral with scanners (100) or distinct from scanners (100). Within the scope of the current process of making a patient-specific implant (600) for a patient (30), communications between scanners (100) and one or more communications devices (200) can be bidirectional.

In accordance with the current process (123) of making a patient-specific implant (600) for a patient (30), scanners or scanning devices (100) utilize one or more scanning techniques selected from the group consisting of X-rays, computerized tomography (CT), magnetic resonance imaging (MRI) and dual-energy X-ray absorptiometry (DEXA), ultrasound, or any other scanning technique acceptable in the art that can be utilized to scan target zone (40).

Communications devices (200) compatible with the current process of making a patient-specific implant (600) for a patient (30) can include desktop computers, tablet computers, smart phones or any other device, acceptable in the art, capable of encrypting, sending and receiving data. Preferred communications devices (200) can be provided with communications processor (202), store (204) and visual display (206). As indicated above, "communications processor" (202) refers to any processor associated with a communications device (200) and "store" (204) refers to any memory associated with a communications device (200).

Communications devices (200) can intercommunicate with each other and one or more communications networks (300) that can transfer bidirectional communications between communications devices (200) and computers (400). Networks (300) compatible with the current process (123) of making a patient-specific implant (600) for a patient (30) include radio frequency, the Internet, the PTSN, a LAN, a WAN, VoIP, wired communications, wireless communications, any combination thereof or any other network acceptable in the art. All devices and systems of the current process (123) of making a patient-specific implant (600) for a current patient (30) are provided with the necessary workings that allow intercommunications with other devices and systems of the current invention.

For select preferred embodiments, instead of using network (300), one or more communications devices (200) can intercommunicate directly with one of the computers (400). Other select preferred embodiments of communications devices (200) that include software (404) can intercommunicate directly with manufacturing apparatus (500).

Among other things, computers (400) are provided with memory (402), software (404) and processor (406). Processor (406) and software (404) calculate metric output (408) utilized by manufacturing apparatus (500) to make patient-specific implant (600). Memory (402) can include RAM and ROM.

Depending on preselected parameters, computers (400) can intercommunicate with manufacturing apparatus (500) and deliver software (404) calculated metric output (408) to manufacturing apparatus (500). Metric output (408) directs manufacturing apparatus (500) to manufacture patient-specific implant (600) for patient (30) according to the specifications of metric output (408). In select preferred embodiments of the process of making a patient-specific implant (600) for a patient (30), metric output (408) can be adjusted before transfer to manufacturing apparatus (500).

Among other things, computers (400) correlate medical scans (102) from the various diverse scanners' (100) scans (102) of the locations the target zones (40) with X, Y and Z axes of the patient (30). This correlation of data with X, Y and Z axes of the patient (30) allows software (400) and computers (400) to create viewable three dimensional geometric representations (42) of the current patient's (30) target zone (40) and generate metric output (408). Select embodiments of the present process can calculate the X, Y and Z axes relative to a specific vertebral body (901) to further sub-classify aggregate (450) and improve overall search precision of aggregate (450).

For select preferred embodiments, a combination of one or more of three dimensional geometric representations (42) of the current patient's (30) target zone (40) and the selected metric output (408) for patient-specific spinal fixation device (600) can be communicated to a computerized navigation system (800) in an operating room (840) for assisting with the implantation of patient-specific spinal fixation device (600) into the patient's (30) target zone (40).

Within the scope of the current invention, manufacturing apparatus (500) can utilize one or more of the following methodologies of acid etching, milling, molding, printing, 3-D printing, welding, or any other methodology acceptable in the art, to make the patient-specific implant (600). Optionally, software (404) can cause manufacturing apparatus (500) to manufacture a model of target zone 40.

Patient-specific implants (600) of the current process (123) are manufactured in compliance with a registry of government approved safe and effective implants for implantation into patients (30). Examples of governmental agencies approving implants for implantation into humans include the US Food and Drug Administration, the Brazilian National Health Surveillance Agency, Health Canada, the China National Medical Products Administration, the European Commission, the Indian Central Drug Standards Control Organisation, the Japanese Pharmaceuticals and Medical Devices Agency, the Philippines Food and Drug Administration and the Russian List of Essential Implantable Medical Devices.

When operating parameters require, software (404) causes the calculated metric output (408) to add surface treatments or roughness (632) to patient-specific implant (600). Surface treatments (632) can be applied to one or more sections of patient-specific implant (600) to increase frictional resistance to movement and facilitate bone ingrowth. Manufacturing apparatus (500) can be utilized to create micropores (632) and/or barbs, etc. on surfaces of patient-specific implant (600). Surface treatments (632) can be created by multilayer printing, abrasive devices, chemical, laser, metal or abrasive particles incorporated into or onto the patient-specific implant (600) or by other means acceptable in the art.

When medical conditions require, software (404) causes the calculated metric output (408) to add additional structures to patient-specific implant (600). Examples of additional structures include but are not limited to: apertures, cannulas, fenestrations, meshes, ridges, threads and wings (637). In the alternative, when medical engineering parameters require, software (404) causes the calculated metric output (408) to create a patient-specific implant (600) with smooth external surfaces.

Within the scope of manufacturing, biocompatible substances used to make patient-specific implants (600) include, but are not limited to, titanium alloys, stainless steel, cobalt-chrome, shape memory metals, shape memory polymers, non-resorbable polymers, any combination thereof, or any composition or material acceptable in the art.

With respect to data encryption associated with the process of making a patient-specific implant (600) for a patient (30), Hypertext Transfer Protocol Secure (HTTPS) or another protocol acceptable in the art can be utilized to encrypt data transmissions between communications devices (200), networks (300), computers (400) and manufacturing apparatus (500). After any data/information is entered into the current memory (402) for a patient (30), one or more communication protocols secure the encrypted data/information in regards to any Cloud or Non-Cloud communications associated with preoperative, operative, postoperative, manufacturing, navigational, scanning or computing communication/intercommunication associated with the present invention.

Those skilled in the art recognize that the below identified steps of the processes (123) of making a patient-specific implant can occur simultaneously or a different order and still achieve the identical end result for the patient-specific implant (600).

Among other things, FIGS. 31-55 enable the processes (123) of making a patient-specific implant. Process steps 123-100-process steps 123-312 are enabled in FIGS. 31-55.

What is claimed is:

1. A computer-implemented process for manufacturing a customized patient-specific fixation device, the process comprising the steps of:

a) using one or more medical scanners selected from the group consisting of X-rays, ultrasound, computerized tomography (CT), magnetic resonance imaging (MRI), dual-energy X-ray absorptiometry (DEXA) to generate one or more patient-specific digitized medical scans of a target zone of a patient's vertebrae;

b) encrypting communications from the one or more medical scanners to communication devices, computers and manufacturing apparatus and decrypting communications received by the communications devices, computers and manufacturing apparatus;

c) tagging, sending and securely storing patient information in a non-transitory memory regarding:

i) scans of the one or more patient-specific digitized medical scans of a target zone; and ii) medical history, current medical conditions, clinical observations and/or medical test results;

d) executing a processor and a software to process the patient information and generate:

i) relative to a center of the patient's spinal canal proximate to the target zone, a patient-specific coordinate correlating the one or more patient-specific digitized medical scans and a location of the target zone with X, Y and Z axes associated with the patient-specific coordinate; and ii) one or more three dimensional geometric models providing precise measurements of the target zone, one or more metric outputs and physician options for selecting the patient-specific fixation device for manufacture, wherein the physician options include making the patient-specific device according one of the metric outputs comprising two or more connected distinct regions, and wherein the three dimensional geometric models, metric outputs and physician options are viewable on one or more displays;

e) securely transmitting the customized patient-specific fixation device design parameters from the computer system to a first manufacturing apparatus;

f) operating the first manufacturing apparatus to create the customized patient-specific fixation device comprising one or more biocompatible materials, wherein the manufacturing apparatus is directly controlled by the customized fixation device implant design parameters to create the two or more distinct, interconnected regions conforming to the patient's target zone; and g) optionally, operating a second manufacturing apparatus to create a physical model of the target zone based on the three-dimensional digital model.

2. The computer-implemented process of claim 1, wherein the customized patient-specific fixation device created by the first manufacturing apparatus further comprises: a first discernable region, a second discernable region, a third discernable region and a fourth discernable region, wherein at least one of the regions is connectable to a device distinct from the customized patient-specific fixation device.

3. The computer-implemented process of claim 2, wherein the computer system is further configured to:

a) spatially arrange the first discernable region, the second discernable region and the third discernable region to share a common midline M-M, wherein the common midline is geometrically defined relative to a central axis of a pedicle in the target zone in the three-dimensional digital model; and b) spatially arrange the fourth discernable region to share the common midline M-M or create a secondary midline M1-M1 between the third discernable region and the fourth discernable region such that midline M1-M1 is offset at an angle of about forty-five degrees from the common midline M-M.

4. The computer-implemented process of claim 3, wherein the computer system is further configured to generate implant design parameters such that the first manufacturing apparatus creates a customized patient-specific fixation device comprising:

a) a fourth discernable region designed with a geometry for secure connection to one or more surgical devices distinct from the patient-specific implant;

b) a third discernable region having a surface contour defined by a plurality of bulges, serrations, or wings that are computationally optimized to inhibit over-insertion of the customized patient-specific fixation device, increase the surface area for bone ingrowth, dissipate loads transmitted from adjacent levels proximate the target zone and a connector for coupling devices distinct from the customized patient-specific fixation device;

c) a second discernable region designed with a decreasing contour that is computationally derived from the three-dimensional digital model to i) improve surface contact area of the customized patient-specific fixation device with the pedicle's subcortical bone and bone ingrowth;

ii) enhance friction, anatomical grip and stability of the customized patient-specific fixation device; and iii) distribute loads over a larger surface area, and the likelihood of bone ingrowth; and d) a first discernable region designed with a taper from the second region to a blunt tip, wherein the taper is computationally defined by the pedicle's geometry to facilitate insertion through a smallest section of the pedicle.

5. The computer-implemented process of claim 4, wherein the computer system is further configured to incorporate one or more of the following into the customized patient-specific fixation device implant design parameters:

a) at least one conduit that is computationally defined with a smooth or roughened surface through a specified region of the customized patient-fixation fixation device;

b) a plurality of openings that are computationally positioned and sized to facilitate the customized patient-specific fixation device stabilization and bone ingrowth stabilization via injection of adhesives or fusion accelerating substances through the conduit; and c) a surface treatment that is computationally applied to a specified region of the customized patient-specific fixation device, wherein the surface treatment modifies the surface topography or chemistry to enhance adhesion and anatomical integration.

6. The computer-implemented process of claim 5, wherein the computer system is further configured to:

a) identify a specific volume of a subcortical bone within the pedicle from the three-dimensional digital model of the patient's target zone;

b) computationally simulate the stress on the patient's vertebrae during surgical implantation of the patient-specific implant using the three-dimensional model to generate a predictive biomechanical stress analysis; and c) generate a tangible output report on a visual display that includes patient-specific force-displacement graphs and stress contour maps for the proposed surgical plan, thereby providing a surgeon with a quantitative assessment of implant stability prior to the physical implantation.

7. The computer-implemented process of claim 6, wherein the computer system is further configured to:

a) generate a computer-assisted surgical guide as a digital outcome report, viewable on one or more visual displays, wherein the surgical guide comprises patient-specific anatomical landmarks and real-time intraoperative metrics derived from the three-dimensional digital model to assist with the surgical implantation of the customized patient-specific fixation device into the target zone; or b) transmit a physician approved metric output to a computerized navigation system for computational alignment of the customized patient-specific fixation device's three-dimensional model with the target zone in real time during a surgical procedure; and c) anonymize the patient information and computationally merge the anonymized information with an aggregate of similar patient data in the non-transitory memory, wherein the aggregate is subsequently used to improve the computational digital outcome reports defining the customized patient-specific fixation device's geometry, dimensions, surgical plans and other surgical options.

8. A computerized system for manufacturing a patient-specific spinal implant, the method comprising the steps of:

a) generating one or more three-dimensional digital models of a current patient's target zone and surrounding tissues by computer processing scan data from one or more scanners selected from the group consisting of X-rays, ultrasound, computerized tomography (CT), magnetic resonance imaging (MRI), and dual-energy X-ray absorptiometry (DEXA);

b) encrypting communications from the one or more medical scanners to communication devices, computers and manufacturing apparatus and decrypting communications received by the communications devices, computers and manufacturing apparatus;

c) tagging, sending, and securely storing patient information in a non-transitory memory regarding:

i) one or more three-dimensional digital models;

ii) patient-specific digitized medical scans of a target zone; and iii) medical history, current medical conditions, clinical observations and/or medical test results;

d) executing a processor and a software to process the patient's information and access an aggregate of prior patients' information to generate:

i) a first set of patient-specific metrics relative to a center of the patient's spinal canal proximate to the target zone and a patient-specific coordinate correlating the one or more patient-specific digitized medical scans and a location of the target zone with X, Y and Z axes associated with the patient-specific coordinate;

ii) three-dimensional geometric representations and measurements of prior patients' target zones;

iii) metric outputs for: patient-specific implants previously manufactured and implanted into the prior patients; and previously submitted surgical options and accompanying probabilities of successful outcomes;

iv) post-operative medical histories and clinical observations associated with the previously implanted patient-specific implants; and v) correlating previous metric outputs associated with a specific surgeon's use of the specific surgeon's previously implanted patient-specific implants;

e) using the computer executing the processor to compare and correlate the first set of patient-specific metrics from the current patient with the aggregate to generate a second set of optimized metric outputs, wherein the second set of optimized metric outputs is specifically tailored to the current patient based on successful outcomes in prior patients;

f) connecting a visual display to the computer system, the visual display configured to present the first set of metrics from the current patient and the aggregate to generate the second set of optimized metrics and physician options for the patient-specific spinal implant;

g) transferring a physician-approved metric output, selected from the first set of metrics and the second set of optimized metric outputs, to a manufacturing apparatus; and h) controlling the manufacturing apparatus with the physician-approved metric output to physically fabricate the patient-specific spinal implant from one or more biocompatible materials.

9. The computerized system of claim 8, wherein the patient-specific spinal implant is a tangible object having a first region, a second region, a third region, and a fourth region, and further wherein at least one of the regions is structurally configured to be physically coupled to a device distinct from the patient-specific implant.

10. The computerized system of claim 9, wherein the patient-specific spinal implant has a structure characterized by:

a) a fourth region that is structurally configured to be physically coupled to a device distinct from the patient-specific spinal implant;

b) a third region that physically comprises bulges, serrations or wings that inhibit over-insertion of the patient-specific spinal implant, increases the surface area for bone ingrowth, and dissipate loads transmitted from adjacent levels proximate the target zone;

c) a second region that improves surface contact area of the patient-specific spinal implant with the pedicle's subcortical bone and bone ingrowth; and d) a first region that physically tapers from the second region to a blunt tip.

11. The computerized system of claim 10, wherein the manufacturing apparatus is further configured to fabricate the patient-specific spinal implant with one or more of the following physical features: conduits, openings, or surface treatments, as determined by the physician-approved metric output.

12. The computerized system of claim 11, wherein the conduits, openings, and surface treatments are fabricated with a specific geometry and physical dimensions based on the physician-approved metric output to promote biological ingrowth into the patient-specific spinal implant.

13. The computerized system of claim 12, wherein the manufacturing apparatus is further configured to fabricate the patient-specific spinal implant with at least one physical region that is specifically shaped to conform to a subcortical bone within a pedicle.

14. The computerized system of claim 13, wherein the manufacturing apparatus is further configured to:

a) spatially arrange the first region, the second region and the third region to share a common midline M-M, wherein the common midline is geometrically defined relative to a central axis of the patient-specific spinal implant; and b) spatially arrange the fourth region to share the common midline M-M or create a secondary midline M1-M1 between the third discernable region and the fourth discernable region such that midline M1-M1 is offset at an angle of about forty-five degrees from the common midline M-M.

15. The computerized system of claim 14, wherein the manufacturing apparatus is further configured to physically fabricate the patient-specific spinal implant such that the common midline M1-M1 of the third region and the fourth region is physically offset at an angle of up to about 30 degrees from the common midline M-M of the first region and the second region, resulting in a physically angled patient-specific implant.

16. The computerized system of claim 13, further configured to:

a) generate an outcome report on the visual display that includes three-dimensional visual guidance and specific physical alignment metrics for assisting a surgeon with the freehand implantation of the patient-specific spinal implant into the target zone; or b) transmit the physician-approved metric output to a dedicated and specialized computerized navigation system for providing real-time, physical guidance during the implantation of the patient-specific implant into the target zone;

c) accessing the aggregate comprising:

i) three-dimensional geometric representations and measurements of prior patients' target zones;

ii) metric outputs for:

patient-specific implants previously manufactured and implanted into prior patients; and previously submitted surgical options including identification of probabilities of successful outcomes; and iii) post-operative medical histories and clinical observations associated with previously implanted patient-specific implants.

17. A process for manufacturing an optimal patient-specific three-dimensional implant for a target zone in a current patient, the process comprising the steps of:

a) using one or more medical scanners selected from the group consisting of X-rays, ultrasound, computerized tomography (CT), magnetic resonance imaging (MRI), dual-energy X-ray absorptiometry (DEXA) to generate one or more patient-specific digitized medical scans of a target zone;

b) encrypting communications from the one or more medical scanners to communication devices, computers and manufacturing apparatus and decrypting communications received by the communications devices, computers and manufacturing apparatus;

c) tagging, sending, and securely storing patient information in a non-transitory memory regarding:

i) one or more patient-specific digitized medical scans of a target zone relative to X, Y, and Z axes of the target zone; and ii) medical history, current medical conditions, clinical observations, and/or medical test results;

d) executing a software causing a processor to:

i) process the medical scans to generate a patient-specific three-dimensional model of the target zone in the current patient and thereafter adding the patient-specific three-dimensional model to an aggregate of historical implant and outcome data from prior patients;

ii) compare the patient-specific three-dimensional model with the aggregate of historical implant and outcome data from prior patients, wherein the aggregate includes three-dimensional geometric representations of prior patients' target zones and associated measurements;

iii) calculate a first set of patient-specific metric outputs for designing the optimal patient-specific three-dimensional implant based solely on the patient-specific three-dimensional model of the target zone in the current patient;

iv) to calculate a second set of optimized metric outputs by analyzing the first set of patient-specific metric outputs in view of the aggregate of historical implant and outcome data to improve the fit and performance of the optimal patient-specific three-dimensional implant;

e) transmitting a metric selected from the first and second sets to a manufacturing apparatus, wherein the manufacturing apparatus is a three-dimensional printer, for the fabrication of the optimal patient-specific three-dimensional implant; and f) controlling the manufacturing apparatus to physically fabricate the optimal patient-specific three-dimensional implant from one or more biocompatible materials.

18. The process of making the optimal patient-specific three-dimensional implant of claim 17, wherein the optimal patient-specific three-dimensional implant comprises a first second and a second section opposed to the first section and the second section is tapered such that the cross-sectional area of the optimal patient-specific three-dimensional area is less proximate the patient's target zone.

19. The process of making the optimal patient-specific three-dimensional implant of claim 18, wherein the metric for fabricating the optimal patient-specific three-dimensional implant generates simultaneously a conduit extending through the optimal patient-specific three-dimensional implant about the longitudinal axis of the optimal patient-specific three-dimensional implant during the 3D printing process.

20. The process of making the optimal patient-specific three-dimensional implant of claim 19, wherein the optimal patient-specific three-dimensional implant comprises bulges, serrations and/or wings that are computationally optimized to inhibit over-insertion of the optimal patient-specific three dimensional implant, increase the surface area for bone ingrowth, dissipate loads transmitted from adjacent levels proximate the target zone and a connector for coupling devices distinct from the optimal patient-specific three dimensional implant.

21. The process of making the optimal patient-specific three-dimensional implant of claim 20, wherein the computationally optimized bulges, serrations, and/or wings are generated according to an algorithm that dynamically modifies the geometry of the optimal patient-specific three-dimensional implant in response to the metric for fabricating the optimal patient-specific three-dimensional implant, thereby creating a non-uniform, patient-specific structural lattice that provides a greater load-bearing capacity and a reduced risk of stress shielding.

* * * * *